United States Patent
Brandon et al.

(10) Patent No.: US 9,345,679 B2
(45) Date of Patent: *May 24, 2016

(54) HIGH-LOADING, CONTROLLED-RELEASE MAGNESIUM ORAL DOSAGE FORMS AND METHODS FOR MAKING AND USING SAME

(71) Applicant: Pharmalyte Solutions, LLC, Southlake, TX (US)

(72) Inventors: Stephen F. Brandon, Trophy Club, TX (US); Feng Zhang, Burlingame, CA (US); Stuart Schoenherr, Beeville, TX (US)

(73) Assignee: Pharmalyte Solutions, LLC, Southlake, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/811,540

(22) Filed: Jul. 28, 2015

(65) Prior Publication Data

US 2015/0335599 A1  Nov. 26, 2015

Related U.S. Application Data

(63) Continuation of application No. 14/519,823, filed on Oct. 21, 2014, now Pat. No. 9,114,103, which is a continuation of application No. 13/859,098, filed on Apr. 9, 2013, now Pat. No. 8,906,396, which is a continuation of application No. 12/467,883, filed on May 18, 2009, now Pat. No. 8,445,020.

(60) Provisional application No. 61/054,305, filed on May 19, 2008.

(51) Int. Cl.
A61K 31/194  (2006.01)
A61K 9/20   (2006.01)
A61K 9/28   (2006.01)
A61K 45/06  (2006.01)
A61K 33/06  (2006.01)

(52) U.S. Cl.
CPC ............ *A61K 31/194* (2013.01); *A61K 9/2027* (2013.01); *A61K 9/2054* (2013.01); *A61K 9/2095* (2013.01); *A61K 9/2846* (2013.01); *A61K 9/2853* (2013.01); *A61K 9/2866* (2013.01); *A61K 9/2886* (2013.01); *A61K 33/06* (2013.01); *A61K 45/06* (2013.01)

(58) Field of Classification Search
CPC . A61K 31/194; A61K 9/2853; A61K 9/2095; A61K 9/2845; A61K 9/2027; A61K 9/2054; A61K 9/2846; A61K 9/2886; A61K 45/06; A61K 33/06; A61K 2300/00
See application file for complete search history.

(56) References Cited

U.S. PATENT DOCUMENTS

| 8,445,020 | B2 * | 5/2013 | Brandon | A61K 9/2027 424/400 |
| 8,906,396 | B2 * | 12/2014 | Brandon | A61K 9/2027 424/400 |
| 9,114,103 | B2 * | 8/2015 | Brandon | A61K 9/2027 |

* cited by examiner

*Primary Examiner* — Blessing M Fubara
(74) *Attorney, Agent, or Firm* — Klemchuk LLP; Kirby B. Drake

(57) ABSTRACT

Disclosed are high loading, controlled-release dosage forms for oral administration of magnesium salts. For example, an oral dosage form can comprise from about 80% to about 95% magnesium lactate and one or more components. As another example, an oral dosage form can comprise at least about 50% magnesium salt and exhibit a controlled release dissolution profile. Also disclosed are methods for making controlled release dosage forms for oral administration of a therapeutically effective amount of magnesium salt to a mammal. Also disclosed are methods for treating a disorder characterized by magnesium deficiency and methods for preventing or alleviating low magnesium levels.

16 Claims, 26 Drawing Sheets

HIGH-LOADING, CONTROLLED-RELEASE MAGNESIUM ORAL DOSAGE FORMS AND METHODS FOR MAKING AND USING SAME

CROSS-REFERENCE TO RELATED APPLICATIONS

This present application is a continuation of U.S. patent application Ser. No. 14/519,823 filed Oct. 21, 2014 entitled "High-Loading, Controlled-Release Magnesium Oral Dosage Forms and Methods for Making and Using Same," which is a continuation of U.S. patent application Ser. No. 13/859,098 filed Apr. 9, 2013 and entitled "High-Loading, Controlled-Release Magnesium Oral Dosage Forms and Methods for Making and Using Same," which claims the benefit of U.S. application Ser. No. 12/467,883, filed May 18, 2009, as well as U.S. Application No. 61/054,305, filed May 19, 2008, all of which are hereby incorporated herein by reference in their entirety.

BACKGROUND

Magnesium is the fourth most abundant cation in the human body—second most abundant in the intracellular environment—and takes part in more than three hundred enzymatic reactions. Magnesium is also essential for normal functioning of many of the body's organs, including the heart and kidneys. Magnesium deficiency is associated with an extensive list of diseases and conditions, including heart disease, arrhythmia, diabetes, migraine headaches, and osteoporosis. These conditions affect a tremendous number of people in the United States alone.

Unfortunately, many magnesium salts currently used to treat magnesium deficiencies orally, such as magnesium oxide, magnesium chloride, magnesium sulfate, magnesium gluconate or magnesium hydroxide, exhibit extremely low to moderate bioavailability, from about 2% for magnesium oxide to about 20% for magnesium chloride and magnesium gluconate. If a magnesium salt has a low bioavailability, very little, if any, magnesium will actually be absorbed into the body and reach the cells where the magnesium is needed. As such, it is desirable to have a highly bioavailable oral dosage form of magnesium that can be prescribed by physicians in dosages necessary to achieve normal intracellular magnesium levels, which are defined as a minimum concentration of 33.9 mEq/IU.

In order to prepare a solid oral dosage form containing one or more active ingredients (e.g., a magnesium salt), it is necessary that the material to be compressed into the dosage form possess certain physical characteristics which lend themselves to processing in such a manner. Among other things, the material to be compressed must be free flowing, must be lubricated, and, importantly, must possess sufficient cohesiveness to insure that the solid dosage form remains intact after compression. Magnesium salts (in particular, high bioavailability magnesium salts, including magnesium lactate), however, typically exhibit poor compressibility. Consequently, compressibility aids can be employed to impart cohesive properties to the drug(s) being formulated. The inclusion of compressibility aids, however, limits the dosage level that can be achieved in solid, oral dosage forms. As a result, oral dosage forms comprising a high loading of a high bioavailability magnesium salt are notoriously difficult to manufacture.

Even further, high-loading tablets typically lack a controlled release profile. That is, the inclusion of materials that can delay release of a drug from the tablet can limit the dosage level that can be achieved in solid, oral dosage forms. Consequently, oral dosage forms comprising a high loading of a magnesium salt are notoriously difficult to prepare in controlled release formulations.

This lack of satisfactory controlled release formulations further decreases the effectiveness of conventional magnesium oral dosage forms. More specifically, certain transient receptor potential (TRP) ion channels are located in the distal small intestines and are involved in regulation of magnesium reabsorption in the kidneys and absorption in the intestines. TRPM is a family of transient receptor potential ion channels that includes TRPM6 and TRPM7 (transient receptor potential cation channel, subfamily M ("melastatin"), members 6 and 7). Patients with deficient intracellular $Mg^{2+}$ stores have higher uptake of $Mg^{2+}$ via TPRM6/7 transports in the distal small intestine and higher $Mg^{2+}$ reabsorption via TRPM6/7 transports in the distal convoluted tubule of the kidney resulting in less renal wasting of $Mg^{2+}$, and greater transfer of blood $Mg^{2+}$ into the intracellular compartment. Unfortunately, conventional magnesium oral dosage forms do not achieve satisfactory control of magnesium release to target this portion of the digestive tract; thus, optimal absorption is not achieved in magnesium deficient patients when using conventional formulations.

Because conventional processes for formulation of magnesium salts are unable to provide high bioavailability, high drug load, and controlled release characteristics in a single formulation, there remains a need for high-loading, controlled-release dosage forms for oral administration of highly bioavailable magnesium salts and methods for making and using same.

SUMMARY

In accordance with the purpose(s) of the present disclosure, as embodied and broadly described herein, the present disclosure, in one aspect, relates to high loading, controlled-release dosage forms for oral administration of magnesium salts and methods for making and using same.

Disclosed are high-loading dosage forms for oral administration of a therapeutically effective amount of magnesium salt to a mammal comprising magnesium lactate present as from about 80% to about 95% by weight of the dosage form and one or more components present as from about 5% to about 20% by weight of the dosage form.

Also disclosed are controlled release dosage forms for oral administration of a therapeutically effective amount of magnesium salt to a mammal comprising at least about 50% by weight of the dosage form of a magnesium salt, having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours.

Also disclosed are methods of making a controlled release dosage form for oral administration of a therapeutically effective amount of magnesium salt to a mammal comprising the step of compressing a blend of granulated magnesium salt and one or more components at a pressure sufficient to form a dosage form comprising at least about 80% by weight of the magnesium salt.

Also disclosed are products produced by the disclosed methods.

Also disclosed are methods of treating a disorder characterized by magnesium deficiency comprising administering to a mammal a therapeutically effective amount of an oral dosage form comprising at least about 80% by weight of a magnesium salt, thereby treating the disorder.

Also disclosed are methods of preventing or alleviating low magnesium levels comprising co-administering to a mammal a therapeutically effective amount of an oral dosage form comprising at least about 80% by weight of a magnesium salt and a drug having a known side-effect of decreasing intracellular magnesium levels, thereby preventing or alleviating the low magnesium levels.

Also disclosed are methods of preventing or alleviating low magnesium levels comprising co-administering to a mammal a therapeutically effective amount of an oral dosage form comprising at least about 80% by weight of a magnesium salt and a drug known to treat a disorder associated with decreasing intracellular magnesium levels, thereby preventing or alleviating the low magnesium levels.

Also disclosed are kits comprising an oral dosage form comprising at least about 80% by weight of a magnesium salt and a drug having a known side effect of decreasing intracellular magnesium levels.

Also disclosed are kits comprising an oral dosage form comprising at least about 80% by weight of a magnesium salt and a drug known to treat a disorder associated with decreasing intracellular magnesium levels.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the present disclosure.

Figure 1:
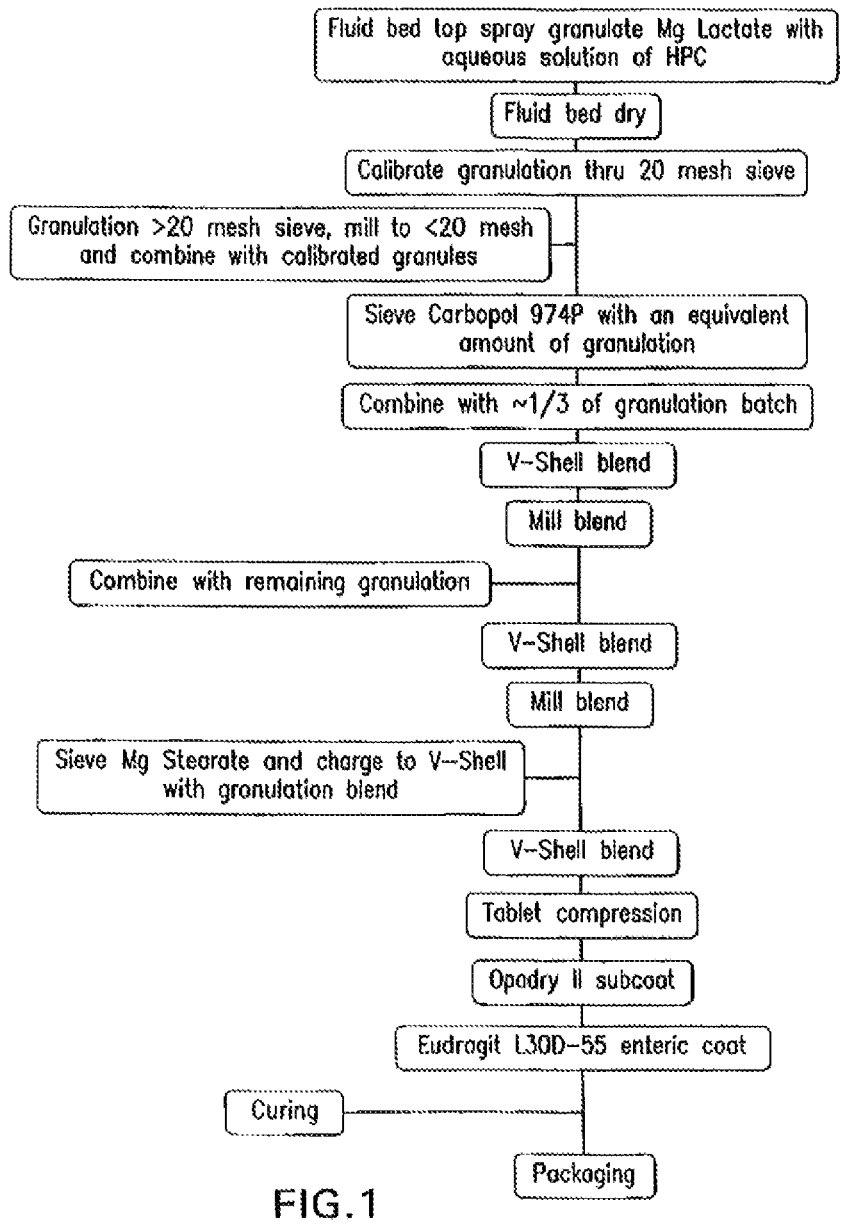
FIG. 1 shows an exemplary processing flow chart for one formulation and process for preparation.

Additional advantages of the present disclosure will be set forth in part in the description which follows, and in part will be obvious from the description, or can be learned by practice of the invention. The advantages of the present disclosure will be realized and attained by means of the elements and combinations particularly pointed out in the appended claims. It is to be understood that both the foregoing general description and the following detailed description are exemplary and explanatory only and are not restrictive of the present disclosure, as claimed.

DESCRIPTION

The present disclosure can be understood more readily by reference to the following detailed description of the present disclosure and the Examples included therein.

Before the present compounds, compositions, articles, systems, devices, and/or methods are disclosed and described, it is to be understood that they are not limited to specific synthetic methods unless otherwise specified, or to particular components unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior invention. Further, the dates of publication provided herein can be different from the actual publication dates, which may need to be independently confirmed.

A. Definitions

As used in the specification and the appended claims, the singular forms "a," "an" and "the" include plural referents unless the context clearly dictates otherwise. Thus, for example, reference to "a composition," "an agent," or "a tablet" includes mixtures of two or more such compositions, agents, or tablets, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "substantially" means that the subsequently described event or circumstance completely occurs or that the subsequently described event or circumstance generally, typically, or approximately occurs. For example, when the specification discloses that substantially all of an agent is released, a person skilled in the relevant art would readily understand that the agent need not be completely released. Rather, this term conveys to a person skilled in the relevant art that the agent need only be released to an extent that an effective amount is no longer unreleased.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "subject" refers to a living organism as a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. In certain aspects, this term can be synonymous with the language "preventative treatment."

As used herein, the terms "alleviate" or "alleviating" refer to lightening or lessening the severity of a symptom, condition, or disorder. For example, a treatment that reduces the severity of pain in a subject can be said to alleviate pain. It is understood that, in certain circumstances, a treatment can alleviate a symptom or condition without treating the underlying disorder. In certain aspects, this term can be synonymous with the language "palliative treatment."

As used herein, the term "diagnosed with" a condition refers to having been subjected to a physical examination by a person of skill, for example, a medical doctor (e.g., physician or veterinarian), and found to have the condition. It is also specifically contemplated that a subject (e.g., a mammal, a human) can be identified with such condition.

As used herein, the term "diagnosed with a need for" a treatment refers to having been subjected to a physical examination by a person of skill, for example, a physician, and found to have a condition that can be diagnosed or treated by the treatment. It is also specifically contemplated that a subject (e.g., a mammal, a human) can be identified with a need for such treatment.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectables such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In one aspect, administration of a tablet refers to oral administration.

As used herein, the term "immediate release" refers to the attribute indicating that a desired substance is released to its target environment relatively immediately. In one aspect, an "immediate release" tablet releases more than about 40% of the desired substance within hour following administration, as measured under the Tablet Dissolution Test.

As used herein, the term "controlled release" refers to the attribute indicating that a desired substance, such as a drug (e.g., a magnesium salt), is released to its target environment (e.g., a subject) in a controlled fashion, rather than immediately. Thus, a "controlled release" formulation releases no more than about 40% of the desired substance within 1 hour following administration, as measured under the Tablet Dissolution Test. "Controlled release" includes both "delayed release" and "sustained release" formulations. In one aspect, "controlled release" excludes "immediate release" formulations; however, it is contemplated that certain "controlled release" formulations can include an immediate release aspect. For example, a formulation having an immediate release control core and an enteric coating would not be referred to as an "immediate release" formulation; such a formulation can be referred to as a "controlled release" formulation and a "delayed release" formulation, but not as a "sustained release" formulation. Examples of a "controlled release" tablet include a "delayed release" tablet, a "sustained release" tablet, and a "delayed/sustained release" tablet.

As used herein, the term "delayed release" refers to the attribute indicating that a desired substance, such as a drug (e.g., a magnesium salt), is released to its target environment (e.g., a subject) at a time other than promptly after administration. In one aspect, the dosage form controls the drug release rate into the gastrointestinal tract, releasing the bulk of the drug in a portion of the gastrointestinal tract distal to the duodenum. This can decrease the incidence or severity of gastrointestinal side effects. Additionally, this can increase the amount of drug absorbed into the blood. In a further aspect, a "delayed release" formulation releases no more than about 5% of the desired substance within 2 hours following administration. In a yet further aspect, a "delayed release" formulation releases no more than about 5% of the desired substance within 2 hours following administration and releases no more than about 40% of the desired substance within 3 hours following administration. In an even further aspect, a "delayed release" formulation releases no more than about 5% of the desired substance within 2 hours following administration, no more than about 40% of the desired substance within 3 hours following administration, and no more than about 80% of the desired substance within 8 hours following administration. In an even further aspect, a "delayed release" formulation releases no more than about 5% of the desired substance within 2 hours following administration, no more than about 40% of the desired substance within 4 hours following administration, and from about 50 to about 80% of the desired substance within 8 hours following administration. In a further aspect, substantially the entire drug is released within 12 hours. "Delayed release" is a subset of "controlled release." FDA guidelines also refer to a "delayed release" tablet as a solid dosage form, which releases a drug (or drugs) at a time other than promptly after administration. Enteric-coated articles are delayed release dosage forms. The term includes both "delayed release" tablets and "delayed/sustained release" tablets.

As used herein, the term "sustained release" refers to the attribute indicating that a desired substance, such as a drug (e.g., a magnesium salt), is released to its target environment (e.g., a subject) in a desired dosage, which is maintained over a desired interval. In one aspect, this attribute can be also referred to as "extended release" or "prolonged release." In one aspect, the dosage form controls the drug release rate so as to decrease the frequency of dosing. This can maintain desired blood levels of the drug independent of dosing frequency. This can also increase patient compliance with a given treatment regimen. In a further aspect, the dosage form controls the drug release rate so as to target the distal small intestine. In a yet further aspect, the dosage form controls the drug release rate so as to target the distal small intestine, thereby increasing the amount of magnesium available for interaction with TRPM6 and/or TRPM7 cation channels. In a further aspect, a "sustained release" formulation releases no more than about 40% of the desired substance within 1 hour following administration. In a yet further aspect, a "sustained release" formulation releases no more than about 40% of the desired substance within 1 hour following administration, and no more than about 80% of the desired substance within 6 hours following administration. In an even further aspect, a "sustained release" formulation releases no more than about 40% of the desired substance within 1 hour following administration, and from about 50% to about 80% of the desired substance within 6 hours following administration. In a further aspect, substantially the entire drug is released within 10 hours. In a still further aspect, a "sustained release" formulation releases no more than about 5% of the desired substance within 2 hours following administration and releases no more than about 40% of the desired substance within 3 hours following administration. In an even further aspect, a "sustained release" formulation releases no more than about 5% of the desired substance within 2 hours following administration, no more than about 40% of the desired substance within 3 hours following administration, and no more than about 80% of the desired substance within 8 hours following administration. In an even further aspect, a "sustained release" formulation releases no more than about 5% of the desired substance within 2 hours following administration, no more than about 40% of the desired substance within 3 hours following administration, and from about 50% to about 80% of the desired substance within 8 hours following administration. In a further aspect, substantially all of the entire drug is released within 12 hours. "Sustained release" is a subset of "controlled release." FDA guidelines also refer to a "sustained release"

tablet as an "extended release tablet"—that is, a solid dosage form containing a drug which allows at least a reduction in dosing frequency as compared to that drug presented in conventional dosage form. The term includes both "sustained release" tablets and "delayed/sustained release" tablets.

As used herein, the term "delayed/sustained release" refers to the attribute indicating that a desired substance, such as a drug (e.g., a magnesium salt), is released to its target environment (e.g., a subject) at a time other than promptly after administration and released to its target environment in a desired dosage, which is maintained over a desired interval. In one aspect, the dosage form controls the drug release rate into the gastrointestinal tract, releasing the bulk of the drug in a portion of the gastrointestinal tract distal to the duodenum. This can decrease the incidence or severity of gastrointestinal side effects. Additionally, this can increase the amount of drug absorbed into the blood. In a further aspect, the dosage form controls the drug release rate so as to target the distal small intestine. In a yet further aspect, the dosage form controls the drug release rate so as to target the distal small intestine, thereby increasing the amount of magnesium available for interaction with TRPM6 and/or TRPM7 cation channels. In one aspect, the dosage form controls the drug release rate so as to decrease the frequency of dosing. This can maintain desired blood levels of the drug independent of dosing frequency. This can also increase patient compliance with a given treatment regimen. In a further aspect, a "delayed/sustained release" formulation releases no more than about 5% of the desired substance within 2 hours following administration and releases no more than about 40% of the desired substance within 3 hours following administration. In an even further aspect, a "delayed/sustained release" formulation releases no more than about 5% of the desired substance within 2 hours following administration, no more than about 40% of the desired substance within 3 hours following administration, and no more than about 80% of the desired substance within 8 hours following administration. In an even further aspect, a "delayed/sustained release" formulation releases no more than about 5% of the desired substance within 2 hours following administration, no more than about 40% of the desired substance within 3 hours following administration, and from about 50% to about 80% of the desired substance within 8 hours following administration. In a further aspect, substantially of all of the entire drug is released within 12 hours. "Delayed/sustained release" is a subset of "controlled release." "Delayed/sustained release" is a subset of "delayed release." "Delayed/sustained release" is a subset of "sustained release."

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual's physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount;" that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Disclosed are the components to be used to prepare the compositions of the present disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compositions

In one aspect, the present disclosure relates to oral dosage forms comprising a magnesium salt and one or more additional components. For example, the disclosed oral dosage forms can be high loading and/or controlled release dosage forms for oral administration of a therapeutically effective amount of magnesium salt. In a further aspect, the magnesium salt is magnesium lactate, for example, magnesium L-lactate dihydrate.

It is understood that the oral dosage forms can be provided as capsules, tablets, pills, dragees, powders, granules and the like. Because of their ease of administration, tablets and capsules are the preferred oral dosage units whereby solid pharmaceutical carriers are employed. Thus, in one aspect, a disclosed oral dosage form can be a tablet. In one aspect, the oral dosage form has a total weight of no more than about 1500 mg, for example, of about 1350 mg. Optionally, tablets can be coated by standard aqueous or nonaqueous techniques.

A tablet containing the composition of this disclosure can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active, or dispersing agent. Molded tablets can be made by molding in a suitable machine, a mixture of the powdered compound moistened with an inert liquid diluent.

In one aspect, the oral dosage forms comprise a core formed from a plurality of particles, which comprise particles comprising a magnesium salt (e.g., magnesium lactate) and a pharmaceutically acceptable carrier or diluent. Although the particles can be compressed to form a solid core, it can be useful to describe the core as a grouping of compressed particles. Particle size of the particles can be selected using routine sieving techniques. In one aspect, the particles have a diameter of less than about 20 mesh (840 um). For example, the particles can have a diameter of from about 50 um to about 840 um.

It is understood that the disclosed oral dosage forms can be prepared by the disclosed methods of making. It is also understood that the disclosed oral dosage forms can be used in connection with the disclosed methods of using. It is also understood that the disclosed oral dosage forms can be employed in connection with the disclosed kits.

1. Magnesium Salt

In one aspect, the magnesium salt is one or more of magnesium carbonate, magnesium chloride, magnesium citrate, magnesium fumerate, magnesium gluconate, magnesium glycinate, magnesium L-lactate, magnesium oxide, magnesium DL-aspartate, magnesium L-aspartate, magnesium hydroxide, magnesium salicylate, magnesium sulfate, magnesium aminoate, magnesium phosphate, magnesium acetate, magnesium pidolate, magnesium malate, or magnesium picolinate.

In a further aspect, the magnesium salt is selected to be a highly bioavailable magnesium salt. By "highly bioavailable," it is meant that the salt has a bioavailability of at least about 30%, for example at least about 40%. Examples of such magnesium salts include magnesium lactate, magnesium DL-aspartate, and magnesium L-aspartate. In one aspect, the magnesium salt is magnesium lactate (2-hydroxypropanoic acid magnesium salt), for example, magnesium L-lactate dihydrate (commercially available as a powder from Jost).

By varying the selected amount of magnesium salt employed during preparation of the oral dosage forms, the high-loading dosage form can, in various aspects, be provided with at least about 8 mEq of magnesium, at least about 9 mEq of magnesium, or about 10 mEq of magnesium. Likewise, the high-loading dosage form can, in various further aspects, be provided with magnesium salt present as from about 85% to about 95%, from about 85% to about 90%, from about 90% to about 95%, or from about 87% to about 92% by weight of the dosage form. For example, the high-loading dosage form can be provided with at least about 8 mEq of magnesium salt (e.g., magnesium lactate) present as from about 85% to about 95% by weight of the dosage form.

2. Additional Components

In various aspects, the one or more components can comprise fillers, binders, buffering agents, and/or lubricants. The oral dosage forms can further comprise one or more coating layers. It is understood that additional components (e.g., diluents, preservatives, disintegrants, excipients, etc.) can also be employed in the oral dosage forms.

a. Fillers/Diluents

In one aspect, the oral dosage forms can comprise fillers, diluents, or extenders, such as starches, lactose, sucrose, glucose, mannitol, or silicic acid. Fillers fill out the size of a tablet or capsule, making it practical to produce and convenient for the consumer to use. By increasing the bulk volume, the final product can have a desired volume for patient handling. Typically, a filler is inert, compatible with the other components of the formulation, non-hygroscopic, soluble, relatively cheap, compactable, and preferably tasteless or pleasant tasting. Plant cellulose, dibasic calcium phosphate, and vegetable fats and oils can also be employed as fillers. Other examples of fillers include mannitol, sorbitol, and calcium carbonate.

b. Disintegrants

In one aspect, the oral dosage forms can comprise disintegrating agents, such as agar-agar, calcium carbonate, potato or tapioca starch, alginic acid, certain silicates, or sodium carbonate. Disintegrants expand and dissolve when wet, causing the tablet to break apart in the digestive tract, releasing the active ingredients for absorption. Examples of disintegrants include: starch, cellulose, cross-linked polyvinyl pyrrolidone, sodium starch glycolate, sodium carboxymethycellulose, starch glycolate, and cross-linked sodium carboxymethyl cellulose.

Further examples of disintegrants for use in the dosage forms include croscarmellose sodium, crospovidone, alginic acid, sodium alginate, methacrylic acid DVB, cross-linked PVP, microcrystalline cellulose, polacrilin potassium, sodium starch glycolate, starch, pregelatinized starch and the like. In at least one aspect the disintegrant is selected from cross-linked polyvinylpyrrolidone (e.g. KOLLIDON® CL), cross-linked sodium carboxyinethylcellulose (e.g. Ac-Di-Sol), starch or starch derivatives such as sodium starch glycolate (e.g. EXPLOTAB®), or combinations with starch (e.g. PRIMOJEL™), swellable ion-exchange resins, such as Ainberlite JRP 88, formaldehyde-casein (e.g. ESNIA SPRENG™), and mixtures thereof. In at least one aspect the disintegrant is sodium starch glycolate.

c. Binders

A binder (also sometimes called adhesive) can be added to a drug-filler mixture to increase the mechanical strength of the granules and tablets during formation. Binders can be added to the formulation in different ways, for example: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. Binders include solution binders and dry binders. Solution binders can be dissolved in a solvent and used in wet granulation processes. Examples are gelatin, cellulose, cellulose derivatives, polyvinyl pyrrolidone, starch, sucrose, and polyethylene glycol. Dry binders can be added to the powder blend, either after a wet granulation step, or as part of a direct powder compression formula. Examples are cellulose, methylcellulose, polyvinyl pyrrolidone, and polyethylene glycol.

Thus, in one aspect, the oral dosage forms can comprise one or more binders, such as, for example, carboxymethylcellulose, alginates, gelatin, polyvinyl pyrrolidone, sucrose, and acacia. Binders hold the ingredients in a tablet together, thereby ensuring that tablets and granules can be formed with required mechanical strength. Binders can be starches, sugars, cellulose or modified cellulose such as hydroxypropyl cellulose, lactose, or sugar alcohols like xylitol, sorbitol or maltitol.

Further examples of binders useful for the core include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, sterile alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof.

In one aspect, the one or more components comprise a binder. In a further aspect, the one or more components comprise a cross-linked acrylic acid-based polymer (available as, e.g., CARBOPOL® 974P or CARBOPOL® 971P from Lubrizol) and/or hydroxypropyl cellulose (available as, e.g., KLUCEL® EF from Aqualon). In various aspects, suitable acrylic polymers include acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) anhydride, polymethacrylate, polyacrylamide, and glycidyl methacrylate copolymers. In a further aspect, the one or more components do not comprise hydroxypropyl methylcellulose in a high sheer granulation process. In a yet further aspect, the one or more components do not comprise hydroxypropyl methylcellulose.

In one aspect, the binder is Carbopol® 971P, which is a lightly cross-linked polymer that swells at a faster rate and to a greater extent than Carbopol® 974P. Carbopol® 971P provides for increased control of dissolution rate compared to many other binders and can be employed at a lower loading level than Carbopol® 974P.

During development of the tablet core for the purpose of applying a sustained release coating, an optional controlled release matrix was discovered. In one aspect, this matrix is based on an increased level of hydroxypropyl cellulose applied during the fluid bed top spray granulation process. In order to overcome potential ejection problems arose on the tablet press, in one aspect, an increased amount of lubricant was employed. In conventional processes, a potential detriment associated with increasing the lubricant amount to a high level is the loss of compressibility. However, in the disclosed formulations, this was not observed, and robust tablets with favorable dissolution results were achieved.

In other aspects, a controlled release matrix is provided from which the kinetics of drug release from the matrix core are dependent at least in part upon the diffusion and/or erosion properties of excipients within the composition. In this aspect controlled release matrices contain an effective amount of a magnesium salt and at least one pharmaceutically acceptable excipient.

The controlled release matrix can be multiparticulate or uniparticulate, and can be coated with at least one functional or non-functional coating, or an immediate release coating containing a magnesium salt or other drug. Functional coatings include by way of example controlled release polymeric coatings, enteric polymeric coatings, and the like. Non-functional coatings are coatings that do not affect drug release but which affect other properties (e.g., they may enhance the chemical, biological, or the physical appearance of the controlled release formulation).

Non-limiting examples of hydrophilic polymers that can be used in certain aspects of the controlled release matrix dosage form include hydroxypropylmethylcellulose (HPMC), hydroxypropylcellulose (HPC), hydroxyethylcefluose (HEC), carboxymethylcellulose (CMC) or other cellulose ethers, polyoxyethylene, alginic acid, acrylic acid derivatives such as polyacmylic acid, Carbopol (B. F. Goodrich, Cleveland, Ohio), polymethacrylate polymer such as EUDRAGIT® RL, RS, R. S, NE and E (Rhome Pharma, Darmstadt, Germany), acrylic acid polymer, methacrylic acid polymer, hydroyethyl methacrylic acid (HEMA) polymer, hydroxymethyl methacrylic acid (HMMA) polymer, and polyvinyl alcohols.

In at least one aspect, the controlled release matrix dosage form comprises hydroxypropylmethylcellulose (HPMC). HPMC is an anhydroglucose in which some of the hydroxyl groups are substituted with methyl groups to form methyl ether moieties, and others are substituted with hydroxypropyl groups or with methoxypropyl groups to form hydroxypropyl ether or methoxypropyl ether moieties. Examples of hydroxypropyl methylcelluloses that are commercially available include METHOCEL® E (USP type 2910), METHOCEL® F (USP type 2906), METHOCEL® J (USP type 1828), METHOCEL® K (USP type 2201), and METHOCEL® 310 Series, products of The Dow Chemical Company, Midland, Mich., USA. The dosage form can comprise the different HPMC grades having different viscosities. Different HPMC grades can be combined to achieve the desired viscosity characteristics. For example, the at least one pharmaceutically acceptable polymer can comprise two HPMC polymers such as for example METHOCEL® K3 LV (which has a viscosity of 3 cps) and METHOCEL® K100M CR (which has a viscosity of 100,000 cps). In addition, the polymer can comprise two hydroxypropylcellulose forms such as KLUCEL® LF and KLUCEL® EF. In addition, the at least one polymer can comprise a mixture of a KLUCEL® and a METHOCEL®.

In at least one aspect the controlled release matrix dosage form comprises a polyethylene oxide (PEO). PEO is a linear polymer of unsubstituted ethylene oxide. In certain aspects poly (ethylene oxide) polymers having viscosity-average molecular weights of 100,000 daltons and higher are used. Non-limiting examples of poly(ethylene oxide)s that are commercially available include: POLYOX® NF, grade WSR Coagulant, molecular weight 5 million; POLYOX® grade WSR 301, molecular weight 4 million; POLYOX® grade WSR 303, molecular weight 7 million; POLYOX® grade WSR N-60 K, molecular weight 2 million; and mixtures thereof. These particular polymers are products of Dow Chemical Company, Midland, Mich., USA. Other examples of polyethylene oxides exist and can likewise be used. A desired molecular weight for the PEO can be obtained by mixing PEO of differing molecular weights that are available commercially.

In at least one aspect of the controlled release matrix dosage form, PEO and HPMC are combined within the same controlled release matrix. In certain aspects, the poly (ethylene oxide)s have molecular weights ranging from U.S. Pat. No. 2,000,000 to Ser. No. 10/000,000 Da. For example, in at least one aspect the polyethylene oxides have molecular weights ranging from 4,000,000 to 7,000,000 Da. In certain aspects the HPMC polymers have a viscosity within the range of 4,000 centipoise to 200,000 centipoise. For example, in at least one aspect the HPMC polymers have a viscosity of from 50,000 centipoise to 200,000 centipoise, and in other aspects from 80,000 centipoise to 120,000 centipoise. The relative amounts of PEO and HPMC within the controlled release matrix can vary within the scope of the present disclosure. In at least one aspect the PEO:HPMC weight ratio is from 1:3 to 3:1. For example, in certain aspects the PEO:HPMC weight ratio is from 1:2 to 2:1. As for the total amount of polymer relative to the entire matrix, this can vary as well and can depend on the desired drug loading.

In at least one aspect of the disclosure the controlled release matrix dosage form comprises a hydrophobic polymer such as ethylcellulose. The viscosity of ethylcellulose can be selected in order to influence of rate the drug release. In certain aspects the ethylcellulose has a viscosity from 7 to 100 cP (when measured as a 5% solution at 25° C. in an Ubbelohde viscometer, using a 80:20 toluene:ethanol solvent). In certain aspects the hydrophobic polymer can constitute from 10% to 90% by weight of the matrix dosage form. For example, in at least one aspect the hydrophobic polymer constitutes from 20% to 75%, and in other aspects from 30% to 60% by weight of the matrix dosage form.

In at least one aspect, the binder can further comprise one or more gums. Polysaccharide gums, both natural and modified (semi-synthetic), can be used in the binder aspects of the present disclosure. Examples include dextran, xanthan gum, gellan gum, welan gum, rhamsan gum, guar gum, and mixtures thereof. In at least one aspect, the polysaccharide gum is xanthan gum.

In at least one aspect, the binder can further comprise at least one diluent. Examples include dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol, sucralfate, calcium hydroxyl-apatite, calcium phosphates and fatty acid salts such as magnesium stearate.

d. Glidants

In one aspect, the one or more components comprise a glidant. Glidants can be used to improve the flowability of the powder or granules or both. Examples include silicon dioxide, cellulose, microcrystalline cellulose, metallic stearates, sodium aluminosilicate, sodium benzoate, calcium carbonate, and combinations thereof.

e. Lubricants

Lubricants can be added to avoid the material(s) being tableted from sticking to the punches of a tablet press. Such lubricants are commonly included in the final tableted product in amounts of less than 1% by weight. Commonly used lubricants include magnesium stearate, calcium stearate, talc, solid polyethylene glycols, sodium lauryl sulfate, and mixtures thereof. In one aspect, the one or more components comprise a lubricant, for example, magnesium stearate (available from Mallinckrodt).

Further examples of lubricants include stearic acid, hydrogenated vegetable oils (such as hydrogenated cottonseed oil (STEROTEX®), hydrogenated soybean oil (STEROTEX® HM) and hydrogenated soybean oil & castor wax (STEROTEX® K)) sterile alcohol, leucine, polyethylene glycol (MW 1450, suitably 4000, and higher), magnesium stearate, glyceryl monostearate, stearic acid, glycerylbehenate, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate, sodium stearyl fumarate, DL-leucine, colloidal silica, and mixtures thereof.

f. Flavorants and Colorants

Flavors and colors can be added to improve the taste or appearance of a formulation. In one aspect, the one or more components comprise a colorant. Color consistency can be desirable, as it allows easy identification of a medication. Suitable colorants include titanium dioxide, iron oxides, natural pigments, dyes, and lakes approved for ingestion by the U.S. Federal Drug Administration, or combinations thereof.

In one aspect, the one or more components comprise a flavorant. Suitable flavorants include vanillin, sodium citrate, citric acid, mint, orange, lemon oil, or any other pharmaceutically approved flavorant or tastemasking agent, and combinations thereof. Sweeteners can also be added to make the ingredients more palatable. For example, sugar can be used to disguise unpleasant tastes or smells.

g. Preservatives

In one aspect, the one or more components comprise a preservative. Suitable preservatives include antioxidants like vitamin A, vitamin E, vitamin C, retinyl palmitate, and selenium; the amino acids cysteine and methionine; citric acid and sodium citrate; and synthetic preservatives like methylparaben and propylparaben.

h. Sorbents

In one aspect, the one or more components comprise a sorbent. Sorbents are used for tablet/capsule moisture proofing by limited fluid sorbing (i.e., taking up of a liquid or a gas either by adsorption or by absorption) in a dry state. Suitable sorbents include kaolin and bentonite clay.

i. Wetting Agents

In one aspect, the one or more components comprise a wetting agent. Wetting agents can be added to a liquid in small quantities in order to enhance the spread of the liquid on a surface or the penetration of the liquid into a material. Suitable wetting agents include cetyl alcohol and glycerol monostearate.

3. Surface Coatings

In various further aspects, the oral dosage forms can further comprise one or more coating layers. A coating layer can be a sustained release coating, an enteric coating, and/or a barrier layer.

Thus, in one aspect, the particles of the oral dosage form can form a core having a first surface coating thereon. In a further aspect, the first surface coating can be a sustained release coating. In a further aspect, the first surface coating can be a barrier coating. In a further aspect, the first surface coating can be an enteric coating.

In one aspect, the oral dosage form can comprise a second surface coating on the core. In a further aspect, the second coating is layered upon the first coating. In a further aspect, the second surface coating can be a sustained release coating. In a further aspect, the second surface coating can be a barrier coating. In a further aspect, the second surface coating can be an enteric coating. Typically, when two or more coatings are employed, at least one (and, preferably, the first) is a barrier coating. Thus, in a further aspect, the first surface coating comprises a barrier coating, and the second surface coating comprises an enteric coating.

In a further aspect, the oral dosage form can comprise a moisture barrier surrounding the one or more surface coating(s) or the core.

Thus, in one aspect, the present disclosure relates to a high-loading dosage form for oral administration of a therapeutically effective amount of magnesium salt to a mammal comprising magnesium lactate present as from about 80% to about 95% by weight of the dosage form; one or more components present as from about 5% to about 20% by weight of the dosage form; and one or more surface coatings. In a further aspect, the disclosure relates to a controlled release dosage form for oral administration of a therapeutically effective amount of magnesium salt to a mammal comprising at least about 50% by weight of the dosage form of a magnesium salt, having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours; and one or more surface coatings.

a. Sustained Release Coating

As another example, the one or more coatings can comprise a sustained release coating, which is a coating on tablets that delays release of a drug from the tablet. In one aspect, the coating layer comprises a relatively insoluble material or materials, and the release of the drug is controlled by means of the resistance of the coating layer or matrix against the diffusion of the drug there through. The release of the drug from such formulations is driven, e.g., by the gradient of the drug concentration resulting from penetration of, e.g., gastric fluid, by diffusion into the formulation.

Examples of sustained release coatings include hydrophobic materials, ethyl cellulose, ethyl cellulose, and copolymers of ethyl acrylate, methyl methacrylate and trimethylammonioethyl methacrylate; listed under the monograph Ammonia Methacrylate Copolymer, Type A and B. Water-soluble excipients can also be used as pore-forming agents in sustained release film coating.

b. Enteric Coating

As another example, the one or more coatings can comprise an enteric coating, which is a coating on tablets that delays digestion of the tablets until they pass from the stomach into the intestines. Enteric coatings typically comprise pH sensitive polymers. The polymers can be carboxylate and generally interact very little with water at low pH. At a high pH, however, the polymers ionize, thereby causing dissolving of the polymer. Coatings can thus be designed to remain intact in the acidic environment of the stomach, but to dissolve in the more alkaline environment of the intestine.

Examples include cellulose acetate phthalate, hydroxypropylmethylethylcellulose succinate, hydroxypropylmethylcellulose phthalate, polyvinyl acetate phthalate, and methacrylic acid-methyl methacrylate copolymer.

In one aspect, the first surface coating comprises polyvinyl alcohol. In a further aspect, the first surface coating comprises methacrylic acid-ethyl acrylate copolymer. In a further aspect, the first surface coating comprises polyvinyl alcohol and methacrylic acid-ethyl acrylate copolymer. In a further aspect, the first surface coating is an enteric coating comprising one or more of polyvinyl alcohol or methacrylic acid-ethyl acrylate copolymer. In a further aspect, the first surface coating is an enteric coating comprising one or more of CAP, PVAP, acrylic polymers, acrylic copolymers, HPMCAS, HPMCP, or shellac.

c. Barrier Layer

As another example, the one or more coatings can comprise a barrier coating or sub-coat, which is typically an intermediate layer between a tablet core and an enteric coating and/or a sustained release coating. A barrier layer can retard interaction between the core materials and the coating materials.

Typically, a barrier layer comprises either hydrophobic or hydrophilic materials. Thus, in one aspect, the first surface coating comprises a barrier layer comprising a hydrophobic material. In a further aspect, the first surface coating comprises a barrier layer comprising a hydrophilic material. In a further aspect, the first surface coating comprises polyvinyl alcohol. Hydrophilic surface coatings include hydroxypropyl cellulose, hydroxypropylmethyl cellulose, hydroxyethyl cellulose, polyvinyl pyrrolidone, polyethylene glycol, amino alkyl methacrylate copolymers, maltodextrins, and polydextrose.

4. High-Loading Dosage Forms

Because magnesium lactate notoriously suffers from poor compressibility, conventional magnesium lactate tablet formulations typically include a compressibility aid material for improving the compressibility of the magnesium lactate powder. The compressibility aid typically includes both an amount of a water insoluble waxy material and an amount of a water soluble and/or swellable polymeric material. It is widely believed that such a compressibility aid encases the grains of the magnesium lactate powder. The encasing material, in comparison to the magnesium lactate powder, is highly compressible and as such, may be easily compressed into tablet form. The inclusion of compressibility aids, however, limits the dosage level that can be achieved in solid, oral dosage forms. As a result, oral dosage forms comprising a high loading of a high bioavailability magnesium salt (e.g., magnesium lactate) are notoriously difficult to manufacture.

However, in view of the instantly disclosed techniques, the need for substantial amounts of compressibility aids can be obviated. Thus, solid oral dosage forms of highly bioavailable magnesium salts (e.g., magnesium lactate) can be prepared.

In one aspect, the disclosure relates to a high-loading dosage form for oral administration of a therapeutically effective amount of magnesium salt to a mammal comprising magnesium lactate present as from about 80% to about 95% by weight of the dosage form and one or more components present as from about 5% to about 20% by weight of the dosage form.

In certain aspects, the high-loading dosage form is also a controlled release oral dosage form. Thus, in a further aspect, the dosage form controls the magnesium lactate release rate into the gastrointestinal tract of the mammal, the dosage form releasing the bulk of its magnesium lactate in a portion of the gastrointestinal tract distal to the duodenum. For example, the controlled release rate can decrease the incidence or severity of gastrointestinal side effects and/or increase the amount of magnesium lactate absorbed into the blood. In a further aspect, the dosage form controls the drug release rate so as to target the distal small intestine. In a yet further aspect, the dosage form controls the drug release rate so as to target the distal small intestine, thereby increasing the amount of magnesium available for interaction with TRPM6 and/or TRPM7 cation channels.

In one aspect, a high-loading dosage form comprises from about 80% to about 95% by weight of magnesium lactate; up to about 20% by weight of hydroxypropyl cellulose; and optionally, up to about 5% by weight lubricant. In a further aspect, the dosage form further comprises up to about 10% by weight of a cross-linked acrylic acid-based polymer. In a further aspect, the dosage form further comprises an enteric coating at the surface of the dosage form. In a further aspect, the dosage form further comprises a barrier coating and an enteric coating at the surface of the dosage form. In a further aspect, the lubricant is magnesium stearate.

In one aspect, a high-loading dosage form comprises from about 80% to about 95% by weight of magnesium lactate; up to about 10% by weight of a cross-linked acrylic acid-based polymer; optionally, up to about 5% by weight lubricant; and the balance of weight of hydroxypropyl cellulose. In a further aspect, the dosage form further comprises an enteric coating at the surface of the dosage form. In a further aspect, the dosage form further comprises a barrier coating and an enteric coating at the surface of the dosage form. In a further aspect, the lubricant is magnesium stearate.

In one aspect, a high-loading dosage form comprises from about 80% to about 95% by weight of magnesium lactate; up to about 10% by weight of hydroxypropyl cellulose; optionally, up to about 5% by weight lubricant; and the balance of weight of a cross-linked acrylic acid-based polymer. In a further aspect, the dosage form further comprises an enteric coating at the surface of the dosage form. In a further aspect, the dosage form further comprises a barrier coating and an enteric coating at the surface of the dosage form. In a further aspect, the lubricant is magnesium stearate.

In one aspect, a high-loading dosage form comprises about 85% to about 95% by weight of magnesium lactate; from about 5% to about 15% by weight of a cross-linked acrylic acid-based polymer and/or hydroxypropyl cellulose; and optionally, up to about 5% by weight lubricant. In a further aspect, the dosage form further comprises an enteric coating at the surface of the dosage form. In a further aspect, the dosage form further comprises a barrier coating and an enteric coating at the surface of the dosage form. In a further aspect, the lubricant is magnesium stearate.

In one aspect, a high-loading dosage form comprises from about 88% to about 93% by weight of magnesium lactate; from about 1% to about 6% by weight of a cross-linked acrylic acid-based polymer; from about 4.5% to about 5.5% by weight of hydroxypropyl cellulose; and from about 0% to about 1.5% by weight of magnesium stearate. In a further aspect, the dosage form further comprises an enteric coating at the surface of the dosage form. In a further aspect, the dosage form further comprises a barrier coating and an enteric coating at the surface of the dosage form.

In one aspect, a high-loading dosage form comprises from about 80% to about 95% by weight of magnesium lactate; up to about 20% by weight of binder; and optionally, up to about 5% by weight of lubricant. In a further aspect, the binder comprises one or more of a cross-linked acrylic acid-based polymer or hydroxypropyl cellulose. In a further aspect, the binder comprises a cross-linked acrylic acid-based polymer. In a further aspect, the binder comprises hydroxypropyl cellulose. In a further aspect, the binder comprises a cross-linked acrylic acid-based polymer and hydroxypropyl cellulose. In a further aspect, the dosage form further comprises an enteric coating at the surface of the dosage form. In a further aspect, the dosage form further comprises a barrier coating and an enteric coating at the surface of the dosage form. In a further aspect, the lubricant is magnesium stearate.

In one aspect, a high-loading dosage form comprises from about 80% to about 95% by weight of magnesium lactate; up to about 20% by weight of a cross-linked acrylic acid-based polymer; and optionally, up to about 5% by weight lubricant. In a further aspect, the dosage form further comprises up to about 10% by weight of hydroxypropyl cellulose. In a further aspect, the dosage form further comprises an enteric coating at the surface of the dosage form. In a further aspect, the dosage form further comprises a barrier coating and an enteric coating at the surface of the dosage form. In a further aspect, the lubricant is magnesium stearate.

5. Controlled Release Dosage Forms

In one aspect, the disclosure relates to a controlled release dosage form for oral administration of a therapeutically effective amount of magnesium salt to a mammal comprising at least about 50% by weight of the dosage form of a magnesium salt, having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours. In a further one aspect, from about 20% to about 40% magnesium salt is released at 1 hour. In a further aspect, from about 50% to about 80% magnesium salt is released at 6 hours. In a further aspect, the magnesium salt can be present as at least about 80%, as from about 80% to about 95%, or as about 90% by weight of the dosage form.

In certain aspects, the controlled release dosage form is also a high-dosage oral dosage form. In certain aspects, the controlled release dosage form is also a delayed release oral dosage form. In certain aspects, the controlled release dosage form is also a sustained release oral dosage form. Thus, in a further aspect, the dosage form controls the magnesium lactate release rate into the gastrointestinal tract of the mammal, the dosage form releasing the bulk of its magnesium lactate in a portion of the gastrointestinal tract distal to the duodenum. For example, the controlled release rate can decrease the incidence or severity of gastrointestinal side effects and/or increase the amount of magnesium lactate absorbed into the blood. In a further aspect, the dosage form controls the drug release rate so as to target the distal small intestine. In a yet further aspect, the dosage form controls the drug release rate so as to target the distal small intestine, thereby increasing the amount of magnesium available for interaction with TRPM6 and/or TRPM7 cation channels.

Measurement of the dissolution profiles for the various disclosed controlled release dosage forms was performed by using the Tablet Dissolution Test, as described in the Examples section. As used herein, the term "uncoated core dissolution profile" refers to the result of the Tablet Dissolution Test performed on a dosage form core in the absence of a coating layer.

In one aspect, the disclosure relates to a controlled release dosage form comprising a core having a first surface coating thereon. The coating layer can be a sustained release coating, an enteric coating, and/or a barrier layer.

Thus, in a further aspect, the disclosure relates to a dosage form having a dissolution profile under the Tablet Dissolution Test characterized by less than about 5% by weight magnesium salt released at 2 hours, no more than about 40% by weight magnesium salt released at 3 hours, at least about 50% by weight magnesium salt released at 8 hours, and substantially all magnesium salt released at 12 hours. In a further aspect, at least about 20% by weight magnesium salt is released at 3 hours. In a further aspect, from about 20% to about 40% magnesium salt is released at 3 hours. In a further aspect, less than about 80% by weight magnesium salt is released at 8 hours. In a further aspect, from about 50% to about 80% magnesium salt is released at 8 hours.

In one aspect, the first surface coating comprises polyvinyl alcohol. In a further aspect, the first surface coating comprises methacrylic acid-ethyl acrylate copolymer.

In a yet further aspect, the controlled release dosage form comprising a core having a first surface coating thereon can further comprise a second surface coating on the core. The second surface coating layer can be a sustained release coating, an enteric coating, and/or a barrier layer. In one aspect, the first surface coating comprises a barrier coating, and the second surface coating comprises an enteric coating.

Measurement of the dissolution profiles for the various disclosed sustained release dosage forms was performed by using the Tablet Dissolution Test, as described in the Examples section. As used herein, with reference to a coated tablet, the term "dissolution profile" refers to the result of the Tablet Dissolution Test performed on a dosage form core having a sustained release coating or enteric coating layered thereon.

A composition that can be employed in various aspects of the disclosed high loading and/or controlled release oral dosage forms is tabulated in Table 1A, below.

TABLE 1A

Core Tablet Formula

| Compound | w/w % | mg/tablet | Supplier |
|---|---|---|---|
| Mg Lactate Dihydrate, powder | 89.25 | 1177 | Jost |
| Carbopol 974P (extragranular) | 5.00 | 66 | Lubrizol |
| Klucel EF* | 4.75 | 63 | Aqualon |
| Mg Stearate | 1.00 | 13 | Mallinckrodt |
| Tablet Total | 100.00 | 1319 | |

*applied as part of a 10% solution in DI Water

2% Sub-coated Tablet Formula

| Compound | w/w % | mg/tablet | Supplier |
|---|---|---|---|
| Opadry II Clear (85F19250) | 12.00 | 26 | Colorcon |
| DI Water | 88.00 | non-residual | In House |
| Tablet Total | 100.00 | 1345 | |

6% Enteric Coated Tablet Formula

| Compound | w/w % | Solids w/w % | Mg/tablet | Supplier |
|---|---|---|---|---|
| Eudragit L30D-55 | 56.94 | 83.33 | 66 | Degussa |
| Triethyl Citrate | 2.56 | 12.50 | 10 | Morflex |

TABLE 1A-continued

| Imwitor 900K | 0.85 | 4.17 | 3 | Sasol |
|---|---|---|---|---|
| DI Water | 39.64 | n/a | non-residual | — |
| Tablet Total | 100.00 | 100.00 | 1425 | |

Note:
coating wt gain calculation based on core tablet weight

C. Methods of Making Oral Dosage Forms

In one aspect, the present disclosure relates to methods for providing high-loading and/or controlled release dosage forms for oral administration of a therapeutically effective amount of magnesium salt. In a further aspect, the magnesium salt is magnesium lactate, for example, magnesium L-lactate dihydrate.

Thus, in a further aspect, the present disclosure relates to methods of making a high-loading, controlled release dosage form for oral administration of a therapeutically effective amount of magnesium salt to a mammal comprising the step of compressing a blend of granulated magnesium salt and one or more components at a pressure sufficient to form a dosage form comprising at least about 80% by weight of the magnesium salt.

In a yet further aspect, the dosage form has an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours.

In a still further aspect, the dosage form has a dissolution profile under the Tablet Dissolution Test characterized by less than about 5% by weight magnesium salt released at 2 hours, no more than about 40% by weight magnesium salt released at 3 hours, at least about 50% by weight magnesium salt released at 8 hours, and substantially all magnesium salt released at 12 hours.

It is understood that the disclosed methods of making can be used to provide the disclosed oral dosage forms. It is also understood that the disclosed methods of making can be used to provide oral dosage forms that can be used in connection with the disclosed methods of using. It is also understood that the disclosed methods of making can be used to provide oral dosage forms that can be employed in connection with the disclosed kits.

Using preformulation and basic prototype formulation data, it was determined that a sustained release matrix tablet produced via a wet granulation process was ideal. Furthermore, it was determined that fluid bed top spray granulation was more viable than high shear granulation techniques.

In order to keep the overall tablet weight down, minimizing the amount of excipients used was desired. Therefore, top spray granulation allowed for maximum distribution of the amount of functional excipients needed as well as providing a very uniform granule batch. High shear granulation, on the other hand, produced a non-uniform granule batch with large dense agglomerations and "balling" of the granulation blend being observed.

Prototype formulations indicate that the powder form of magnesium lactate dihydrate (API) is preferred for the top spray processes. Compaction properties of granules made from the powder form were improved from that of granules made from the granular form of magnesium lactate dihydrate. Dissolution comparison results were also favorable to the powder form. Without wishing to be bound by theory, it is believed that these characteristics are due to the contrast in particle size, and thus overall surface area, of the two forms. The powder form, having a higher overall surface area, can allow for greater particle-to-particle and particle-to-media interactions.

Typically, sustained release matrix tablets contain the active pharmaceutical ingredient (API), hydrophobic or hydrophilic drug release retardants, and other functional excipients such as binders, diluents, glidants, and lubricants. The mechanisms controlling the release of the API from the matrix include diffusion and erosion. To determine viable matrix formulations, tablets with different rate controlling excipients were explored. The release rate of magnesium from these tablets was analyzed and dissolution profiles generated and compared to that of the target profiles.

Aquacoat ECD was determined to be a good candidate for use as a hydrophobic drug release retardant. Aquacoat ECD is an aqueous dispersion of ethyl cellulose. It is typically used as a hydrophobic sustained release polymer as a coating on tablet cores. For the formulations in this study, Aquacoat ECD was applied as the granulation medium in a top spray granulation process. By doing this, Aquacoat ECD functions as both a binder (allowing granule agglomeration to occur) and a sustained release matrix excipient. Once applied, it is believed that Aquacoat ECD controls the release of magnesium by two means: by coating individual magnesium lactate particles providing a diffusion barrier as well as by creating a hydrophobic matrix within the tablet core itself, through which diffusion and erosion rates are controlled.

After multiple trials, a lead formulation was found that incorporated a disintegrant (Ac-Di-Sol) into the Aquacoat ECD platform. This lead formulation could be manipulated in order to fit both the slow and fast-targeted profiles and therefore it was further investigated. In the end, stability data concluded that the formulation was not stable, with dissolution rate greatly increasing over time (see FIG. 9).

Coinciding with the Aquacoat ECD formulation development was the development of a hydrophilic matrix system. The first excipient investigated was Methocel (hydroxypropyl methylcellulose). Methocel is water-soluble cellulose ether commonly used in hydrophilic matrix systems. Upon exposure to water, Methocel™ forms a gel layer through which drug diffusion and tablet erosion control the overall dissolution rate.

Numerous attempts were made at developing a formulation based on Methocel; however, in combination with high-sheer granulation, these formulations did not achieve desired formulation performance characteristics. Combinations of different binders with different molecular weight grades of Methocel were attempted. Results showed that dissolution was either shut down completely (below target), too fast (above target), or held on target initially but then released too fast.

The next hydrophilic polymer studied was Carbopol 974P. Carbopol 974P is a highly cross-linked polymer that produces highly viscous gels when hydrated. It is typically used at lower levels in tablet formulations, which was believed ideal for this application. Granules were produced via top spray once again, using a solution of Klucel (hydroxypropyl cellulose) as the granulation medium and extragranularly blending in Carbopol 974P. With moisture content of the formulation being a concern, both an aqueous and organic solvent-based process were developed and compared. Stability data showed promising results.

To produce the magnesium salt tablets, the following methods are typically utilized:

1. Granulation

First, the magnesium salt is granulated. In one aspect, granulation of the magnesium salt is performed in the presence of one or more liquids, for example, Klucel. In such aspects, the granulated particles comprise the magnesium salt and the one or more liquids. The magnesium salt can be one or more of the disclosed magnesium salts; however, in one aspect, the magnesium salt is a highly bioavailable magnesium salt, for example, magnesium L-lactate dihydrate. In a further aspect, the magnesium salt is characterized by low compressibility. In a further aspect, the magnesium salt is in powdered form.

Granulation typically comprises the step of fluid bed granulation of a magnesium salt. That is, the magnesium salt can be prepared by fluid bed granulation. In one aspect, the magnesium salt is prepared by wet granulation. In a further aspect, the magnesium salt is not prepared by dry granulation. Other components, for example binders, can be mixed with the magnesium salt for granulation. Typically, a Fluid Air Model 20 fluid bed with top spray granulation wand with a 1.4 mm nozzle and conical air cap is assembled, and the wand height is adjusted according to batch size. The fluid bed is then preheated to a chamber temperature of about 40° C. The magnesium salt is then charged to the fluid bed. Application of the granulation medium typically begins once fluidization has been achieved.

In one aspect, granulate is applied by "top spray," following the parameters below, increasing application rate as process equilibrates.

Airflow 20→38 SCFM
Nozzle Pressure 30 PSI
Pump Speed 10→34 RPM
Inlet Temperature 70→90° C.
Product Temperature ~28° C.
Outlet Temperature ~26° C.

After application of all granulation medium, fluidizing granulation is typically continued. In one aspect, the granules are dried in fluid the bed until LOD@90° C.≤8.0% (Product Temp 58-60° C., Outlet Temp 36-40° C.).

2. Milling

Next, the magnesium salt granules are typically sized to appropriate particle size, typically by passing through a screen and is introduced into a mixer, for example a planetary or a lodige mixer. The granulation can be calibrated through a 20 mesh (840 micron) sieve. Material that passes through the sieve is collected; any material greater than 20 mesh in size continue to further milling, typically using the following conditions:

Quadro Comil
Screen 2A062R03741
Impeller 2A1607196
Spacer Value 325
Motor Speed 10% (1315 RPM)

The further milled material can then be calibrated through a 20 mesh (840 micron) sieve and combined. Thus, in one aspect, the particles have a diameter of less than about 20 mesh (840 μm). For example, the particles can have a diameter of from about 50 μm to about 840 μm.

3. Blending

Extragranular Carbopol 974P and an equivalent amount of granulation product are passed through a 20 mesh sieve and combined with approximately one third of the remaining granulation. This material is charged to a 2 ft³ v-shell blender and blended for 2 minutes. The blend is then passed through Comil, typically using the following parameters:

Quadro Comil
Screen 2A156R03763
Impeller 2A1601173
Spacer Value 350
Motor Speed 10% (1315 RPM)

The material is then collected and combined with remaining granulation. This material is charged to a 2 ft³ v-shell blender and blended for 5 minutes. The blend is then again passed through Comil, typically using the following parameters:

Quadro Comil
Screen 2A156R03763
Impeller 2A1601173
Spacer Value 350
Motor Speed 10% (1315 RPM)

A lubricant (e.g., magnesium stearate) can then be passed with an equivalent amount of blended granulation through a 20 mesh sieve. Approximately one half of this material is typically then charged to a 2 ft³ v-shell blender and combined with the remaining granules. The combination is then typically blended for 2 minutes.

4. Compression

Typically, a tablet is formed by pressure being applied to the material to be tableted on a tablet press. A tablet press includes a lower punch which fits into a die from the bottom and an upper punch having a corresponding shape and dimension which enters the die cavity from the top after the tableting material fills the die cavity. The tablet can then be formed by pressure applied on the lower and upper punches. The ability of the material to flow freely into the die can be important in order to insure that there is a uniform filling of the die and a continuous movement of the material from the source of the material, e.g. a feeder hopper. The lubricity of the material can also be important in the preparation of the solid dosage forms, since the compressed material must be readily ejected from the punch faces.

The granulated and milled material can be then compressed into tablets using a Manesty Express 20 station D tooling press with Natoli 0.4000"×0.8750" modified oval tooling. Typical compression parameters:

Precompression ¾ Ton
Overload Pressure 6 Ton
Turret Rate 385 TPM
Feeder Rate 1216
Target Tablet Wt (g) 1.319
Tablet Wt Range (g) 1.253-1.385
Tablet Target Thickness 7.20 mm
Tablet Target Hardness 20.0 KP The term "kilopound" or "KP" refers to the weight of 1 kg of material under ambient conditions.

In one aspect, the pressure is sufficient to form a tablet having a hardness of from about 15 kp to about 30 kp, for example, from about 20 kp to about 30 kp, from about 15 kp to about 25 kp, from about 20 kp to about 25 kp, from about 15 kp to about 20 kp, from about 25 kp to about 30 kp, about 20 kp, or about 30 kp.

In one aspect, the overload pressure is from about 1 ton to about 6 tons, for example, at least about 3 tons, at least about 4 tons, at least about 5 tons, or about 6 tons.

5. Coating

A subcoat (e.g., Opadry II) can then be applied to the tablet cores using a Vector LCDS and the following parameters:

Nozzle 1.0 mm
Cap flat spray
Inlet Temp maintain outlet temp
Exhaust Temp 42-44° C.
Air Flow 18-20 CFM
Pan Speed 14-18 RPM (achieve fluid tumbling)
Pump Speed 7-14 RPM (avg 8 g/min)
Atomization 20-22 PSI An enteric coating (e.g., Eudragit L30D-55) can then be applied to the subcoated tablet cores using a Vector LCDS and the following parameters:

Nozzle 1.0 mm
Cap flat spray
Inlet Temp maintain exhaust temp
Exhaust Temp 30-33° C.
Air Flow 18-20 CFM
Pan Speed 20-26 RPM (achieve fluid tumbling)
Pump Speed 7-10 RPM (avg 6 g/min)
Atomization 20-22 PSI The tablets can then be cured in a convection oven at about 40° C. for 2 hours.

A procedure that can be employed in various aspects of making the disclosed high loading and/or controlled release oral dosage forms is tabulated in Table 1B, below.

TABLE 1B

| Procedure: |
|---|
| Granulation |

1. Assemble Fluid Air Model 20 fluid bed with top spray granulation wand with a 1.4 mm nozzle and conical air cap; adjust wand height according to batch size.
2. Preheat fluid bed to product temperature (chamber) of 40° C.
3. Charge Mg Lactate Dihydrate powder to fluid bed.
4. Begin fluidization; once fluidization has been achieved, begin application of granulation medium.
5. Top spray granulate following the parameters below, increasing application rate as process equilibrates.

Airflow 20 → 38 SCFM
Nozzle Pressure 30 PSI
Pump Speed 10 → 34 RPM
Inlet Temperature 70 → 90° C.
Product Temperature ~28° C.
Outlet Temperature ~26° C.

6. After application of all granulation medium, continue to fluidizing granulation. Dry in fluid bed until LOD @ 90° C. ≤ 8.0% (Product Temp 58-60° C., Outlet Temp 36-40° C.)

Milling

1. Calibrate granulation through a 20 mesh (840 micron) sieve.
2. Collect material that passes; any material greater than 20 mesh in size continue to milling step 3.
3. Mill > 20 mesh agglomerates using the following:

Quadro Comil
Screen 2A062R03741
Impeller 2A1607196
Spacer Value 325
Motor Speed 10% (1315 RPM) may need to increase 4. Calibrate milled granulation through a 20 mesh (840 micron) sieve and combine with granulation from step 2.

Blending

1. Pass Carbopol 974P with an equivalent amount of granulation through a 20 mesh sieve; Combine with approximately one third of the remaining granulation.
2. Charge material to 2 ft³ v-shell blender and blend for 2 minutes.
3. Pass blend from step 2 through Comil using the following parameters:

Quadro Comil
Screen 2A156R03763
Impeller 2A1601173
Spacer Value 350
Motor Speed 10% (1315 RPM)

4. Collect material and combine with remaining granulation.
5. Charge to 2 ft³ v-shell blender and blend for 5 minutes.
6. Pass material from step 5 through Comil using the same parameters as above in step 3.
7. Pass Mg Stearate with an equivalent amount of blended granulation from step 6 through a 20 mesh sieve.

TABLE 1B-continued

Procedure:

8  Charge approximately one half of material from step 6 to 2 ft³ v-shell blender, charge step 7 material to v-shell, and then charge remaining step 6 material to v-shell.
9  Blend for 2 minutes.

Compression

1  Compress tablets using Manesty Express 20 station D tooling press with Natoli 0.4000" × 0.8750" modified oval tooling.

| | |
|---|---|
| Precompression | ¾ Ton |
| Overload Pressure | 6 Ton |
| Turret Rate | 385 TPM |
| Feeder Rate | 1216 |
| Target Tablet Wt (g) | 1.319 |
| Tablet Wt Range (g) | 1.253-1.385 |
| Tablet Target Thickness | 7.20 mm |
| Tablet Target Hardness | 20.0 KP |

Coating

1  Apply Opadry II subcoat to tablet cores using Vector LCDS and the following parameters: Nozzle 1.0 mm

| | |
|---|---|
| Cap | flat spray |
| Inlet Temp | maintain outlet temp |
| Exhaust Temp | 42-44° C. |
| Air Flow | 18-20 CFM |
| Pan Speed | 14-18 RPM (achieve fluid tumbling) |
| Pump Speed | 7-14 RPM (avg 8 g/min) |
| Atomization | 20-22 PSI |

2  Apply Eudragit L30D-55 enteric coat to subcoated tablet cores using Vector LCDS and the following parameters:

| | |
|---|---|
| Nozzle | 1.0 mm |
| Cap | flat spray |
| Inlet Temp | maintain exhaust temp |
| Exhaust Temp | 30-33° C. |
| Air Flow | 18-20 CFM |
| Pan Speed | 20-26 RPM (achieve fluid tumbling) |
| Pump Speed | 7-10 RPM (avg 6 g/min) |
| Atomization | 20-22 PSI |

3  Cure tablets in convection oven at 40° C. for 2 hours.

A flowchart that summarizes a procedure that can be employed in making various aspects of the disclosed high loading and/or controlled release oral dosage forms is shown in FIG. 1.

Alternative formulations for preparing the disclosed solid oral dosage forms are summarized in Table 1C and Table 1D:

TABLE 1C

2% Carbopol 971P based formulation

Core Tablet Formula

| Compound | w/w % | mg/tablet | Supplier |
|---|---|---|---|
| Mg Lactate Dihydrate, powder | 92.15 | 1177 | Jost |
| Carbopol 971P (extragranular) | 2.00 | 25 | Lubrizol |
| Klucel EF* | 4.85 | 62 | Aqualon |
| Mg Stearate | 1.00 | 13 | Mallinckrodt |
| Tablet Total | 100.00 | 1277 | |

*applied as part of a 10% solution in DI Water

2% Sub-coated Tablet Formula

| Compound | w/w % | mg/tablet | Supplier |
|---|---|---|---|
| Opadry II Clear (85F19250) | 12.00 | 25 | Colorcon |
| DI Water | 88.00 | non-residual | In House |
| Tablet Total | 100.00 | 1302 | |

TABLE 1C-continued

6% Enteric Coated Tablet Formula

| Compound | w/w % | Solids w/w % | Mg/tablet | Supplier |
|---|---|---|---|---|
| Eudragit L30D-55 | 56.94 | 83.33 | 64 | Degussa |
| Triethyl Citrate | 2.56 | 12.50 | 10 | Morflex |
| Imwitor 900K | 0.85 | 4.17 | 3 | Sasol |
| DI Water | 39.64 | n/a | non-residual | In House |
| Tablet Total | 100.00 | 100.00 | 1379 | |

Note:
coating wt gain calculation based on core tablet weight.

TABLE 1D

10% Klucel EF & 2% Mg Stearate based formulation:

Core Tablet Formula

| Compound | w/w % | mg/tablet | Supplier |
|---|---|---|---|
| Mg Lactate Dihydrate, powder | 88.20 | 1192.38 | Jost |
| Klucel EF* | 9.80 | 132.9 | Aqualon |
| Mg Stearate | 2.00 | 27.04 | Mallinckrodt |
| Tablet Total | 100.00 | 1351.91 | |

*applied as part of a 10% solution in DI Water

2% Sub-coated Tablet Formula

| Compound | w/w % | mg/tablet | Supplier |
|---|---|---|---|
| Opadry II Clear (85F19250) | 12.00 | 27 | Colorcon |
| DI Water | 88.00 | Non-residual | In House |
| Tablet Total | 100.00 | 1378.91 | |

6% Enteric Coated Tablet Formula

| Compound | w/w % | Solids w/w % | Mg/tablet | Supplier |
|---|---|---|---|---|
| Eudragit L30D-55 | 56.94 | 83.33 | 67 | Degussa |
| Triethyl Citrate | 2.56 | 12.50 | 10 | Morflex |
| Imwitor 900K | 0.85 | 4.17 | 3 | Sasol |
| DI Water | 39.64 | n/a | non-residual | In House |
| Tablet Total | 100.00 | 100.00 | 1458.91 | |

Note:
coating wt gain calculation based on core tablet weight

The disclosed methods are capable of producing tablets which weigh between about 900 and about 1570 mgs and contain between about 8 and about 10 milliequivalents of magnesium (present as, e.g., magnesium lactate). In one aspect, the dosage form has a weight of no more than about 1500 mg. In a further aspect, the dosage form comprises a core having a weight of about 1350 mg. In a still further aspect, the dosage form has a total weight of about 1450 mg.

6. Manufacture of Medicaments

Also disclosed are methods for the manufacture of a medicament comprising an oral dosage form comprising magnesium lactate present as from about 80% to about 95% by weight of the dosage form and one or more components present as from about 5% to about 20% by weight of the dosage form.

Also disclosed are methods for the manufacture of a medicament comprising an oral dosage form comprising at least about 50% by weight of the dosage form of magnesium salt, having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours.

Also disclosed are methods for the manufacture of a medicament comprising an oral dosage form comprising at least about 50% by weight of the dosage form of a magnesium salt, having a coated core dissolution profile under the Tablet Dissolution Test characterized by less than about 5% by weight magnesium salt released at 2 hours, no more than about 40% by weight magnesium salt released at 3 hours, and at least about 50% by weight magnesium salt released at 8 hours. For example, from about 50% to about 80% by weight magnesium salt released at 8 hours. In a further aspect, substantially all magnesium salt can be released within 12 hours.

D. Methods of Using

In one aspect, the disclosure relates to methods for treating a disorder characterized by magnesium deficiency and/or for preventing or alleviating low magnesium levels. In one aspect, the methods comprise administering a therapeutically effective amount of an oral dosage form comprising a magnesium salt. In a further aspect, the magnesium salt is magnesium lactate, for example, magnesium L-lactate dihydrate.

It is contemplated that, in certain aspects, the disclosed oral dosage forms can be co-administered with calcium and/or vitamin C.

It is understood that the disclosed methods of using can employ the disclosed oral dosage forms. It is also understood that the disclosed methods of using can employ oral dosage forms provided by the disclosed methods of making. It is also understood that the disclosed methods of using can be employed in connection with the disclosed kits.

1. Treatment Methods

Studies have demonstrated that magnesium lactate is 100% effective in repleting intracellular magnesium levels to normal ranges, which is defined as a minimum concentration of 33.9 mEq/IU and can be measured by electron fluoroscopy or other scientifically acceptable means of measuring intracellular magnesium levels. Thus, in one aspect, the present disclosure relates to a method of treating a disorder characterized by magnesium deficiency comprising administering to a mammal a therapeutically effective amount of an oral dosage form comprising at least about 80% by weight of a magnesium salt, thereby treating the disorder. In a further aspect, the oral dosage form is high-loading magnesium oral dosage form; for example, the dosage form can comprise at least about 8 mEq of magnesium lactate present as from about 80% to about 95% by weight of the dosage form and one or more components present as from about 5% to about 20% by weight of the dosage form. In a further aspect, the oral dosage form is a controlled release magnesium oral dosage form; for example, the dosage form can have an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours. In a yet further aspect, the oral dosage form is a high-loading magnesium oral dosage form and a controlled release magnesium oral dosage form.

In a further aspect, the present disclosure relates to a method of treating hypomagnesemia comprising administering to a mammal a therapeutically effective amount of an oral dosage form comprising at least about 80% by weight of a magnesium salt, thereby treating the hypomagnesemia.

In a further various aspects, the magnesium salt is one or more of magnesium carbonate, magnesium chloride, magnesium citrate, magnesium fumerate, magnesium gluconate, magnesium glycinate, magnesium L-lactate, magnesium oxide, magnesium DL-aspartate, magnesium L-aspartate, magnesium hydroxide, magnesium salicylate, magnesium sulfate, magnesium aminoate, magnesium phosphate, magnesium acetate, magnesium pidolate, magnesium malate, or magnesium picolinate.

In a further various aspects, the magnesium salt is selected to be a highly bioavailable magnesium salt. Examples of such magnesium salts include magnesium lactate, magnesium DL-aspartate, and magnesium L-aspartate. In one aspect, the magnesium salt is magnesium lactate (2-hydroxypropanoic acid magnesium salt), for example, magnesium L-lactate dihydrate.

In further various aspects, the disorder is one or more of ADD/ADHD, aortic disorders, allergy, Alzheimer's, angina, anxiety disorders, arrhythmia, arthritis, asthma, autism, auto immune disorders, tooth decay, calcification of soft tissues including heart valve calcification, cerebral palsy, chemical allergy or sensitivity, chronic fatigue syndrome, coma, congestive heart disease, constipation, orthodontic disorders, depression, diabetes, eating disorders, fibromyalgia, gastroenterological disorders including ulcer, Crohn's disease, colitis, and food allergy, hearing loss, heart disease, hypertension, hypomagnesemia, hypokalemia, hypocalcemia, high blood pressure, hyperglycemia, impaired athletic performance, infantile seizure, seizure, insomnia, kidney stones, learning disorders, Lou Gehrig's disease, migraines, mitral valve prolapse, multiple sclerosis, muscle cramps, fatigue, lethargy, myopia, nystagmus, neurological disorders, obesity, osteoporosis, pectus excavatum, Parkinson's disease, PMS, dysmenorrhea, primary pulmonary hypertension, Raynaud's disease, sudden infant death syndrome, stroke, Syndrome X, insulin resistance, thyroid disorders, TMJ, or ulcerative colitis.

In one aspect, the disorder is a disorder that is typically treated with intravenous magnesium supplementation. For example, in certain aspects, the disclosed oral dosage forms can be used as a substitute for intravenous $MgSO_4$ administration. In a further aspect, the disorder is a disorder that can be treated with intravenous magnesium supplementation but is typically untreated by administration of oral magnesium dosage forms.

In a further aspect, the disorder is asthma. Studies indicate a relationship between magnesium intake and asthma symptoms. For example, the polymorphonuclear (type of white blood cell) magnesium content for patients with different types of asthma has been found to be lower than in healthy volunteers. Thus, without wishing to be bound by theory, it is believed that the reduction of polymorphonuclear magnesium content can have an important role in the pathogenesis of asthma. The bronchodilating effect of magnesium has also been reported in patients with both mild and severe asthmatic attacks. Animal studies have shown that magnesium deficiency increases the amount of histamine released into the blood. In fact, intravenous infusion of $MgSO_4$ has been shown to produce a rapid and marked bronchodilation in both mild and severe asthma and can be a unique bronchodilating agent.

In further various aspects, the magnesium salt is one or more of magnesium carbonate, magnesium chloride, magnesium citrate, magnesium fumerate, magnesium gluconate, magnesium glycinate, magnesium L-lactate, magnesium oxide, magnesium DL-aspartate, magnesium L-aspartate, magnesium hydroxide, magnesium salicylate, magnesium sulfate, magnesium aminoate, magnesium phosphate, magnesium acetate, magnesium pidolate, magnesium malate, or magnesium picolinate.

In one aspect, the amount of magnesium salt can be selected as an amount appropriate for the disorder to be treated. For example, the amount can be from about 10 mEq/IU per day to about 40 mEq/IU per day, from about 20 mEq/IU per day to about 60 mEq/IU per day, or at least about 40 mEq/IU per day. In one aspect, the amount is sufficient to restore depleted serum magnesium levels to a therapeutically acceptable level. In a further aspect, the amount is sufficient to restore depleted intracellular magnesium levels to a concentration of at least about 33.9 mEq/IU. In a further aspect, the intracellular magnesium levels are restored to a concentration of at least 33.9 mEq/IU within about 51 hours after administration.

In one aspect, the dosage form is formulated as a tablet, and the amount is two tablets, twice per day.

In one aspect, the disclosed oral magnesium dosage forms can be administered to treat a chronic disorder characterized by magnesium deficiency. In such an aspect, the oral magnesium dosage forms can help alleviate the decreased magnesium levels and/or help maintain normal magnesium levels in a patient. It is, however, understood that the administration of the disclosed oral magnesium dosage forms can, in such aspects, be required throughout the existence of the chromic disorder.

One example is the administration of the disclosed oral magnesium dosage forms to a diabetic patient. Diabetes is a chromic disorder often characterized by magnesium deficiency. Thus, while magnesium supplementation does not cure the diabetes, it can be desired to administer magnesium throughout the treatment of diabetes to maintain normal magnesium levels in the patient.

2. Co-Adminstration Methods for Drug-Induced Hypomagnesemia

Under certain circumstances, a patient can need treatment for a disorder that requires administration of a drug known to be associated with decreased magnesium levels. Administration of the drug, while possibly effective to treat the disorder, can cause low magnesium levels in the patient. It can thus be said that the patient suffers from drug-induced hypomagnesemia. A treatment for drug-induced hypomagnesemia can be a therapeutically effective amount (e.g., two tablets, twice daily) of the disclosed high-loading and/or controlled release oral dosage forms co-administered with the drug known to be associated with decreased magnesium levels. Such co-administration can alleviate the low magnesium levels in the patient.

Alternatively, a prophylactically effective amount (e.g., two tablets, twice daily) of the disclosed high-loading and/or controlled release oral dosage forms can be administered to the subject before the drug known to be associated with decreased magnesium levels, thereby preventing or alleviating the low magnesium levels. Alternatively, a therapeutically effective amount (e.g., two tablets, twice daily) of the disclosed high-loading and/or controlled release oral dosage forms can be administered to the subject after the drug known to be associated with decreased magnesium levels, thereby preventing or alleviating the low magnesium levels. In one aspect, lowered magnesium levels can extend beyond administration of the drug; it is understood that magnesium treatment can be deemed appropriate until serum magnesium levels return to a therapeutically acceptable level.

Thus, in one aspect, the disclosure relates to a method of preventing or alleviating low magnesium levels comprising co-administering to a mammal a therapeutically effective amount of an oral dosage form comprising at least about 80% by weight of a magnesium salt and a drug having a known side-effect of decreasing magnesium levels (e.g., serum levels or intracellular levels), thereby preventing or alleviating the low magnesium levels. In a further aspect, the drug has a known side effect of decreasing magnesium serum levels. The low magnesium levels can constitute hypomagnesemia.

In a further aspect, the drug is a diuretic, an immunosuppressant, a chemotherapeutic agent, an antibiotic, a corticosteroid, an aldosterone agonist, an insulin-antagonist, an adrenergic antagonist, or any drug that causes renal magnesium losses, including the following general categories: (1) loop active and thiazide diuretics, (2) nephrotoxins, including amino glycoside antibiotics, immunosupressants, chemotherapeutics, and amphotericin B, and (3) treatments that increase magnesium losses from cells, thereby leading to renal magnesium losses.

While the disclosed magnesium compositions are oral dosage forms, the drug known to be associated with decreased magnesium levels can be a tablet, a capsule, a gel, an ingestible liquid, a powder, a patch, or an intravenous injection.

In one aspect, the disclosed oral magnesium dosage forms can be co-administered along with a drug to treat a chronic disorder, wherein administration of the drug can lead to magnesium deficiency. In such an aspect, the oral magnesium dosage forms can help alleviate the decreased magnesium levels and/or help maintain normal magnesium levels in a patient. It is, however, understood that the administration of the disclosed oral magnesium dosage forms can, in such aspects, be required throughout the existence of the chromic disorder.

One example is the co-administration of the disclosed oral magnesium dosage forms with loop diuretics. Loop diuretics are often used to treat hypertension or edema due to congestive heart failure or renal insufficiency, but can result in hypokalemia and/or hypomagnesemia. Thus, while magnesium supplementation does not necessarily cure the hypertension, congestive heart failure, or renal insufficiency, it can be desired to co-administer magnesium to maintain normal magnesium levels in a patient.

3. Co-Adminstration Methods for Disease-Induced Hypomagnesemia

Under certain circumstances, a patient can need treatment for a disorder associated with decreased magnesium levels. Treatment can include administration of a drug known to be effective for treating the disorder, but ineffective in preventing or alleviating the decreased magnesium levels. It can thus be said that the patient suffers from disease-induced hypomagnesemia. A treatment for disease-induced hypomagnesemia can be a therapeutically effective amount (e.g., two tablets, twice daily) of the disclosed high-loading and/or controlled release oral dosage forms co-administered with the drug known to be effective for treating the disorder. Such co-administration can alleviate the low magnesium levels in the patient.

Alternatively, a prophylactically effective amount (e.g., two tablets, twice daily) of the disclosed high-loading and/or controlled release oral dosage forms can be administered to the subject before the treatment regimen, thereby preventing or alleviating the low magnesium levels. Alternatively, a therapeutically effective amount (e.g., two tablets, twice daily) of the disclosed high-loading and/or controlled release oral dosage forms can be administered to the subject after the treatment regimen, thereby preventing or alleviating the low magnesium levels. In one aspect, lowered magnesium levels can extend beyond treatment of the disorder; it is understood that magnesium treatment can be deemed appropriate until serum magnesium levels return to a therapeutically acceptable level.

Thus, in one aspect, the present disclosure relates to a method of preventing or alleviating low magnesium levels comprising co-administering to a mammal a therapeutically effective amount of an oral dosage form comprising at least about 80% by weight of a magnesium salt and a drug known to treat a disorder associated with decreasing intracellular magnesium levels, thereby preventing or alleviating the low magnesium levels. In a further aspect, the disorder is associated with decreasing magnesium serum levels. The low magnesium levels can constitute hypomagnesemia.

In a further aspect, the drug known to treat a disorder associated with decreasing intracellular magnesium levels can be any drug known to those of skill in the art (e.g., a physician or veterinarian) that can be used with patients having a disorder that is correlated with hypomagnesemia; that is, a causal relationship between the disorder and hypomagnesemia may or may not exist. In various aspects, the drug known to treat a disorder associated with decreasing intracellular magnesium levels is a diuretic, an immunosuppressant, a chemotherapeutic agent, or an antibiotic. In one aspect, the drug administered to treat the disorder does not treat the magnesia.

While the disclosed magnesium compositions are oral dosage forms, the drug known to be associated with decreased magnesium levels can be a tablet, a capsule, a gel, an ingestible liquid, a powder, a patch, or an intravenous injection.

In a further aspect, the disorder is one or more of ADD/ADHD, aortic disorders, allergy, Alzheimer's, angina, anxiety disorders, arrhythmia, arthritis, asthma, autism, auto immune disorders, tooth decay, calcification of soft tissues including heart valve calcification, cerebral palsy, chemical allergy or sensitivity, chronic fatigue syndrome, coma, congestive heart disease, constipation, orthodontic disorders, depression, diabetes, eating disorders, fibromyalgia, gastroenterological disorders including ulcer, Crohn's disease, colitis, and food allergy, hearing loss, heart disease, hypertension, hypomagnesemia, hypokalemia, hypocalcemia, high blood pressure, hyperglycemia, impaired athletic performance, infantile seizure, seizure, insomnia, kidney stones, learning disorders, Lou Gehrig's disease, migraines, mitral valve prolapse, multiple sclerosis, muscle cramps, fatigue, lethargy, myopia, nystagmus, neurological disorders, obesity, osteoporosis, pectus excavatum, Parkinson's disease, PMS, dysmenorrhea, primary pulmonary hypertension, Raynaud's disease, sudden infant death syndrome, stroke, Syndrome X, insulin resistance, thyroid disorders, TMJ, or ulcerative colitis.

Also disclosed are uses of an oral dosage form comprising magnesium lactate present as from about 80% to about 95% by weight of the dosage form and one or more components present as from about 5% to about 20% by weight of the dosage form.

Also disclosed are uses of an oral dosage form comprising at least about 50% by weight of the dosage form of a magnesium salt, having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours.

Also disclosed are uses of an oral dosage form comprising at least about 50% by weight of the dosage form of a magnesium salt, having a coated core dissolution profile under the Tablet Dissolution Test characterized by less than about 5% by weight magnesium salt released at 2 hours, no more than about 40% by weight magnesium salt released at 3 hours, and at least about 50% by weight magnesium salt released at 8 hours. For example, from about 50% to about 80% by weight magnesium salt released at 8 hours. In a further aspect, substantially all magnesium salt can be released within 12 hours.

In one aspect, the disclosed oral magnesium dosage forms can be co-administered along with a drug to treat a chronic disorder characterized by magnesium deficiency. In such an aspect, the oral magnesium dosage forms can help alleviate the decreased magnesium levels and/or help maintain normal magnesium levels in a patient. It is, however, understood that the administration of the disclosed oral magnesium dosage forms can, in such aspects, be required throughout the existence of the chronic disorder.

One example is the co-administration of the disclosed oral magnesium dosage forms with insulin to a diabetic patient. Diabetes is a chronic disorder often characterized by magnesium deficiency. Thus, while magnesium supplementation does not cure the diabetes, it can be desired to co-administer magnesium throughout the treatment of diabetes to maintain normal magnesium levels in the patient.

E. Kits

In a further aspect, the present disclosure also relates to a kit comprising an oral dosage form comprising at least about 80% by weight of a magnesium salt and a drug having a known side-effect of decreasing intracellular magnesium levels. In one aspect, the magnesium salt comprises a highly bioavailable magnesium salt, for example, magnesium L-lactate dihydrate.

In a further aspect, the present disclosure also relates to a kit comprising an oral dosage form comprising at least about 80% by weight of a magnesium salt and a drug known to treat a disorder associated with decreasing intracellular magnesium levels. In one aspect, the magnesium salt comprises a highly bioavailable magnesium salt, for example, magnesium L-lactate dihydrate.

The kits can comprise magnesium oral dosage forms co-packaged, co-formulated, and/or co-delivered with other components. For example, a drug manufacturer, a drug reseller, a physician, or a pharmacist can provide a kit comprising a disclosed oral dosage forms and another component for delivery to a patient.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the present disclosure and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Measurement of Dissolution Profile

The dissolution profile of a disclosed controlled release dosage form can be measured by the Tablet Dissolution Test, a procedure analogous to the USP <711> Dissolution Test, as described herein.

First, 0.1N HCl dissolution media is prepared. For each liter of media, 8.33 mLs of concentrated hydrochloric acid is diluted to 1 liter with deionized (DI) water. This solution is mixed well before using. It is understood that this solution can be scaled up or down in volume, depending on the amount needed.

$$0.1N\ HCl \Rightarrow \frac{0.1\ mols/L}{121\ mols} = 0.00833\ L$$

Second, 50 mM citrate buffer dissolution media is prepared. For each liter of media, 14.7045 g of sodium citrate dihydrate (m.w. 294.09 g/mol) is dissolved in 1 liter DI water. This is mixed well before use, making sure that all the sodium citrate has dissolved before adjusting the pH.

$$50\ mM\ Citrate\ buffer = 294.09\ g/mol * 0.05\ mols/L * 1\ L$$

During stirring, the pH is then adjusted to 6.8+/−0.05 pH units, using concentrated hydrochloric acid. The pH is monitored and adjusted further, if necessary, while the solution is allowed to stir for at least 30 minutes.

Third, the dissolution test is performed (per USP <711>). For delayed release formulations (e.g., enteric coated tablets) only, a first stage is performed. One liter of 0.1N hydrochloric acid is placed in a dissolution vessel, which is then covered. The temperature is then stabilized at 37° C.±0.5° C. The temperature is recorded, and one tablet is placed in the vessel. The solution is stirred using a paddle rate of 50 rpm. After two hours, an aliquot of the media is withdrawn for testing, and the tablet is removed. In the second stage, one liter of 50 mM citrate buffer (pH=6.8) is placed in a dissolution vessel, which is then covered. The temperature is then stabilized at 37° C.±0.5° C. The temperature is recorded, and one tablet is placed in the vessel. The solution is stirred using a paddle rate of 50 rpm. At either one-hour intervals (e.g., after 1, 2, 3, 4, 5, 6, 7, 8, 9, and 10 hours) or at two-hour intervals (e.g., after 2, 4, 6, 8, and 10 hours), an aliquot of the media is withdrawn for testing. After 12 hours total, the sample tablet is homogenized in the media. After the solution has equilibrated, an aliquot is withdrawn for testing.

Fourth, aliquots are tested by atomic absorption analysis. A two-step dilution of each sample is used to attain the desired concentration. While a dilution factor of 100 is used, it is understood that dilution factor can be varied to accommodate a change in operating parameters (e.g., concentration). One 1 mL of the dissolution sample is diluted to 10 mL total of 0.1N hydrochloric acid. The diluted sample is mixed well before continuing. After the sample is allowed to rest for one hour, it is filtered through a 0.45 um PVDF syringe filter to remove any polymerized excipients. One mL of the filtered sample is then diluted to 10 mL total with 1.2% lanthanum oxide diluent. The working sample is mixed well before analysis. The sample set is bracketed by standards during the analysis. Typically, no more than thirty-six samples are tested between standard sets.

The slope and intercept are calculated for each set of standards, and then the bracketing values are averaged. The sample concentrations are then determined using the intercept and slope of the averaged standards and the absorbance of the sample:

$$Conc = \frac{(Abs - intercept) \times Dil.\ Factor}{slope}$$

To determine a dissolution profile for a coated tablet, both an acidic stage and a buffer stage are employed. In the absence of a coating, the acidic stage can be unnecessary. Thus, to determine an uncoated core dissolution profile, only the buffer stage is typically employed.

2. Preparation of Tablets (Lots 2007-124-3 & 2007-124-20-A)

Tablet cores were prepared by wet granulation of Mg Lactate with Aquacoat ECD/TEC dispersion via top spray process in a fluid bed. Both powdered and granular forms of magnesium lactate were used, as shown in Table 2. Both forms of Mg Lactate were granulated in the same way.

TABLE 2

Composition of Tablet Cores, Lots 2007-124-3 & 2007-124-20-A

| Component | % (w/w) | |
|---|---|---|
| | 2007-124-3 | 2007-124-20-A |
| Mg Lactate Dihydrate, powder | 88.3 | |
| Mg Lactate Dihydrate, granular | | 88.3 |
| Aquacoat ECD | 9.1 | 9.1 |
| TEC | 2.2 | 2.2 |
| Mg Stearate, veg source | 0.5 | 0.5 |
| Total | 100.1 | 100.1 |

Next, granules were dried via fluid bed. The granules were then calibrated/milled to ≤20 mesh size. Magnesium stearate was then blended with the granules with a V-shell blender. The final blend was then compressed into tablets using 0.4000"×0.8750" modified oval tooling, at a target hardness of approximately 20 kp. A Eudragit L30D-55 enteric coat (Lot 2007-124-3) was then applied. Next, an Opadry Clear subcoat and Eudragit L30D-55 enteric coat (Lot 2007-124-20-A).

In this example, the powder form allowed for a slightly faster dissolution rate, as well as better tablet hardness than that of the granular form. Without wishing to be bound by theory, it is believed that these results were due to the fact that the powder form provided a greater overall surface area and therefore increased particle to particle and particle to solution interaction, when compared to that of the granular form.

Figure 2:
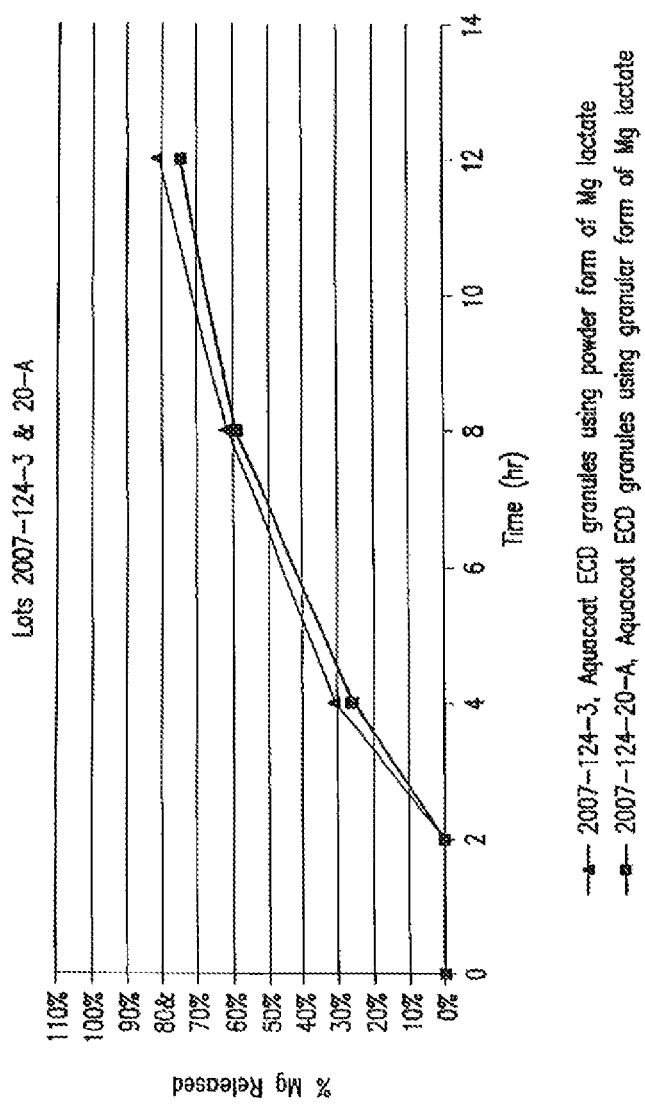
FIG. 2 shows the dissolution profile of $Mg^{2+}$ from Enteric Coated Cores (Lots 2007-124-3 & 2007-124-20-A) based on Top Spray Granulation with Aquacoat® ECD.

The tablets were tested under the Tablet Dissolution Test. The results are shown in FIG. 2.

3. Preparation of Tablets (Lots 2007-124-30 & 34)

Tablet cores were prepared by wet granulation of Mg Lactate with Aquacoat ECD/TEC dispersion via top spray process in fluid bed. Tablets were prepared both with and without disintegrant, as shown in Table 3.

TABLE 3

Composition of Tablet Cores, Lots 2007-124-30 & 34

| Component | 2007-124-30 (% (w/w)) | 2007-124-34 (% (w/w)) |
|---|---|---|
| Mg Lactate Dihydrate, powder | 87.81 | 83.38 |
| Aquacoat ECD | 9.01 | 8.55 |
| TEC | 2.18 | 2.07 |
| Ac-Di-Sol | | 5.00 |
| Mg Stearate, veg source | 1.00 | 1.00 |
| Total | 100.00 | 100.00 |

Next, granules were dried via fluid bed. The granules were then calibrated/milled to ≤20 mesh size. Disintegrant (Ac-Di-Sol) and magnesium stearate were then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied.

Figure 3:
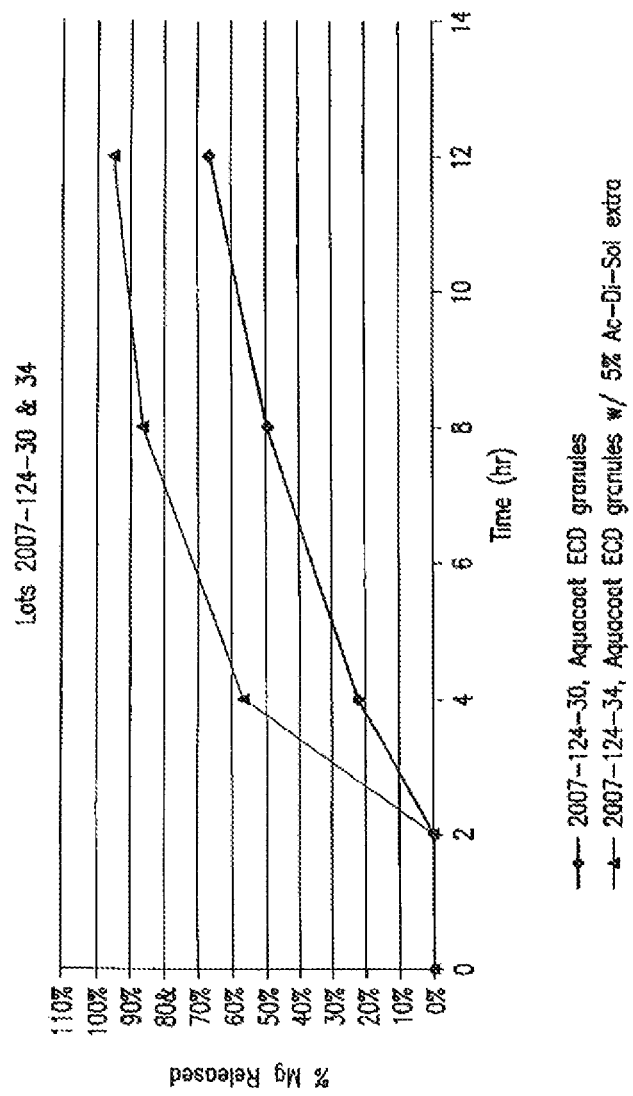
FIG. 3 shows the dissolution profile of $Mg^{2+}$ from Enteric Coated Cores (Lots 2007-124-30 & 34) based on Aquacoat® ECD and 5% Extragranular Ac-Di-Sol®.

The tablets were tested under the Tablet Dissolution Test. The results are shown in FIG. 3. Tablets made from Aquacoat ECD granulation alone show a slow dissolution profile. By adding 5% Ac-Di-Sol (a disintegrant) to the formulation, an increased release rate was achieved. Without wishing to be bound by theory, it is believed that the increased uptake of dissolution medium and swelling of the tablet core achieved by the disintegrant, promoted the increased magnesium release rate.

4. Preparation of Tablets (Lots 2007-124-44-A, B & C)

Methocel K4M CR was geometric blended into Mg Lactate using Comil. Tablet cores were prepared by wet granulation of Mg Lactate with aqueous Kollidon 30 solution via top spray process in fluid bed, as shown in Table 4.

TABLE 4

Composition of Tablet Cores, Lots 2007-124-44-A, B & C

| | % (w/w) | | |
| --- | --- | --- | --- |
| Component | 2007-124-44-A | 2007-124-44-B | 2007-124-44-C |
| Mg Lactate Dihydrate, powder | 87.92 | 85.69 | 83.45 |
| Methocel K4M CR | 4.73 | 7.11 | 9.49 |
| Kollidon 30 | 5.85 | 5.70 | 5.55 |
| Mg Stearate, veg source | 1.50 | 1.50 | 1.50 |
| Total | 100.00 | 100.00 | 99.99 |

Next, granules were dried via fluid bed. The granules were then calibrated/milled to ≤20 mesh size. Extragranular Methocel K4M CR and Mg Stearate were then blended with the granules with a V-shell blender. The final blend was then compressed into tablets using 0.4000"×0.8750" modified oval tooling, at a target hardness of approximately 30 kp. Opadry Clear subcoat and Eudragit L30D-55 enteric coat were then applied.

Figure 4:
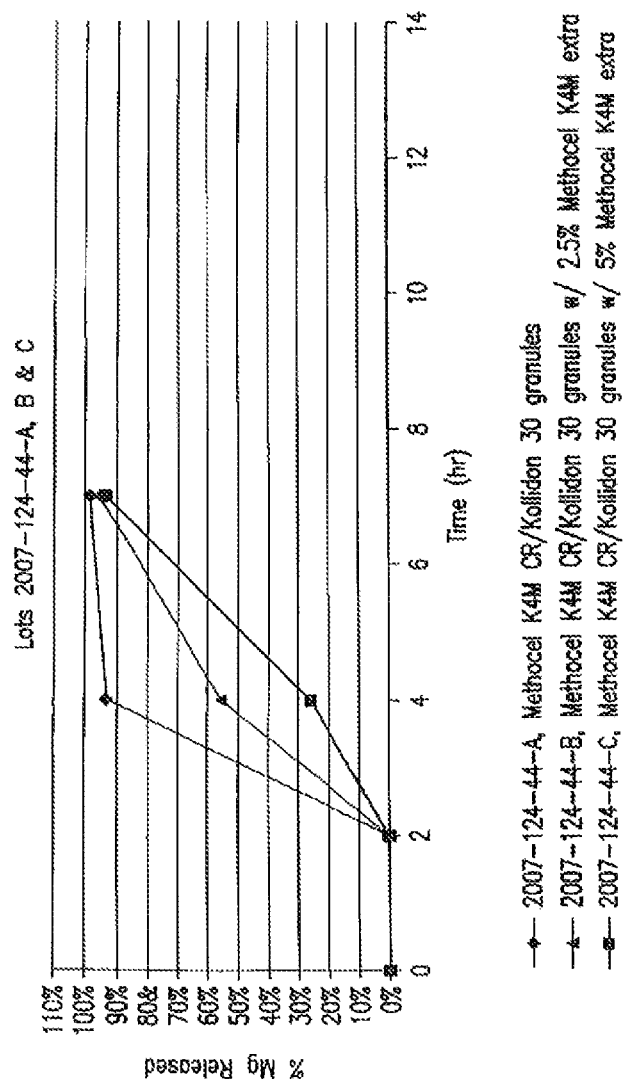
FIG. 4 shows the dissolution profile of $Mg^{2+}$ from Enteric Coated Cores (Lots 2007-124-44-A, B & C) based on Methocel K4M CR and Kollidon 30.

The tablets were tested under the Tablet Dissolution Test. The results are shown in FIG. 4. Dissolution results show that as the level of Methocel K4M CR increases, dissolution is retarded initially, but is not controlled throughout, and mostly all of the magnesium is released after 7 hours.

5. Preparation of Tablets (Lots 2007-124-56-A, B, C & D)

Methocel K4M CR was geometric blended into Mg Lactate using Comil. Tablet cores were prepared by wet granulation of Mg Lactate with aqueous Kollidon 30 solution via top spray process in fluid bed, as shown in Table 5.

TABLE 5

Composition of Tablet Cores, Lots 2007-124-56-A, B, C & D

| | % (w/w) | | | |
| --- | --- | --- | --- | --- |
| Component | 2007-124-56-A | 2007-124-56-B | 2007-124-56-C | 2007-124-56-D |
| Mg Lactate Dihydrate, powder | 85.69 | 83.46 | 85.69 | 83.46 |
| Methocel K4M CR | 4.62 | 4.50 | 4.62 | 4.50 |
| Kollidon 30 | 5.70 | 5.55 | 5.70 | 5.55 |
| Methocel K15M CR | 2.50 | 5.00 | | |
| Methocel K100M CR | | | 2.50 | 5.00 |
| Mg Stearate, veg source | 1.50 | 1.50 | 1.50 | 1.50 |
| Total | 100.01 | 100.01 | 100.01 | 100.01 |

Next, granules were dried via fluid bed. The granules were then calibrated/milled to ≤20 mesh size. Extragranular Methocel K4M CR and Mg Stearate were then blended with the granules with a V-shell blender. The final blend was then compressed into tablets using 0.4000"×0.8750" modified oval tooling, at a target hardness of approximately 30 kp. Opadry Clear subcoat and Eudragit L30D-55 enteric coat were then applied.

Figure 5:
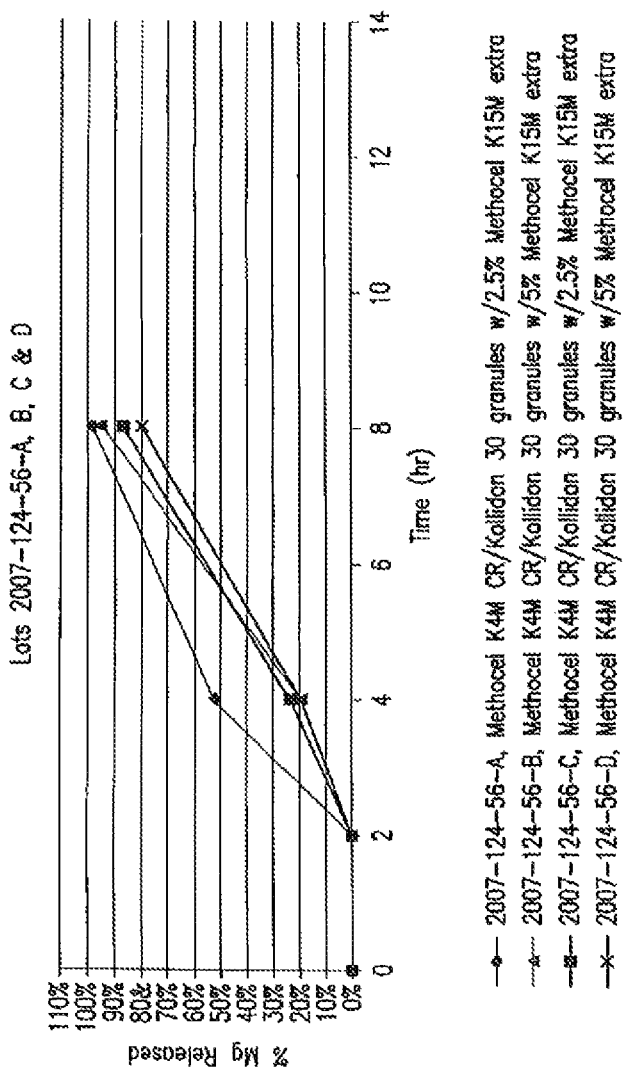
FIG. 5 shows the dissolution profile of $Mg^{2+}$ from Enteric Coated Cores (Lots 2007-124-56-A, B, C & D) based on Methocel K4M CR and Kollidon 30 with Extragranular Methocel K15M.

The tablets were tested under the Tablet Dissolution Test. The results are shown in FIG. 5. As in Lots 2007-124-44-A, B & C, dissolution is retarded initially, but is not sustained for any longer than 8 hours.

6. Preparation of Tablets (Lots 2007-124-56-E, F & G)

Tablet cores were prepared by wet granulation of Mg Lactate with Aquacoat ECD/TEC dispersion via top spray process in fluid bed. Tablets were prepared both with and without disintegrant, as shown in Table 6.

TABLE 6

Composition of Tablet Cores, Lots 2007-124-56-E, F & G

| | % (w/w) | | |
| --- | --- | --- | --- |
| Component | 2007-124-56-E | 2007-124-56-F | 2007-124-56-G |
| Mg Lactate Dihydrate, powder | 86.93 | 86.04 | 85.15 |
| Aquacoat ECD | 8.92 | 8.83 | 8.74 |
| TEC | 2.16 | 2.13 | 2.11 |
| Ac-Di-Sol | 1.00 | 2.00 | 3.00 |
| Mg Stearate, veg source | 1.00 | 1.00 | 1.00 |
| Total | 100.00 | 100.00 | 100.00 |

Next, granules were dried via fluid bed. The granules were then calibrated/milled to ≤20 mesh size. Disintegrant (Ac-Di-Sol) and magnesium stearate were then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied.

Figure 6:
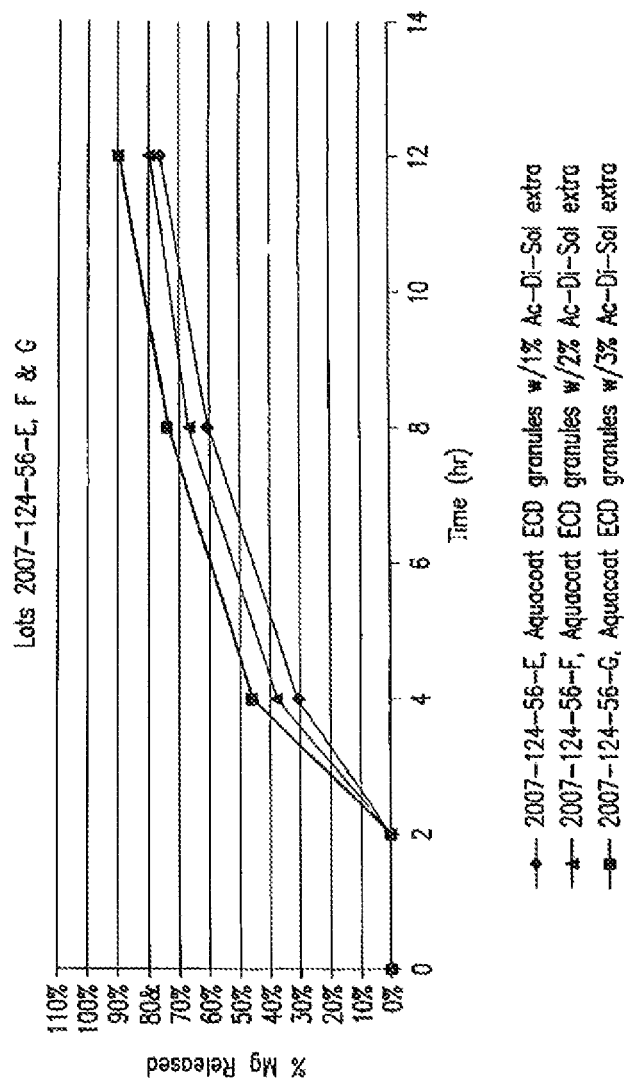
FIG. 6 shows the dissolution profile of $Mg^{2+}$ from Enteric Coated Cores (Lots 2007-124-56-E, F & G) based on Aquacoat ECD and Extragranular Ac-Di-Sol.

The tablets were tested under the Tablet Dissolution Test. The results are shown in FIG. 6. As in Lot 2007-124-34, increasing Ac-Di-Sol content in the formulation provided for a graduated increase in dissolution at each time point.

7. Preparation of Tablets (Lots 2007-124-68-A, C & D)

Methocel K4M CR was geometric blended into Mg Lactate using Comil. Tablet cores were prepared by wet granulation of Mg Lactate with aqueous Methocel E5P solution via top spray process in fluid bed, as shown in Table 7.

TABLE 7

Composition of Tablet Cores, Lots 2007-124-68-A, C & D

| | % (w/w) | | |
|---|---|---|---|
| Component | 2007-124-68-A | 2007-124-68-C | 2007-124-68-D |
| Mg Lactate Dihydrate, powder | 91.63 | 87.91 | 84.19 |
| Methocel K4M CR | 4.94 | 4.73 | 4.53 |
| Methocel E5P | 1.93 | 1.85 | 1.77 |
| Methocel K4M CR, extragranular | | 4.00 | 8.00 |
| Mg Stearate, veg source | 1.50 | 1.50 | 1.50 |
| Total | 100.00 | 99.99 | 99.99 |

Figure 7:
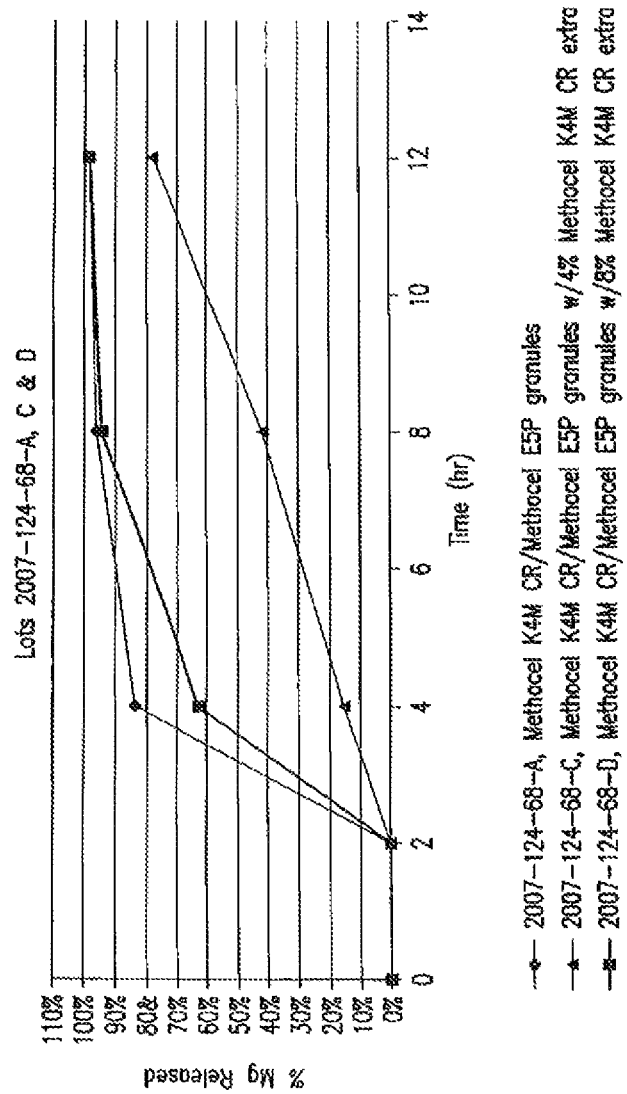
FIG. 7 shows the dissolution profile of $Mg^{2+}$ from Enteric Coated Cores (Lots 2007-124-68-A, C & D) based on Methocel K4M CR and Methocel E5P with Extragranular Methocel K4M CR.

Next, granules were dried via fluid bed. The granules were then calibrated/milled to ≤20 mesh size. Extragranular Methocel K4M CR and Mg Stearate were then blended with the granules with a V-shell blender. The final blend was then compressed into tablets using 0.4000"×0.8750" modified oval tooling, at a target hardness of approximately 30 kp. Opadry Clear subcoat and Eudragit L30D-55 enteric coat were then applied. The tablets were tested under the Tablet Dissolution Test. The results are shown in FIG. 7.

8. Preparation of Tablets (Lots 2007-124-68-B, E & F)

Methocel K15M CR was geometric blended into Mg Lactate using Comil. Tablet cores were prepared by wet granulation of Mg Lactate with aqueous Methocel E5P solution via top spray process in fluid bed, as shown in Table 8.

TABLE 8

Composition of Tablet Cores, Lots 2007-124-68-B, E&F

| | % (w/w) | | |
|---|---|---|---|
| Component | 2007-124-68-B | 2007-124-68-E | 2007-124-68-F |
| Mg Lactate Dihydrate, powder | 91.63 | 87.91 | 84.19 |
| Methocel K15M CR | 4.94 | 4.73 | 4.53 |
| Methocel K15M CR, extragranular | | 4 | 8 |
| Mg Stearate, veg source | 1.5 | 1.5 | 1.5 |
| Total | 100 | 99.99 | 99.99 |

Figure 8:
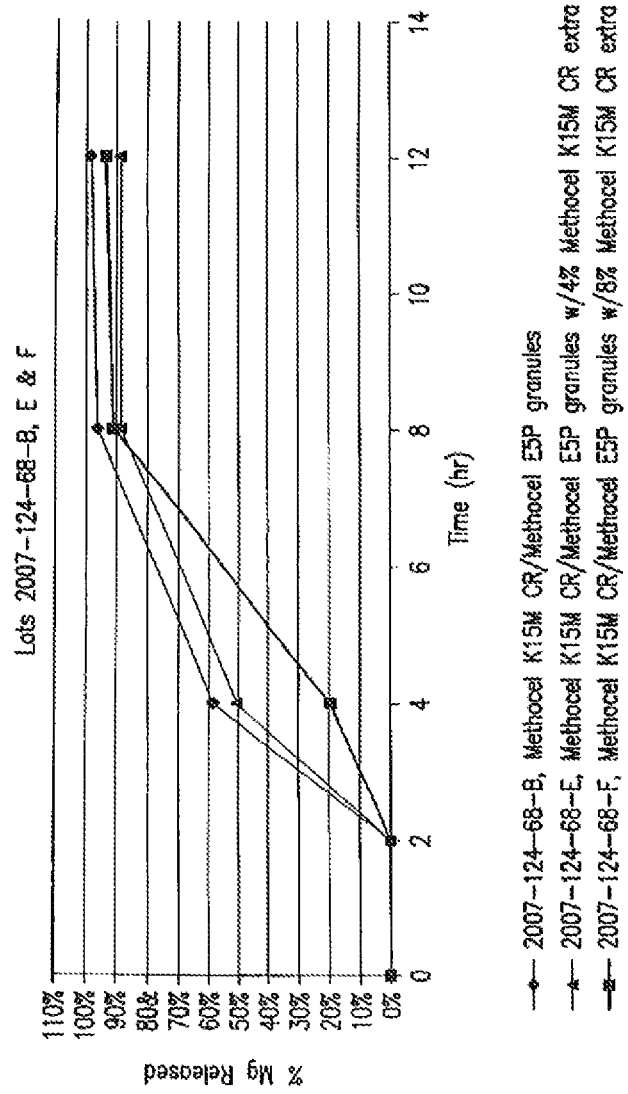
FIG. 8 shows the dissolution profile of $Mg^{2+}$ from Enteric Coated Cores (Lots 2007-124-68-B, E & F) based on Methocel K15M CR and Methocel E5P with Extragranular Methocel K15M CR.

Next, granules were dried via fluid bed. The granules were then calibrated/milled to ≤20 mesh size. Extragranular Methocel K15M CR and Mg Stearate were then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied. The tablets were tested under the Tablet Dissolution Test. The results are shown in FIG. 8.

9. Preparation of Tablets (Lot 2007-124-79-C)

Tablet cores were prepared by wet granulation of Mg Lactate with Aquacoat ECD/TEC dispersion via top spray process in fluid bed. Tablets were prepared both with and without disintegrant, as shown in Table 9.

TABLE 9

Composition of Tablet Core, Lot 2007-124-79-C

| Component | % (w/w) 2007-124-79-C |
|---|---|
| Mg Lactate Dihydrate, powder | 86.04 |
| Aquacoat ECD | 8.83 |
| TEC | 2.13 |
| Ac-Di-Sol | 2.00 |
| Mg Stearate, veg source | 1.00 |
| Total | 100.00 |

Next, granules were dried via fluid bed. The granules were then calibrated/milled to ≤20 mesh size. Disintegrant (Ac-Di-Sol) and magnesium stearate were then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied.

Figure 9:
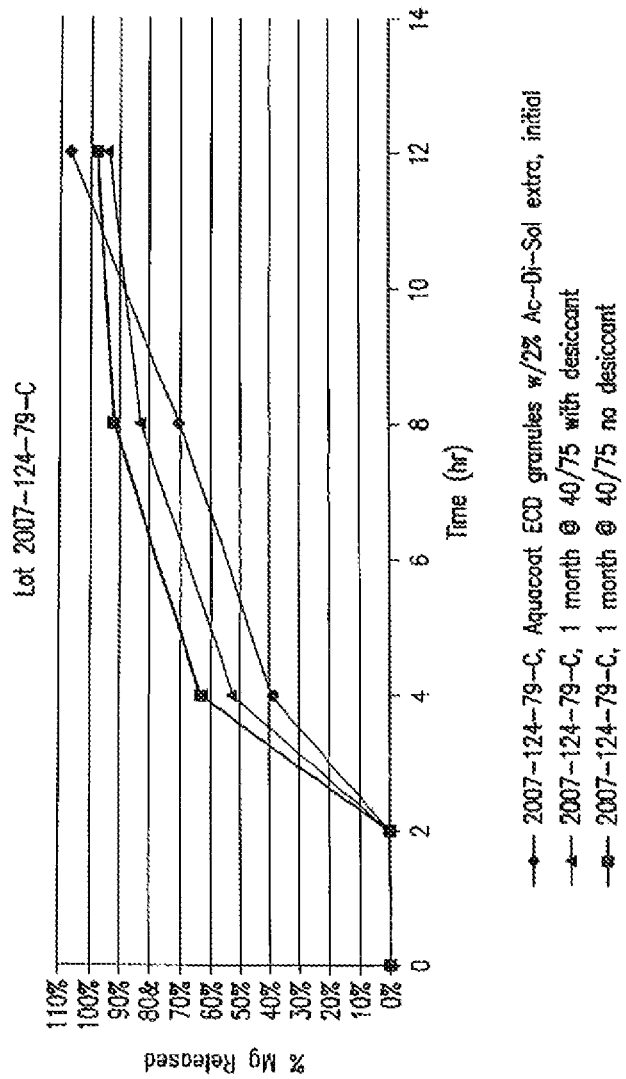
FIG. 9 shows the dissolution profile of $Mg^{2+}$ from Enteric Coated Cores (Lot 2007-124-79-C) based on Aquacoat ECD and Extragranular Ac-Di-Sol.

The tablets were tested under the Tablet Dissolution Test. The results are shown in FIG. 9. Dissolution rate increases over time.

10. Preparation of Tablets (Lots 2007-149-6-G & H)

Methocel K4M CR was geometric blended into Mg Lactate using Comil. Tablet cores were prepared by wet granulation of Mg Lactate with aqueous Methocel E5P solution via top spray process in fluid bed, as shown in Table 10.

TABLE 10

Composition of Tablet Cores, Lots 2007-149-6-G & H

| Component | 2007-149-6-G (% (w/w)) | 2007-149-6-H (% (w/w)) |
|---|---|---|
| Mg Lactate Dihydrate, powder | 87.81 | 84.19 |
| Methocel K4M CR | 4.73 | 4.53 |
| Methocel E5P | 1.85 | 1.77 |
| Methocel K100M CR, extragranular | 4.00 | 8.00 |
| Mg Stearate, veg source | 1.50 | 1.50 |
| Total | 99.99 | 99.99 |

Figure 10:
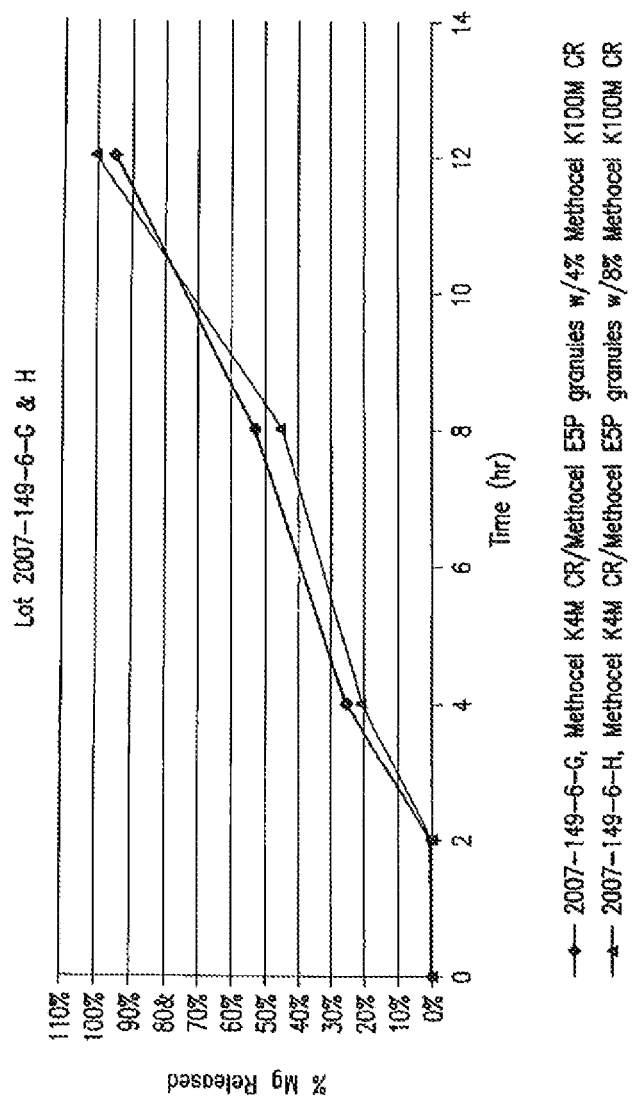
FIG. 10 shows the dissolution profile of $Mg^{2+}$ from Enteric Coated Cores (Lots 2007-149-6-G & H) based on Methocel K4M CR and Methocel E5P with Extragranular Methocel K100M CR.

Next, granules were dried via fluid bed. The granules were then calibrated/milled to ≤20 mesh size. Extragranular Methocel K100M CR and Mg Stearate were then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied. The tablets were tested under the Tablet Dissolution Test. The results are shown in FIG. 10.

11. Preparation of Tablets (Lots 2007-149-30-A, B, C & D)

Methocel K15M CR was geometric blended into Mg Lactate using Comil. Tablet cores were prepared by wet granulation of Mg Lactate with aqueous Methocel E5P solution via top spray process in fluid bed, as shown in Table 11.

TABLE 11

Composition of Tablet Cores, Lots 2007-149-30-A, B, C & D

| Component | 2007-149-30-A (% (w/w)) | 2007-149-30-B (% (w/w)) | 2007-149-30-C (% (w/w)) | 2007-149-30-D (% (w/w)) |
|---|---|---|---|---|
| Mg Lactate Dihydrate, powder | 87.50 | 81.50 | 83.06 | 80.39 |
| Methocel K15M CR | 9.00 | 15.00 | 8.54 | 8.27 |
| Methocel E5P | 2.00 | 2.00 | 1.90 | 1.84 |
| Carbopol 974P, extragranular | | | 5.00 | 8.00 |
| Mg Stearate, veg source | 1.50 | 1.50 | 1.50 | 1.50 |
| Total | 100.00 | 100.00 | 100.00 | 100.00 |

Figure 11:
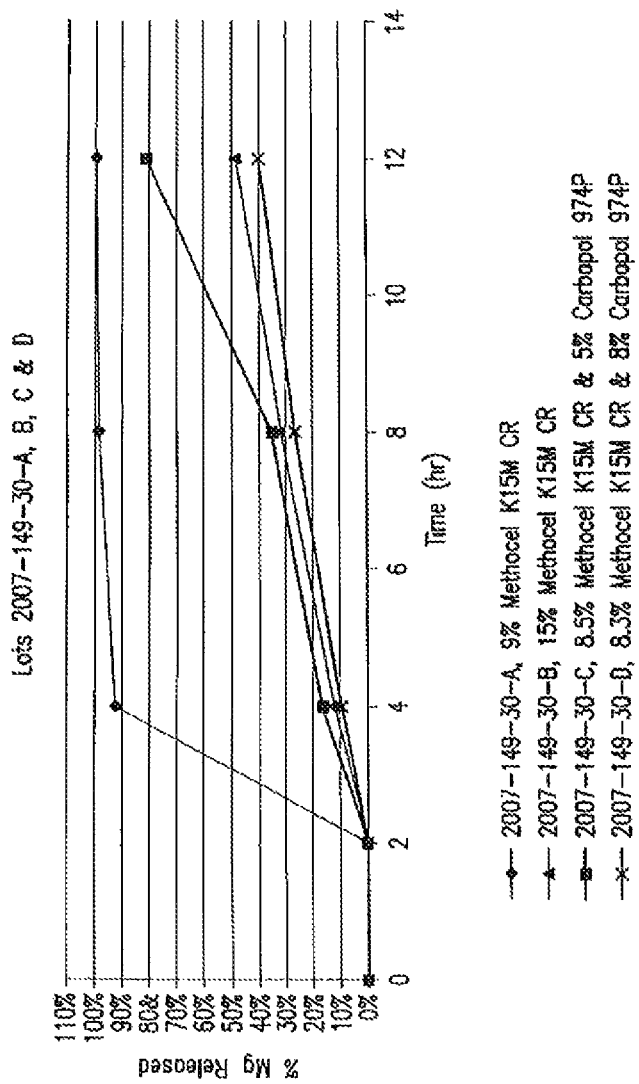
FIG. 11 shows the dissolution profile of $Mg^{2+}$ from Enteric Coated Cores (Lots 2007-149-30-A, B, C & D) based on Methocel K15M CR and Methocel E5P with Carbopol.

Next, granules were dried via fluid bed. The granules were then calibrated/milled to ≤20 mesh size. Extragranular Carbopol 974P and Mg Stearate were then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied. The tablets were tested under the Tablet Dissolution Test. The results are shown in FIG. 11.

12. Preparation of Tablets (Lots 2007-149-32, 34 & 36)

Magnesium lactate, Carbopol 974P, and intragranular Klucel EF were charged into a high shear mixer. The wet granulate Mg Lactate was then high-shear blended with Klucel EF in isopropyl alcohol solution, as shown in Table 12.

TABLE 12

Composition of Tablet Cores, Lots 2007-149-32, 34 & 36

| | % (w/w) | | |
|---|---|---|---|
| Component | 2007-149-32 | 2007-149-34 | 2007-149-36 |
| Mg Lactate Dihydrate, powder | 91.00 | 89.00 | 86.00 |
| Carbopol 974P | 3.00 | 5.00 | 8.00 |
| Klucel EF | 2.00 | 2.00 | 2.00 |
| Klucel EF, intragranular | 3.00 | 3.00 | 3.00 |
| Mg Stearate, veg source | 1.00 | 1.00 | 1.00 |
| Total | 100.00 | 100.00 | 100.00 |

Figure 12:
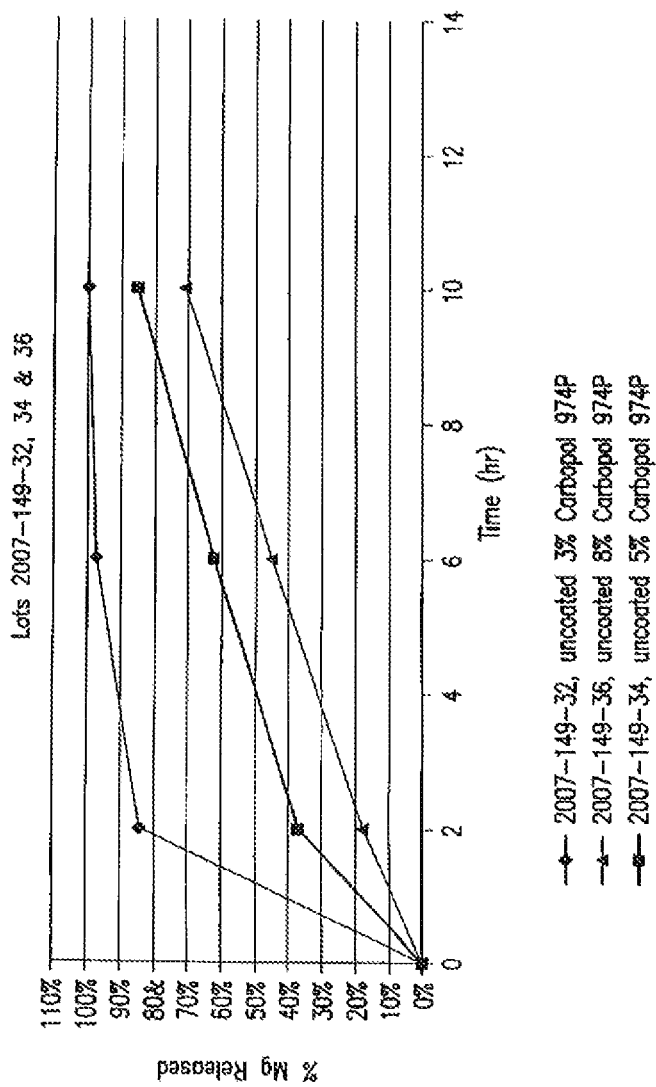
FIG. 12 shows the dissolution profile of $Mg^{2+}$ from Uncoated Cores (Lots 2007-149-32, 34 & 36) based on Klucel EF and Carbopol 974P.

Next, granules were dried via convection oven. The granules were then calibrated/milled to ≤20 mesh size. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 12. Without wishing to be bound by theory, it is believed that higher levels of Carbopol 974P decrease the dissolution rate.

13. Preparation of Tablets (Lot 2007-149-39)

Tablet cores were prepared by wet granulation of Mg Lactate with aqueous Klucel EF solution via top spray process in fluid bed, as shown in Table 13.

TABLE 13

Composition of Tablet Core, Lot 2007-149-39

| Component | % (w/w) 2007-149-39 |
|---|---|
| Mg Lactate Dihydrate, powder | 89.25 |
| Carbopol 974P, extragranular | 5.00 |
| Klucel EF | 4.75 |
| Mg Stearate, veg source | 1.00 |
| Total | 100.00 |

Figure 13:
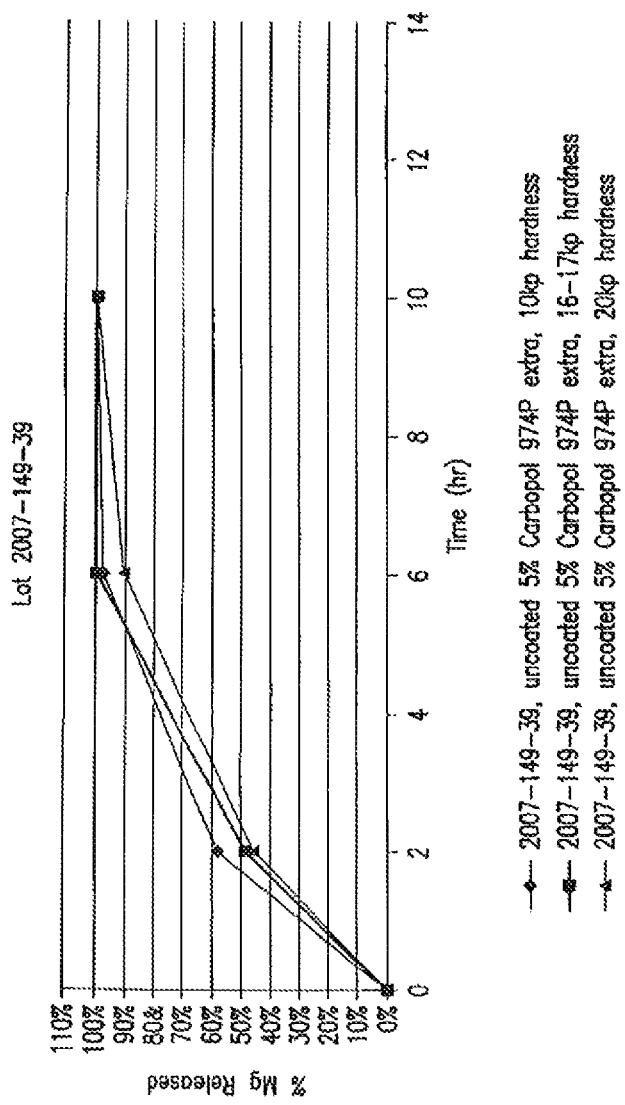
FIG. 13 shows the dissolution profile of $Mg^{2+}$ from Uncoated Cores (Lot 2007-149-39) based on Klucel EF and Extragranular Carbopol 974P and Different Tablet Hardness; Aqueous Process.

Next, granules were dried via fluid bed. The granules were then calibrated/milled to ≤20 mesh size. Extragranular Carbopol 974P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 13. Without wishing to be bound by theory, it is believed that hardness plays a role in dissolution characteristics, with the harder tablets having a slightly slower release.

14. Preparation of Tablets (Lot 2007-149-43)

Tablet cores were prepared by wet granulation of Mg Lactate with aqueous Klucel EF solution via top spray process in fluid bed, as shown in Table 14.

TABLE 14

Composition of Tablet Core, Lot 2007-149-43

| Component | % (w/w) 2007-149-43 |
|---|---|
| Mg Lactate Dihydrate, powder | 89.25 |
| Carbopol 974P, extragranular | 5.00 |
| Klucel EF | 4.75 |
| Mg Stearate, veg source | 1.00 |
| Total | 100.00 |

Figure 14:
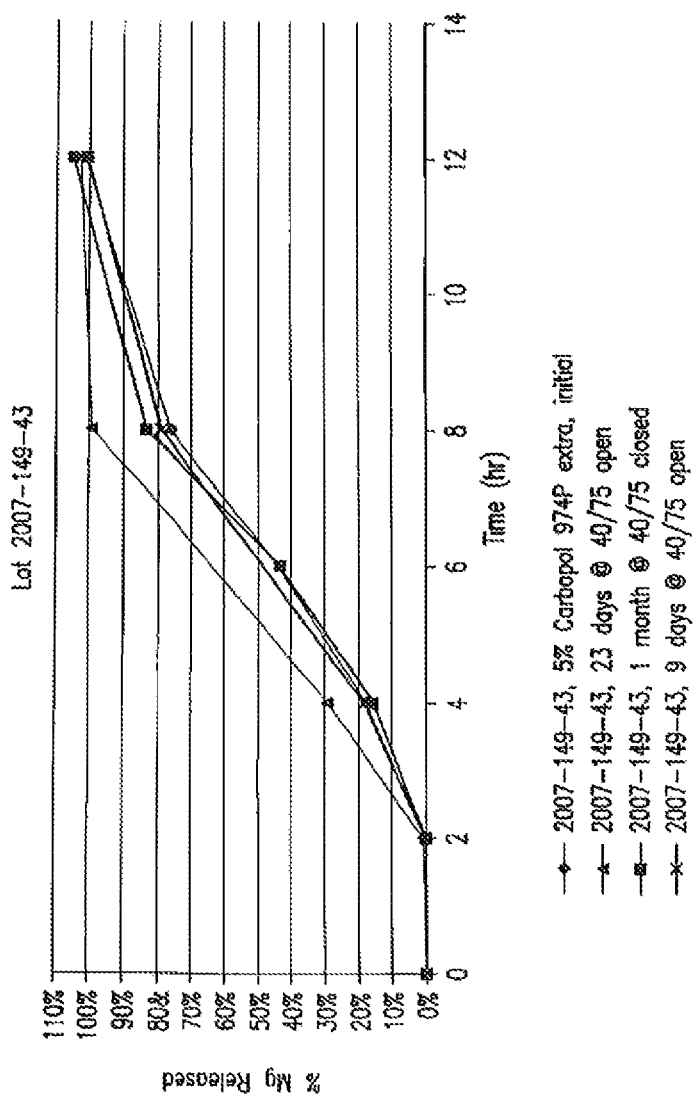
FIG. 14 shows the dissolution profile of $Mg^{2+}$ from Enteric Coated Cores (Lot 2007-149-43) based on Klucel EF and Extragranular Carbopol 974P; Aqueous Process.

Next, granules were dried via fluid bed. The granules were then calibrated/milled to ≤20 mesh size. Extragranular Carbopol 974P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied. The tablets were tested under the Tablet Dissolution Test. The results are shown in FIG. 14. Stability testing as a function of time shows that the formulation is stable under closed bottle conditions; open bottle conditions show good results as well.

15. Preparation of Tablets (Lot 2007-149-50)

Tablet cores were prepared by wet granulation of Mg Lactate with Klucel EF in 80/20 IPA/water solution via top spray process in fluid bed, as shown in Table 15.

TABLE 15

Composition of Tablet Core, Lot 2007-149-50

| Component | % (w/w) 2007-149-50 |
|---|---|
| Mg Lactate Dihydrate, powder | 89.22 |
| Carbopol 974P, extragranular | 5.00 |
| Klucel EF | 4.78 |
| Mg Stearate, veg source | 1.00 |
| Total | 100.00 |

Figure 15:
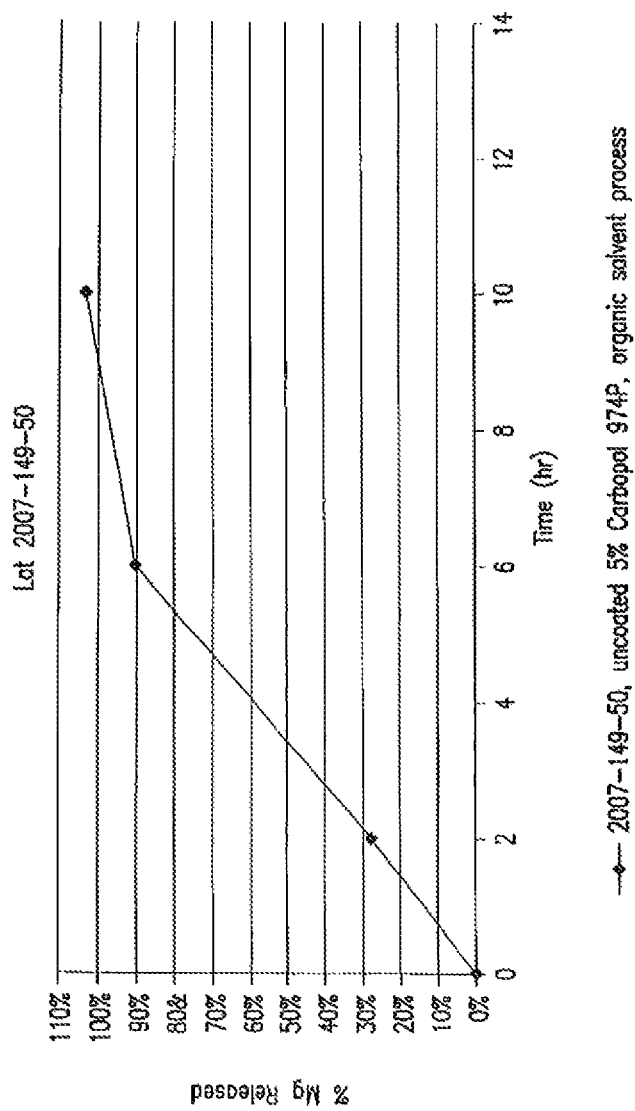
FIG. 15 shows the dissolution profile of $Mg^{2+}$ from Uncoated Cores (Lot 2007-149-50) based on Klucel EF and Extragranular Carbopol 974P; Organic Solvent Process.

Next, granules were dried via fluid bed. The granules were then calibrated/milled to ≤20 mesh size. Extragranular Carbopol 974P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. Opadry Clear subcoat was then applied. The tablets were tested under the Tablet Dissolution Test. The results are shown in FIG. 15.

16. Preparation of Tablets (Lot 2007-149-52)

Tablet cores were prepared by wet granulation of Mg Lactate with Klucel EF in 80/20 IPA/water solution via top spray process in fluid bed, as shown in Table 16.

TABLE 16

Composition of Tablet Core, Lot 2007-149-52

| Component | % 2007-149-52 |
|---|---|
| Mg Lactate Dihydrate, powder | 89.22 |
| Carbopol 974P, extragranular | 5.00 |
| Klucel EF | 4.78 |
| Mg Stearate, veg source | 1.00 |
| Total | 100.00 |

Figure 16:
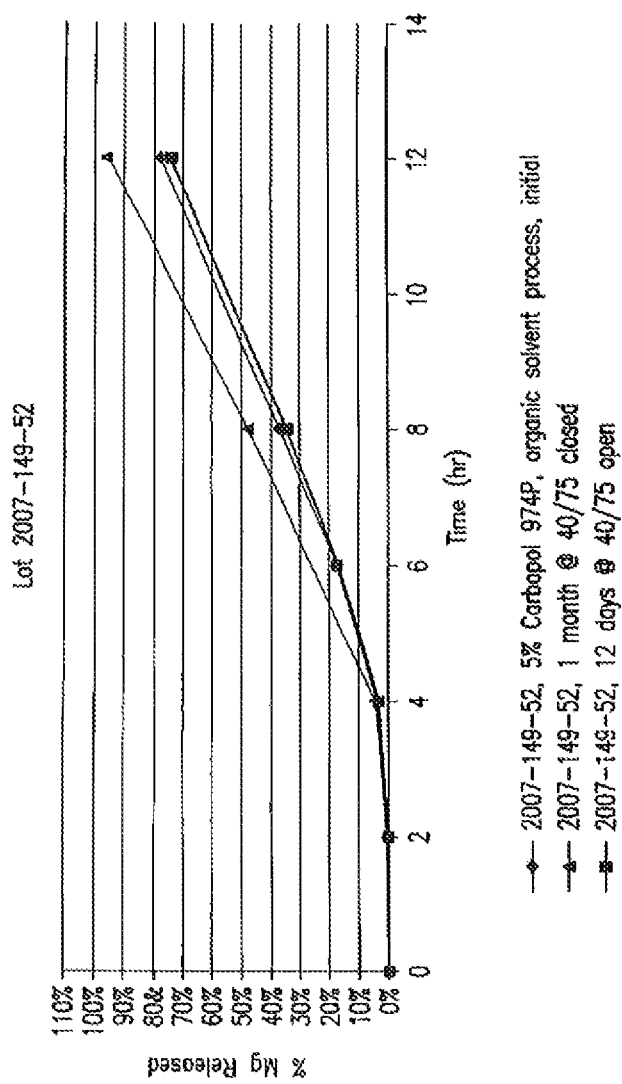
FIG. 16 shows the dissolution profile of $Mg^{2+}$ from Enteric Coated Cores (Lot 2007-149-52) based on Klucel EF and Extragranular Carbopol 974P; Organic Solvent Process.

Next, granules were dried via fluid bed. The granules were then calibrated/milled to ≤20 mesh size. Extragranular Carbopol 974P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied. The tablets were tested under the Tablet Dissolution Test. The results are shown in FIG. 16. Stability testing as a function of time shows that the formulation is stable under closed bottle conditions; open bottle conditions show good results as well.

17. Preparation of Tablets (Lots 2007-149-64-A, B & C)

Tablet cores were prepared by wet granulation of Mg Lactate with aqueous Klucel EF solution via top spray process in fluid bed, as shown in Table 17.

TABLE 17

Composition of Tablet Core, Lot 2007-149-64-A, B & C

| Component | % (w/w) 2007-149-64-A | 2007-149-64-B | 2007-149-64-C |
|---|---|---|---|
| Mg Lactate Dihydrate, powder | 89.25 | 90.68 | 92.10 |
| Carbopol 974P, extragranular | 5.00 | 3.50 | 2.00 |
| Klucel EF | 4.75 | 4.82 | 4.90 |
| Mg Stearate, veg source | 1.00 | 1.00 | 1.00 |
| Total | 100.00 | 100.00 | 100.00 |

Figure 17:
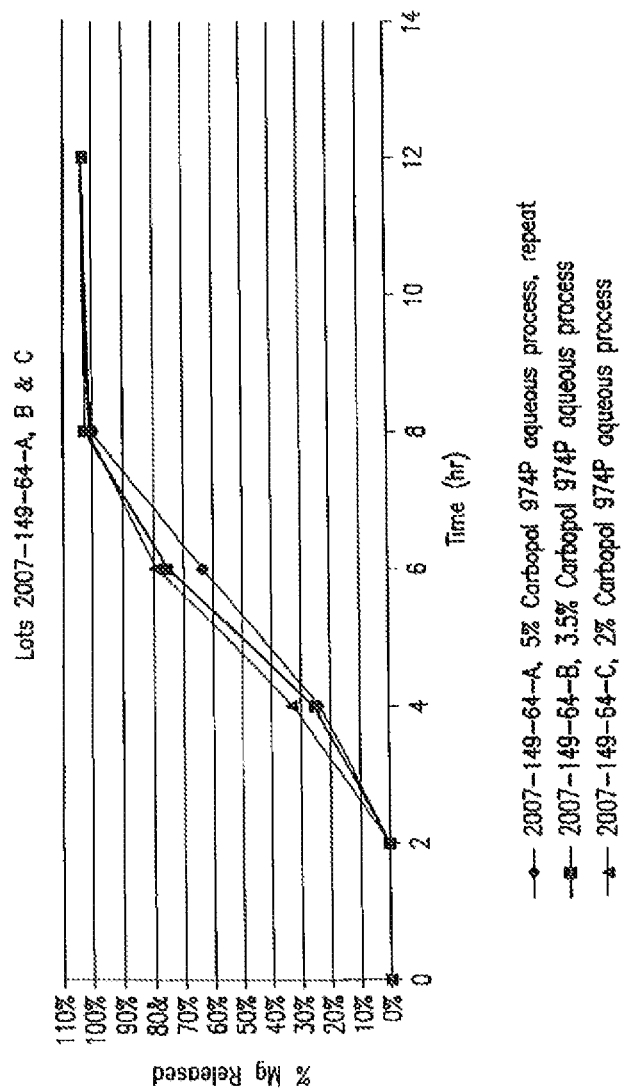
FIG. 17 shows the dissolution profile of $Mg^{2+}$ from Enteric Coated Cores (Lots 2007-149-64-A, B & C) based on Klucel EF and Extragranular Carbopol 974P; Aqueous Process.

Next, granules were dried via fluid bed. The granules were then calibrated/milled to ≤20 mesh size. Extragranular Carbopol 974P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied. The tablets were tested under the Tablet Dissolution Test. The results are shown in FIG. 17. Without wishing to be bound by theory, it is believed that lower levels of Carbopol 974P slightly increase the dissolution rate.

18. Preparation of Tablets (Lots 2007-149-39, 60, 66 & 67)

Tablet cores were prepared by wet granulation of Mg Lactate with aqueous Klucel EF solution via top spray process in fluid bed, as shown in Table 18.

TABLE 18

Compositions of Tablet Core, Lots 2007-149-39, 60, 66 & 67

| Component | % (w/w) 2007-149-39 2007-149-60 2007-149-66 2007-149-67 |
|---|---|
| Mg Lactate Dihydrate, powder | 89.25 |
| Carbopol 974P, extragranular | 5.00 |
| Klucel EF | 4.75 |
| Mg Stearate, veg source | 1.00 |
| Total | 100.00 |

Figure 18:
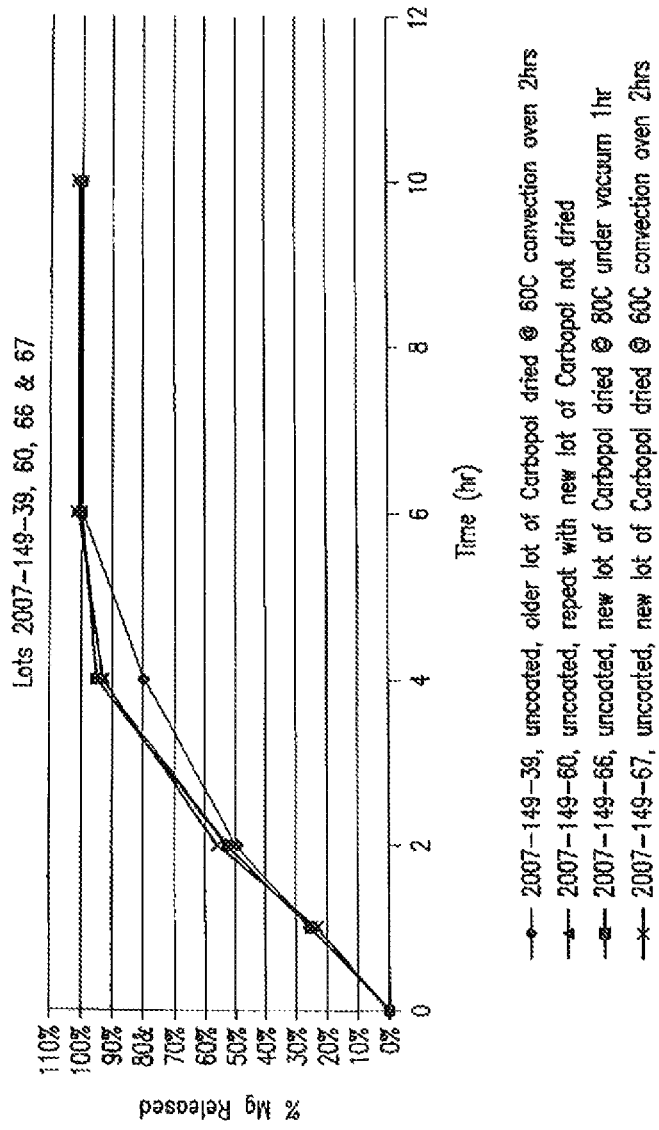
FIG. 18 shows the dissolution profile of $Mg^{2+}$ from Uncoated Cores (Lots 2007-149-39, 60, 66 & 67) based on Klucel EF and Extragranular Carbopol 974P; Aqueous Process.

Next, granules were dried via fluid bed; however, different drying conditions were investigated. The granules were then calibrated/milled to ≤20 mesh size. Extragranular Carbopol 974P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. Opadry Clear subcoat and Eudragit L30D-55 enteric coat were then applied. The tablets were tested under the Tablet Dissolution Test. The results are shown in FIG. 18. Without wishing to be bound by theory, it is believed that drying conditions have little to no effect on dissolution.

19. Preparation of Tablets (Lots 2007-149-91, 92, 94 & 95)

Tablet cores were prepared by wet granulation of Mg Lactate with aqueous Klucel EF solution via top spray process in fluid bed, as shown in Table 19.

TABLE 19

Composition of Tablet Core, Lots 2007-149-91, 92, 94 & 95

| Component | % (w/w) | | | |
|---|---|---|---|---|
| | 2007-149-91 | 2007-149-92 | 2007-149-94 | 2007-149-95 |
| Mg Lactate Dihydrate, powder | 89.25 | 84.51 | 84.60 | 80.10 |
| Ethocel Std 10FP, extragranular | 5.00 | 10.00 | 5.00 | 10.00 |
| Klucel ® EF | 4.75 | 4.49 | 9.40 | 8.90 |
| Mg Stearate, veg source | 1.00 | 1.00 | 1.00 | 1.00 |
| Total | 100.00 | 100.00 | 100.00 | 100.00 |

Figure 19:
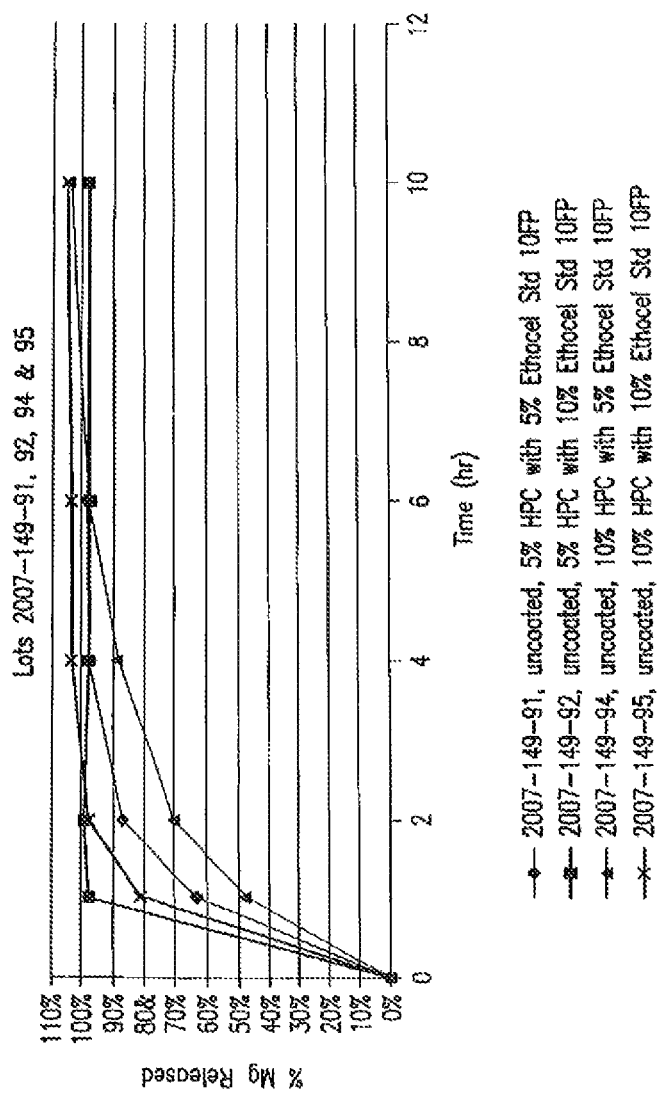
FIG. 19 shows the dissolution profile of $Mg^{2+}$ from Uncoated Cores (Lots 2007-149-91, 92, 94 & 95) based on Klucel EF and Extragranular Ethocel Std 10FP; Aqueous Process.

Next, granules were dried via fluid bed. The granules were then calibrated/milled to ≤20 mesh size. Extragranular Ethocel Std 10FP was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 19. Without wishing to be bound by theory, it is believed that the formulation produced dissolution rates that were too fast.

20. Preparation of Tablets (Lots 2007-149-99 & 100)

Tablet cores were prepared by wet granulation of Mg Lactate with aqueous Klucel EF solution via top spray process in fluid bed, as shown in Table 20.

TABLE 20

Composition of Tablet Core, Lots 2007-149-99 & 100

| Component | % (w/w) | |
|---|---|---|
| | 2007-149-99 | 2007-149-100 |
| Mg Lactate Dihydrate, powder | 89.25 | 84.51 |
| Xantural 75, extragranular | 5.00 | 10.00 |
| Klucel ® EF | 4.75 | 4.49 |
| Mg Stearate, veg source | 1.00 | 1.00 |
| Total | 100.00 | 100.00 |

Figure 20:
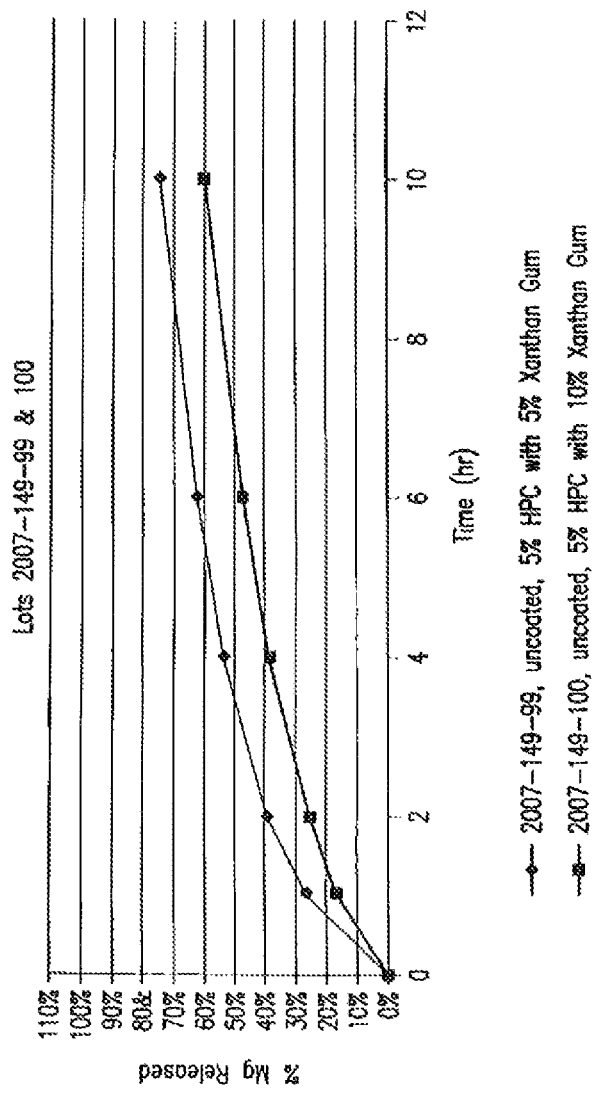
FIG. 20 shows the dissolution profile of $Mg^{2+}$ from Uncoated Cores (Lots 2007-149-99 & 100) based on Klucel EF and Extragranular Xanthan Gum; Aqueous Process.

Next, granules were dried via fluid bed. The granules were then calibrated/milled to ≤20 mesh size. Extragranular Xantural 75 was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 20. Without wishing to be bound by theory, it is believed that the Xanthan gum system slowed dissolution rate to that below the targeted profiles.

21. Preparation of Tablets (Lots 2008-046-9, 22 & 24B)

Tablet cores were prepared by wet granulation of Mg Lactate with aqueous Klucel EF solution via top spray process in fluid bed, as shown in Table 21.

TABLE 21

Composition of Tablet Core, Lots 2008-046-9, 22, & 24B

| Component | % (w/w) | | |
|---|---|---|---|
| | 2008-046-9 | 2008-046-22 | 2008-046-24B |
| Mg Lactate Dihydrate, powder | 88.20 | 88.20 | 88.20 |
| Klucel ® EF | 9.80 | 9.80 | 9.80 |
| Mg Stearate, veg source | 2.00 | 2.00 | 2.00 |
| Total | 100.00 | 100.00 | 100.00 |

Figure 21:
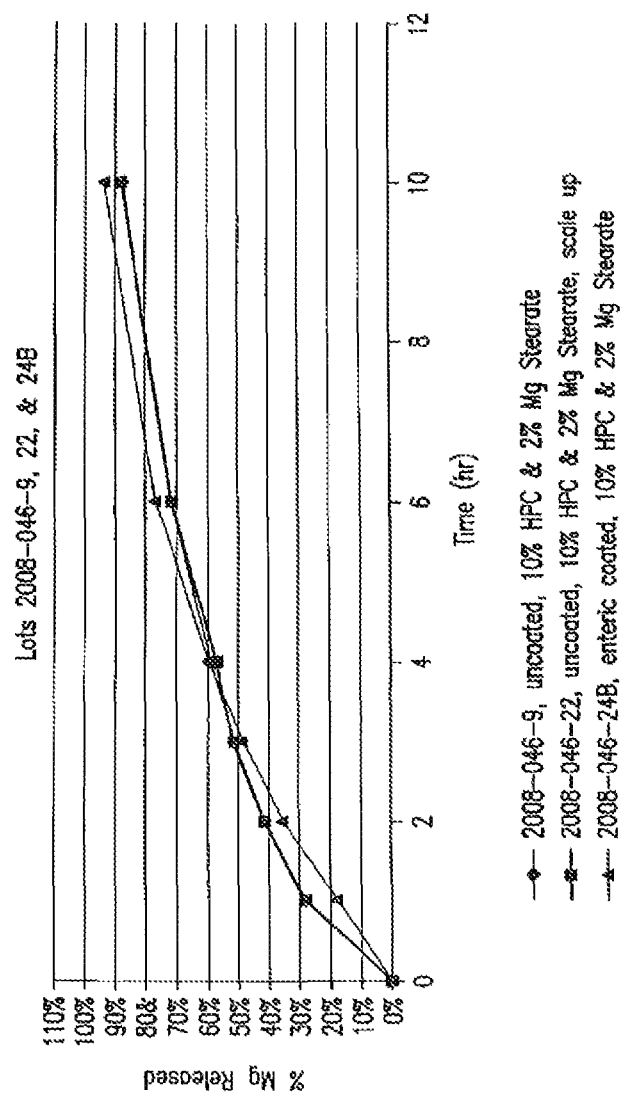
FIG. 21 shows the dissolution profile of $Mg^{2+}$ from Uncoated Cores (Lots 2008-046-9, 22 & 24B) based on Klucel EF and 2% Mg Stearate; Aqueous Process.

Next, granules were dried via fluid bed. The granules were then calibrated/milled to ≤20 mesh size. Extragranular Carbopol 974P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 21. The enteric-coated tablet profile in this example is shown with reference to the time in buffer solution only. Without wishing to be bound by theory, it is believed that the increased level of magnesium stearate allowed for good tablet ejection during compression. Upon dissolution, it was observed that the level of HPC allows for controlled release.

22. Preparation of Tablets (Lots 2008-046-12 & 14)

Tablet cores were prepared by wet granulation of Mg Lactate with aqueous Klucel EF solution via top spray process in fluid bed, as shown in Table 22.

TABLE 22

Composition of Tablet Core, Lots 2008-046-12 & 14

| Component | % (w/w) | |
|---|---|---|
| | 2008-046-12 | 2008-046-14 |
| Mg Lactate Dihydrate, powder | 89.25 | 89.25 |
| Carbopol 971P, extragranular | 5.00 | 5.00 |
| Klucel EF | 4.75 | 4.75 |
| Mg Stearate, veg source | 1.00 | 1.00 |
| Total | 100.00 | 100.00 |

Figure 22:
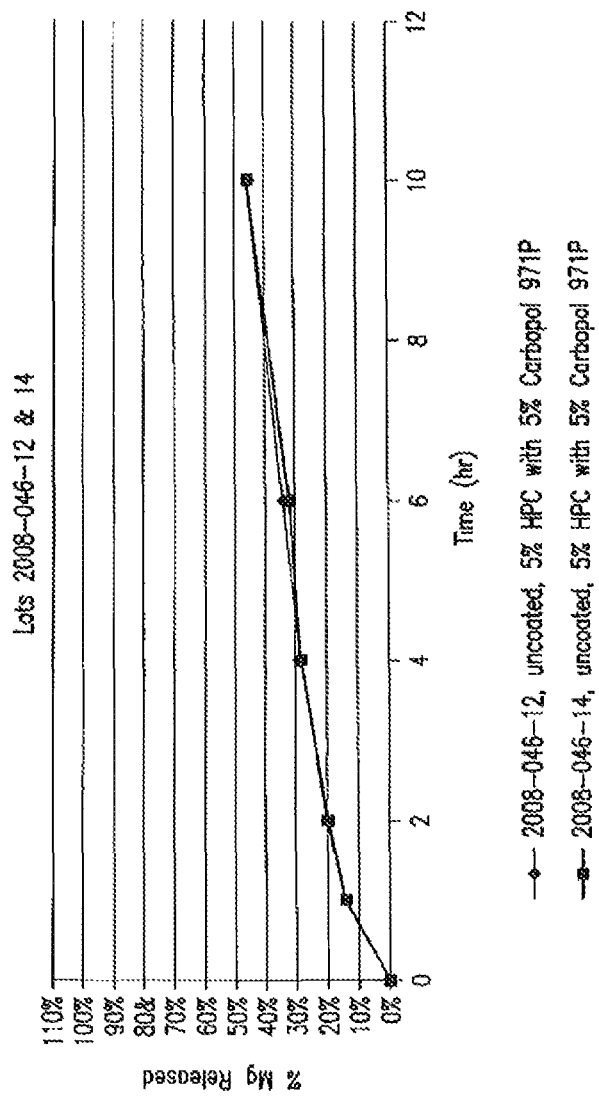
FIG. 22 shows the dissolution profile of $Mg^{2+}$ from Uncoated Cores (Lots 2008-046-12 & 14) based on Klucel® EF and Extragranular Carbopol® 971P; Aqueous Process.

Next, granules were dried via fluid bed. The granules were then calibrated/milled to ≤20 mesh size. Extragranular Carbopol 971P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 22. Without wishing to be bound by theory, it is believed that Carbopol® 971P achieves superior reproducibility between lots and offers increased dissolution control over Carbopol® 974P. The decreased dissolution rate indicates this increased control.

23. Preparation of Tablets (Lots 2008-046-21 & 24A)

Tablet cores were prepared by wet granulation of Mg Lactate with aqueous Klucel EF solution via top spray process in fluid bed, as shown in Table 23.

TABLE 23

Composition of Tablet Core, Lots 2008-046-21 & 24A

| Component | % (w/w) | |
|---|---|---|
| | 2008-046-21 | 2008-046-24A |
| Mg Lactate Dihydrate, powder | 92.15 | 92.15 |
| Carbopol ® 971P, extragranular | 2.00 | 2.00 |
| Klucel ® EF | 4.85 | 4.85 |
| Mg Stearate, veg source | 1.00 | 1.00 |
| Total | 100.00 | 100.00 |

Figure 23:
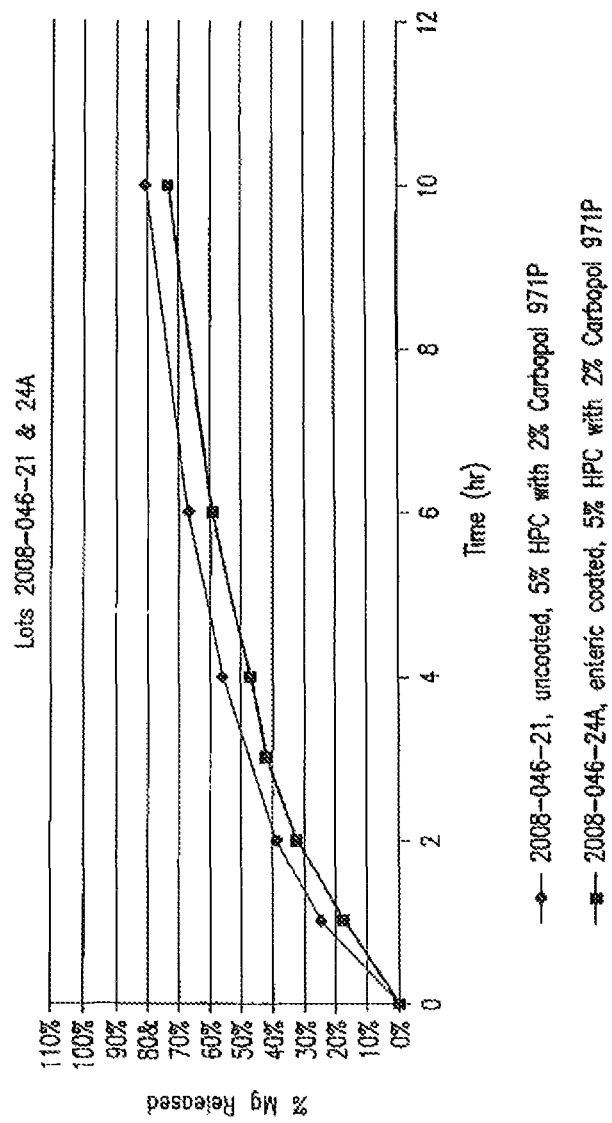
FIG. 23 shows the dissolution profile of $Mg^{2+}$ from Uncoated & Enteric Coated Cores (Lots 2008-046-21 & 24A) based on Klucel EF and Extrangranular Carbopol 971P; Aqueous Process.

Next, granules were dried via fluid bed. The granules were then calibrated/milled to ≤20 mesh size. Extragranular Carbopol 971P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 23. The enteric-coated tablet profile in this example is shown with reference to the time in buffer solution only. Without wishing to be bound by theory, it is believed that reducing the level of Carbopol® 971P increased dissolution rate closer to desired values. Comparison of coated and uncoated cores shows that the enteric coating slows dissolution slightly.

24. Preparation of Tablets (Lots 2008-046-25 & 27)

Tablet cores were prepared by wet granulation of Mg Lactate with aqueous Klucel EF solution via top spray process in fluid bed, as shown in Table 24.

TABLE 24

Composition of Tablet Core, Lots 2008-046-25 & 27

| Component | % (w/w) | |
|---|---|---|
| | 2008-046-25 | 2008-046-27 |
| Mg Lactate Dihydrate, powder | 92.15 | 92.15 |
| Carbopol ® 971P, extragranular | 2.00 | 2.00 |
| Klucel ® EF | 4.85 | 4.85 |
| Mg Stearate, veg source | 1.00 | 1.00 |
| Total | 100.00 | 100.00 |

Figure 24:
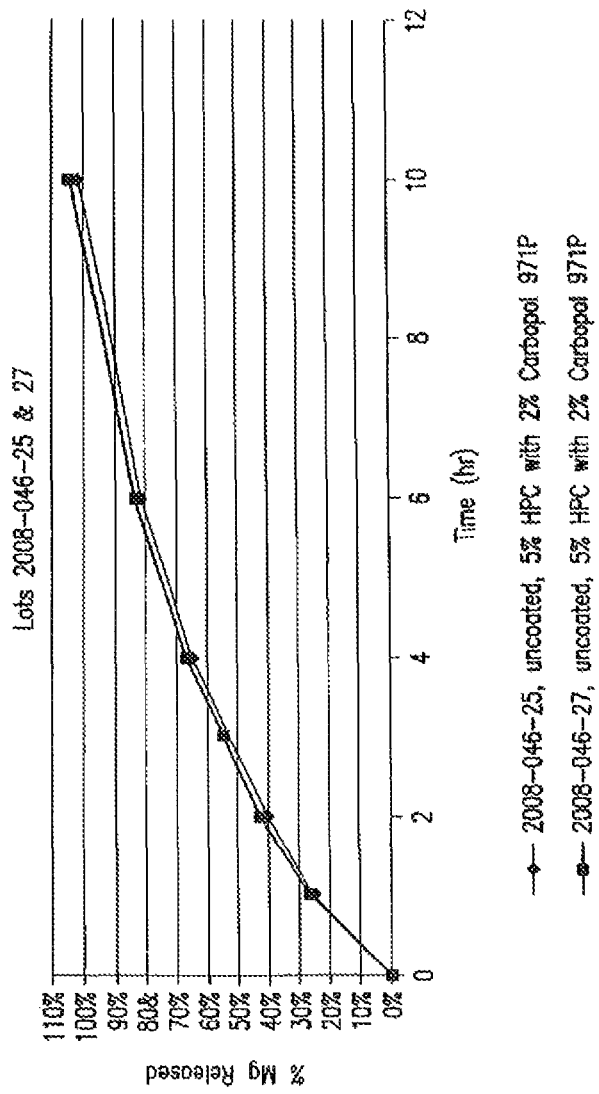
FIG. 24 shows the dissolution profile of $Mg^{2+}$ from Uncoated Cores (Lots 2008-046-25 & 27) based on Klucel® EF and Extragranular Carbopol® 971P; Aqueous Process.

Next, granules were dried via fluid bed. The granules were then calibrated/milled to ≤20 mesh size. Extragranular Carbopol 971P was then blended with the granules with a V-shell blender using Comil. Magnesium stearate was then blended with the granules with a V-shell blender. The final blend was then compressed into tablets using 0.4000"×0.8750" modified oval tooling, at a target hardness of approximately 20 kp. The tablets were tested under the Tablet Dissolution Test. The results are shown in FIG. 24. It was observed that poor granulation of this formulation still allowed for compression.

25. Comparative Example 76 parts of magnesium lactate powder (dihydrate) is passed through a 0.0469 inch screen and introduced into a lodige mixer. The mixer is heated to 50-80° C. 3.2 parts of stearic acid, 3.6 parts of carnauba wax, and 2.3 parts of polyethylene glycol (MW=8000) are heated to 90° C. to 100° C. are introduced into the mixer. The mixer is activated for 3 minutes to ensure uniform mixing. The resulting mixture is then spread onto trays and cooled to room temperature. Once cooled, the mixture is passed through a Fitz Mill having a 0.109-inch screen and introduced into a V-blender. 7.2 parts of microcrystalline cellulose and 7.2 parts of polyethylene glycol (MW=8000) are introduced into the blender and the blender is activated for 10 minutes to provide a uniform mixture. 0.5 parts of calcium stearate, a tabletting lubricant, is added to the blender.

The mixture is removed from the blender and is compressed into tablets in a Stokes B-2 tabletting press having caplet shaped tooling (0.745"×0.306").

The materials were added in the above proportions to produce tablets having an overall weight of 1100 mg (834.6 mg magnesium lactate). The tablets produced contained about 7 milliequivalents of magnesium.

The tablets were tested for friability and capping in accordance with standardized USP test procedures. The tablets had low friability, and showed no capping.

Dissolution of the tablet was performed by placing the tablet in simulated gastric fluid (without enzymes) for two hours and then in simulated intestinal fluid (without enzymes) for 5 hours. The tablet released 82% of the magnesium lactate into solution over a period of 7 hours. The dissolution profile for the tablet is set forth in Table 25.

TABLE 25

| TIME | Percent of $Mag^{2+}$ Released |
|---|---|
| 1 hour | 33 |
| 2 hours | 55 |
| 3 hours | 71 |
| 5 hours | 81 |
| 7 hours | 82 |

26. Treatment of Hypomagnesemia (Prophetic)

Using known techniques (e.g., measurement of serum magnesium levels), a subject (e.g., a human) in need for treatment for hypomagnesemia can be identified. A therapeutically effective amount (e.g., two tablets, twice daily) of the disclosed high-loading and/or controlled release oral dosage forms can be administered to the subject. At intervals during the treatment regimen, the subject is monitored for hypomagnesemia. After the treatment period has concluded, again using known techniques, the subject is found not to be in need for treatment for hypomagnesemia.

It is also contemplated that a subject can be in need for treatment of chronic hypomagnesemia. Thus, at intervals during a treatment regimen, a therapeutically effective amount (e.g., two tablets, twice daily) of the disclosed high-loading and/or controlled release oral dosage forms can be administered to the subject and the subject can be monitored for hypomagnesemia. The subject is found to have a reduced level of hypomagnesemia, compared to a similarly situated subject without treatment with the disclosed high-loading and/or controlled release oral dosage forms.

27. Chemotherapy and Co-Adminstration of a High-Loading, Controlled-Release Oral Dosage Form for Treatment of Drug-Induced Hypomagnesemia (Prophetic)

A subject (e.g., a human) can be treated with chemotherapy—which is known to be associated with decreased magnesium levels—thereby resulting in low magnesium levels. Thus, using known techniques (e.g., measurement of serum magnesium levels), the subject can be identified as in need for treatment for drug-induced hypomagnesemia. A therapeutically effective amount (e.g., two tablets, twice daily) of the disclosed high-loading and/or controlled release oral dosage forms can be co-administered with the chemotherapy to the subject, thereby alleviating the low magnesium levels. After the chemotherapy treatment has concluded, again using known techniques, the subject is found to have a reduced level of hypomagnesemia.

After the treatment regimen has concluded, again using known techniques, the subject is found to have decreased symptoms of hypomagnesemia and/or to be no longer in need for treatment for hypomagnesemia.

Alternatively, a prophylactically effective amount (e.g., two tablets, twice daily) of the disclosed high-loading and/or controlled release oral dosage forms can be administered to the subject before the chemotherapy, thereby preventing or alleviating the low magnesium levels.

28. Treatment of Diabetes and Co-Adminstration of a High-Loading, Controlled-Release Oral Dosage Form for Treatment of Disease-Induced Hypomagnesemia (Prophetic)

A subject (e.g., a human) can be treated for diabetes—a disorder associated with decreased magnesium levels—with a drug known to be effective for treating the diabetes (e.g., insulin), but ineffective for alleviating low magnesium levels stemming from the diabetes, thereby resulting in low magnesium levels in the subject. Thus, using known techniques (e.g., measurement of serum magnesium levels), the subject can be identified as in need for treatment for disease-induced hypomagnesemia. A therapeutically effective amount (e.g., two tablets, twice daily) of the disclosed high-loading and/or controlled release oral dosage forms can be co-administered with the drug known to be effective for treating diabetes to the subject, thereby alleviating the low magnesium levels. At intervals during the co-administration regimen, again using known techniques, the subject is found to have a reduced level of hypomagnesemia. After the magnesium administration has concluded, again using known techniques, the subject is found to have decreased symptoms of hypomagnesemia and/or to be no longer in need for treatment for hypomagnesemia.

Alternatively, a prophylactically effective amount (e.g., two tablets, twice daily) of the disclosed high-loading and/or controlled release oral dosage forms can be administered to the subject before the diabetes treatment regimen, thereby preventing or alleviating the low magnesium levels.

29. Reagent Specifications

Excipients and active pharmaceutical ingredients (API) suitable for use in the disclosed methods and in producing the disclosed compositions include reagents disclosed below. Preferred specifications are tabulated.

a. Excipients

Excipients used the disclosed compositions include hydroxypropyl cellulose, magnesium stearate, Opadry II Clear, methacrylic acid copolymer dispersion, triethyl acetate, mono- and di-glycerides, and Opacode Black.

| Hydroxypropyl Cellulose NF (Klucel EF Pharm) (Manufactured by: Hercules, Inc.) | |
|---|---|
| Test | Specifications |
| Description | Off white powder |
| Identification | IR compares to std |
| Loss on drying | NMT 5.0% |
| pH | 5.0-8.0 |
| Assay for Hydroxypropyl groups | NMT 53.4%-77.5% |
| Viscosity | 300-600 cps |
| Residue on Ignition | NMT 0.2% |
| Heavy Metals, II | NMT 20 ppm |

| Magnesium Stearate NF (Powder-Vegetable Source) (Manufactured by: Mallinckrodt, Inc.) | |
|---|---|
| Test | Specifications |
| Description | White powder |
| Identification A | Responds to test for Mg |
| Microbial Limits | |
| Total Aerobic Count | NMT 1000 cfu/g |
| Molds and Yeasts | NMT 500 cfu/g |
| *Eschericia Coli* | Absent |
| *Salmonella* Sp. | Absent |
| Loss on Drying | NMT 6.0% |
| Lead | NMT 0.001% (10 ppm) |
| Assay | 4.0-5.0% mg (D.B.) |

| Opadry II Clear 85F19250 (Manufactured by: Colorcon) | |
|---|---|
| Test | Specifications |
| Description | Off White powder |
| Identification A | IR compares to standard |

| Methacrylic Acid Copolymer Dispersion NF (Eudragit L30D-55) (Manufactured by: Evonik) | |
|---|---|
| Test | Specifications |
| Description | Milky white liquid of low viscosity with a faint characteristic color |
| Identification A | IR compares to standard |
| Identification B | A clear film is formed |
| Viscosity | NMT 15 cps |
| pH | 2.0-3.0 |
| Loss on drying | 68.5%-71.5% |
| Residue on Ignition | NMT 0.2% |
| Heavy Metals II | NMT 0.002% |
| Limit of Monomers | NMT 0.01% |
| Coagulum Content | NMT 1000 mg (1.0%) |
| Assay | 46.0%-50.6% |
| Residue Solvents Ethanol | NMT 5000 ppm |

| Triethyl Acetate NF (Manufactured by: Vertellus, aka Mortflex) | |
| --- | --- |
| Test | Specifications |
| Description | Clear essentially odorless oily liquid |
| Identification A | IR compares to standard |
| Identification B | The retention time of the major peak in the Assay preparation corresponds to that in the USP Triethyl Citrate RS. |
| Specific Gravity | 1.135 and 1.139 |
| Refractive Index | 1.439 and 1.441 |
| Acidity | Not more than 1.0 mL is required |
| Water Method I | NMT 0.25% |
| Heavy Metals, II | NMT 0.001% |
| Assay | 99.0%-100.5% (A.B.) |

| Mono- and Di-glycerides NF (Imwitor 900K) (Manufactured by: Sasol GmbH) | |
| --- | --- |
| Test | Specifications |
| Description | White to slightly yellow powder |
| Acid Value | NMT 4 |
| Residue on Ignition | NMT 0.1% |
| Hydroxyl Value | 190-240 |
| Iodine Value | NMT 10 |
| Saponification Value | 160-175 |
| Heavy Metals, II | NMT 0.001% |
| Arsenic, II | NMT 3 ppm |
| Limit of free Glycerin | NMT 7.0% |
| Assay, Monoglycerides | 40.0%-55.0% |
| Description | Black liquid |
| Specific Gravity | Between 1.05 and 1.15 | b. Active Pharmaceutical Ingredients

Active pharmaceutical ingredients (API) used the disclosed compositions include magnesium lactate dihydrate.

| Magnesium Lactate Dihydrate EP (Powder) (Manufactured by: Jost Chemical) | |
| --- | --- |
| Test | Specifications |
| Description | White to practically white, odorless, crystalline powder |
| Identification A | A dark green ring appears at the junction of the two liquids |
| Identification B | A white crystalline precipitate is formed |
| Appearance of Solution | Not more intensely colored than reference solution BY6 |
| Loss on drying | 14.0-17.0% |
| Assay | 98.0%-102.0% (D.B.) |
| Microbial Limits | |
| Total Aerobic Plate Count | 1000 cfu/g Max |
| Yeast and Mold Count | 100 cfu/g Max |
| Total Coliforms | Negative |

30. Preparation of Magnesium Lactate Modified Release Tablets, 10 Meq (121.5 Mg), 10% Hpc Formulation, Uncoated Cores Tablets were prepared according to disclosed methods, using the below tabulated ingredients and specifications.

TABLE 26

| | Lot No. | | | | | | |
| --- | --- | --- | --- | --- | --- | --- | --- |
| | 2008-046-22 | 2008-046-029A | 2008-046-37 | F-11-1 | F11-1 | RD1081-F12 | RD1081-F14 |
| Batch Size (kg) | 7.0 | | | | | | 122.4 |
| Granule Source | PF | Mikart | Mikart | Mikart | Mikart | Mikart | Mikart |
| Magnesium Lactate Lot # (Jost) | 25307032 | 25307052 | 25307052 | | | 08R0089 | 08R0089 |
| Klucel Lot # (Aqualon) | 77542 | 65619 | 65619 | | | 0680143 | 0680143 |
| Magnesium Stearate Lot # (Mallinckrodt) | M02539 | M02539 | M02539 | | | 078-186 | 078-186 |
| Tableting Location | PF | PF | PF | Mikart | Mikart | Mikart | Mikart |
| Tablet Batch Size (kg) | 2.25 | 3.0 | 3.0 | | | 122.4 | 122.4 |
| Hardness | 20 | 20 | 20 | | | | 20 |
| Site of Dissolution Testing | PF | PF | PF | Mikart | PF | Mikart | Mikart |
| % Dissolved (Time in hrs) | | | | | | | |
| 1 | 27.7 | 27 | 25.6 | 30 | 30 | 30 | 28 |
| 2 | 41.4 | 40 | 37.9 | 48 | 42 | 47 | 40 |
| 3 | 50.4 | 53 | 45.1 | | 55 | | |
| 4 | 57.4 | 55 | 55.8 | 67 | 65 | 66 | 56 |
| 6 | 72.0 | 66 | 72.7 | 81 | 79 | 79 | 69 |
| 10 | 88.3 | 79 | 85.1 | 98 | 94 | 90 | 87 |

31. Preparation of Magnesium Lactate Modified Release Tablets, 10 Meq (121.5 Mg), 10% Hpc Formulation, Enteric Coated Tablets Tablets were prepared according to disclosed methods, using the below tabulated ingredients and specifications.

TABLE 27

| | Lot No. | | | | | | |
|---|---|---|---|---|---|---|---|
| | 2008-046-24B | 2008-046-24B closed container | 2008-046-24B open container | 2008-046-35A | 2008-046-40 | RD1081-F13 | RD1081-F15 |
| Corresponding Core Tablets | 2008-046-22 | 2008-046-22 | 2008-046-22 | 2008-046-29A | 2008-046-38* (not tested) | RD1081-F12 | RD1081-F14 |
| Coating Batch Size (kg) | | 0.9 | 0.9 | | | 100 | 11 kg |
| % Dissolved-Hours in Buffer (After 2 hrs in Acid) | | | | | | | |
| (Acid Stage) | 0.1 | 0.0 | 0.0 | 0.0 | 0.0 | 0 | 1 |
| 1 | 18.4 | 19.1 | 26.5 | 14.6 | 23.6 | 27 | 23 |
| 2 | 35.8 | 40.8 | 44.9 | 31.1 | 38.8 | 45 | 38 |
| 4 | 60.2 | 56.9 | 70.0 | 47.2 | 59.9 | 72 | 58 |
| 6 | 77.1 | 71.7 | 87.4 | 66.3 | 77.6 | 90 | 71 |
| 10 | 94.3 | 90.0 | 98.9 | 75.9 | 95.6 | 106 | 90 |

*Granule manufactured at Mikart and 3.0 kg tablets compressed at PharmaForm

32. Batch Coating Procedure

To master tank #1, charge 44 kg Purified Water USP. Begin mixing at a speed of 700 rpm (±500 rpm) adjusting speed within the specified range to create a vortex. With continuous mixing, add 6.000 kg Opadry II Clear (85F19250). Reduce the mixer speed until a vortex is no longer present. Adjust the mixer speed to minimize the vortex while maintaining adequate agitation to produce a homogeneous mixture. Avoid creating excess foam, if possible. Mix continuously for 45 minutes at a speed of 700 rpm (±500 rpm) or until it is completely dissolved. Adjust the mixer speed within the specified range to minimize the vortex while maintaining adequate agitation. Avoid creating excess foam, if possible. Allow coating solution to stand for 15 minutes, or until most of the foam on top of the solution has dissipated, then proceed with coating the tablets.

Charge approximately 20 kg Purified Water USP to a stainless steel jacketed tank (auxiliary tank #1). Cover the stainless steel tank and then heat the Purified Water USP to 70° C. to 75° C. When the Purified Water USP reaches 70° C. to 75° C., discontinue heat. Weigh out 15 kg of the hot Purified Water USP into a 60 L stainless steel pail. Avoid allowing the water to cool below 70° C. If the water falls below 70° C. prior to material addition, it can be reheated and weighed again prior to continuing.

To the contents of auxiliary tank #2, add 2.295 kg Triethyl Citrate and 0.765 kg Mono-and-Di-Glycerides. Mix for 10 to 20 minutes using a Homogenizer at a speed of 9000 rpm (±500 rpm). To the contents of auxiliary tank #2, add 22.740 kg Purified Water. Mix with a conventional mixer at a slower speed until the temperature drops below 30° C.

Pass 51.000 kg Methacrylic Acid Copolymer Dispersion NF through a #80 mesh screen and charge to master tank #2. Add the solution to master tank #2 slowly and gently mix for at least 15 minutes.

Determine the amount of the Opadry Clear Coating Solution to be applied to the tablets as follows: (Uncoated) Weight of Tablets×0.166667 kg. Determine the amount of the Enteric Coating Dispersion to be applied to the tablets as follows: (Uncoated) Weight of Tablets×0.306 kg. In a 60" coating pan, apply the required quantity of the Opadry Clear Coating Solution onto the tablets maintaining the specified spray conditions: Inlet Air Flow: 2500-5000 CFM (Target: 4200), Inlet Temperature: 50° C.-70° C., Exhaust Air Temperature: Monitor, temperature should not fall below 40° C., Spray Rate: 500-1000 mL/min (Target 750), Guns: 7-11 inches from bed, no overlap, Atomization Pressure: 50-70 psi (Target 60 psi), Pattern Pressure: 20-40 psi (Target 30 psi), Pan Load: 330 kg maximum, Prewarm Bed Temperature: 45° C.-50° C., Pan Speed: 2-6 rpm (Target 4), and Nozzle/Cap: 1.2 mm needle/1.2 mm anti bending air cap (#43268).

Once all the solution has been applied maintain the inlet airflow, temperature and pan rotation for an additional 5 minutes. Then, reduce the pan speed to jog mode and lower the inlet temperature to 35° C. Apply the required quantity of the Enteric Coating Dispersion onto the tablets maintaining the specified spray conditions: Inlet Air Flow: 2500-5000 CFM (Target: 4200), Inlet Temperature: 30° C.-50° C. (Target: 40), Exhaust Air Temperature: Monitor, temperature should not rise above 32° C., Spray Rate: 350-650 mL/min (Target 500), Atomization Pressure: 50-70 psi (Target 60 psi), Pattern Pressure: 20-40 psi (Target 30 psi), and Pan Speed: 2-6 rpm (Target 4).

Once all the dispersion has been applied maintain the inlet airflow, temperature and pan rotation for an additional 3 minutes. Then, discharge the tablets into double poly-lined containers, distributed evenly on paper-lined trays. Place all trays on racks in the oven and cure at 50° C. (±5° C.) for 24 hours, then cool the tablets down to below 30° C. Discharge the tablets into double poly-lined containers.

33. Assay for Tablet Magnesium Content

Magnesium content for the disclosed compositions can be determined using the techniques set forth below.

a. Solutions Preparation

Placebo: Mix the amount of the placebo composite of excipients and coating substances equivalent to 2.5 tablets with 150 mL of de-ionized (DI) water under stirring in a 250.0-mL volumetric flask. Cool to room temperature and remove the stir bar. Dilute to volume and mix. Filter solution through 0.45 µm PVDF syringe filter. Diluted HCl: Mix 227 mL of hydrochloric acid with DI water in 1000-mL volumetric flask and dilute to volume. pH 10 Ammonium Buffer Solution: Weigh 17.5 g Ammonium Chloride transfer to a 250 mL volumetric flask, add 142 mL of Ammonium Hydroxide, dilute to volume with DI water, and mix well. ECBT Indicator: Dissolve 0.2 g of Eriochrome Black Tin 50 mL of Methanol and mix well.

b. Sample Preparation

Magnesium Assay Sample (Prepared in triplicate): Accurately weigh ten tablets and finely powder using a clean mortar and pestle; ensure the absence of large pieces of the film coating flakes. Transfer an accurately weighed portion equivalent to one tablet into a 100 mL volumetric flask. Add 70 mL of DI water and stir at room temperature for at least 15 hours. Cool sample to room temperature, remove the stir bar, and dilute to volume with DI water. Mix well. Centrifuge the mixture at 4000 rpm for 10 minutes. Filter the supernatant with a 0.45 µm PVDF syringe filter.

c. Testing Procedure

Placebo Titration: Pipet 25.0 mL of filtered placebo solution to a 250 mL Erlenmeyer flask. Add 10 mL, pH 10-ammonium buffer, 40 mL DI water, and 4 drops of ECBT Indicator to the flask. With constant stirring, titrate with 0.05 M EDTA VS until the solution turns blue. Record volume of EDTA used. Assay Sample Titration: Pipet 25.0 mL of the Assay Sample to a 250 mL Erlenmeyer flask. Add 10 mL pH 10 Ammonium Buffer, 100 mL DI water, and 4 drops ECBT Indicator to the flask. With constant stirring, titrate with 0.05 M EDTA VS until solution turns blue. Record the volume of EDTA used. Repeat for additional Assay Preparations. Magnesium content can be calculated as shown below:

$$\% \ LC = \frac{M \times (V_t - V_b) \times 24.31 \times \frac{V_{sam}}{V_{pip}} \times \frac{W_t}{W_u}}{121.54} \times 100\%$$

M=Molarity of EDTA
Vt=Volume of EDTA titrated for sample (mL)
Vb=Volume of EDTA titrated for blank (mL)
24.31=Molecular weight of Magnesium
$V_{sam}$=Sample Volume (mL)
$V_{pip}$=Volume of sample used in titration (mL)
$W_t$=Average tablet weight of 10 tablets (mg)
$W_u$=Sample weight (mg)
121.54=Amount of Magnesium per tablet (mg)

34. Assay for Tablet Lactate Content

Lactate content for the disclosed compositions can be determined using the techniques set forth below.

a. Solutions Preparation

Mobile Phase: For each liter of mobile phase, add 1 mL Formic Acid to 1000 mL of water with stirring. Allow to stir for about 1 minute, and then add 1 mL of Dicyclohexylamine. Mix well and filter solution through a 0.45 µm nylon membrane filter. De-gas by sonication for 10 minutes.

b. Standard Preparation

Resolution Solution: Accurately weigh 40±1 mg of Anhydrous Sodium Acetate and 40±1 mg of Sodium Lactate USP and transfer to a 20-mL volumetric flask. Dissolve and dilute to volume with water, and mix well. Working Standard: Accurately weigh 40±1 mg of Sodium Lactate USP and transfer to a 20 mL volumetric flask. Dissolve and dilute to volume with water, and mix well. Check Standard: Accurately weigh 40±1 mg of Sodium Lactate USP and transfer to a 20 ml, volumetric flask. Dissolve and dilute to volume with water, and mix well.

c. Sample Preparation

Accurately weigh ten tablets and finely powder using a clean mortar and pestle; ensure the absence of large pieces of the film coating flakes. Transfer an accurately weighed portion equivalent to one tablet into a 100-mL volumetric flask. Add 70 mL of DI water and stir at room temperature for at least 15 hours. Cool sample to room temperature, remove the stir bar, and dilute to volume with DI water. Mix well. Centrifuge the mixture at 4000 rpm for 10 minutes. Transfer 9.0 mL of supernatant to a 50-mL volumetric flask and dilute to volume with DI water. Mix well. Filter solution through 0.45-um nylon with GMF syringe filter. Discard the first 2-3 drops.

d. Chromatographic Conditions

Column: Waters Symmetry C18, 100×4.6 mm, 3.5 um; Column Temperature: 25° C.±5.0° C.; Sample Temperature: Ambient; Method: Isocratic; Flow Rate: 1.0 mL/min; Wavelength: 210 nm; Injection Volume: 20 µL; and Run Time: 10 minutes.

e. System Suitability

The two blank injections should be free of interference (<0.1% of standard peak area) at the retention time of Lactate peak. The RSD of the Lactate peak area responses in the six replicate injections of the Working Standard is NMT 3.0%. The Tailing Factor for the Lactate peak is NMT 2.0. The resolution between the Acetate and Lactate peaks NLT 2.0. Recovery for Check Standard (average of duplicate injections) should be within 97.0%-103.0%, calculated from six replicate injections of the Working Standard.

f. Testing Procedure

Separately inject the Blank, the Resolution Solution, the Working Standard, the Check Standard, and the Assay Sample Preparation as shown in the injection scheme below and record the chromatograms. From the peak area responses of the Lactate peak in the Working Standard, calculate the percent of label claim of the Lactate in the Assay Sample Preparation. Blank (2 injections); Resolution Solution (1 injection); Working Standard (6 injections); Check Standard (2 injections); Sample (up to 6 samples); and Bracketing Standard. Lactate content can be calculated as shown below:

Assay (Lactate):

$$\% \ LC = \frac{R_{sam}}{R_{std}} \times \frac{(W_{std} \times P_{std})}{V_{std} \times 112.06} \times \frac{V_{sam}}{D_{sam}} \times \frac{W_t}{W_u} \times \frac{100}{LC}$$

$R_{sam}$=Peak response of Lactate in the sample
$R_{std}$=Peak Response of Lactate in the standard
$W_{std}$=Weight of standard (mg)
$P_{std}$=Purity of standard
$V_{std}$=Volume of standard (mL)
112.06=Molecular weight of sodium lactate
$V_{sam}$=Volume of sample (mL)
$D_{sam}$=Dilution of sample
$W_t$=Average tablet weight of 10 tablets (mg)
$W_u$=Sample weight (mg)
LC=Label claim (theoretical lactate content=10 mEq)

35. Assay for Dissolution Characteristics

Dissolution characteristics for the disclosed compositions can be determined using the techniques set forth below.

a. Dissolution Conditions

Acid Stage: Media: 0.1N HCl 900 mL; Paddles @ 50 rpm; Time: 2 hr; Pull Volume: 10 mL; Filter: 10) um Cannula Filter; and Temperature: 37.0° C.±0.5° C. Buffer Stage: Media: pH 6.8 Citrate Buffer; 900 mL; Paddles @ 50 rpm; Pull Volume: 10 mL; Filter: 10 μm Cannula Filter; and Temperature: 37.0° C.±0.5° C.

b. Solutions Preparation

Lanthanum Diluent: Weigh 2.40±0.05 g Lanthanum Oxide and transfer to a 2.0 L volumetric flask; add 1 L of DI water and 10.0 mL of concentrated HCl. Sonicate solution until the Lanthanum is completely dissolved. Cool to room temperature and dilute to volume with DI water. Mix well.

c. Standard Preparation

Stock Standard: Magnesium AA Standard (about 1000 ppm, commercially available in Nitric Acid). Intermediate Standard: Pipette 10.0 mL of the Stock Standard into a 250-mL volumetric flask and dilute to volume with 0.1N HCl 40 ppm. The various magnesium working standards are prepared as tabulated below:

TABLE 28

| | Volume pH 6.8 Citrate Buffer (mL) | Volume 40 ppm Mg Intermediate Standard (mL) | Volume 0.1N HCl (mL) | Dilute to volume with Lanthanum Diluent (mL) | Concentration of Mg (ppm) |
|---|---|---|---|---|---|
| Blank | 2.0 | 0.0 | 18.0 | 200.0 | 0.00 |
| Standard 1 | 2.0 | 1.0 | 17.0 | 200.0 | 0.2 |
| Standard 2 | 1.0 | 2.0 | 7.0 | 100.0 | 0.8 |
| Standard 3 | 2.5 | 10.0 | 12.5 | 250.0 | 1.6 | d. Sample Preparation

Acid Stage Dilution: Allow dissolution samples to cool room temperature. Transfer 1.0 mL of sample into a 10-mL volumetric flask. Dilute to volume with Lanthanum Diluent, and mix well. Buffer Stage Dilution: Allow dissolution samples to cool room temperature. Transfer 1.0 mL of sample into a 100-mL volumetric flask. Dilute to volume with Lanthanum Diluent, and mix well. If the expected amount of Magnesium dissolved is less than fifteen 15%, then use a 1 to 10 dilution; otherwise use a 1 to 100 dilution.

e. Atomic Absorption (AA) Parameters

Flow Rate (Acetylene): 2.00 L/min; Flow Rate (Air): 10.00 L/min; Lamp: Magnesium Lumina lamp; and Burner: 10 cm×0.25 mm slot. Instrument Set-up: Using the continuous graphics window auto-zero the baseline using the Blank. Optimize the flame height and profile to an absorbance of 0.3000±0.150 using the 1.6-ppm Standard.

f. Testing Procedure

Proceed with AA analysis of the Blank, Standard Solutions, and Samples. The wash solution is DI water, and should be placed in the zero position on the auto sampler. Each Sample, Standard, and Blank should be read in triplicate, and replicates should be averaged for each analysis. A reagent blank should be performed prior to calibration. The calibration is established using standards in the order of lower concentration to highest. After approximately 30 minutes, a recalibration should be performed. In order to minimize cross-contamination, perform a wash before and after calibration. Washing between samples is not required. Follow the sequence: Blank, Standard 1, Standard 2, Standard 3, Blank, Samples, and Recalibration Bracket (Steps 1-5). The linearity curve of the Standard should have a correlation coefficient of NLT 0.999. For the initial calibration curve and subsequent calibration curves, the slopes and intercepts should be compared. The % difference of slopes should be less than 2.0% and the absolute difference in intercepts less than 0.0025. Samples that are bracketed by two calibrations should be compared to the average of the two bracketing curves only.

Calculations can be performed as shown below:

$$\text{Concentration} = \frac{A - b}{m}$$

A=Absorbance
b=Average intercept of bracketing calibration curves
m=Average slope of bracketing calibration curves $$\% \text{ Dissolved} = \left(\frac{C_j \times 238.5 \times (900 - 10n) \times 100\%}{LC \times D_{sam} \times 119.23 \times 24.31 \times 1000}\right) + \sum_{i=1}^{n-1} \frac{C_{i-1} \times 10}{(900 - 10n)}$$

$C_1$=Concentration of sample at initial time point
LC=Label Claim of Magnesium (10 mEq)
$D_{sam}$=Dilution of sample
238.5=Molecular weight of Magnesium Lactate
24.31=Molecular weight of Magnesium
119.23=1 millequivalent of Magnesium in Magnesium Lactate
900=Dissolution Volume (mL)
10=Sampling Volume (mL)
n=Number of timepoints
1000=Conversion of mg to ug Mg
$C_{i-1}$=Concentration of Previous Removed Samples
(900-10n)=Volume of Previously Removed Samples 36. Dissolution of Coated Magnesium Lactate Tablets Using the disclosed procedures, the dissolution characteristics for enteric-coated magnesium lactate tablets (here, MLD09 formulation) were determined. The dissolution results (0.1N HCl— 1% in 2 hours; pH 6.8 buffer) of coated Magnesium Lactate Tablets, 10 mEq (1192.38 mg) are as follows:

TABLE 29

| Time (Hours) | Cumulative % Dissolved |
|---|---|
| 1 | 23 |
| 2 | 38 |
| 4 | 58 |
| 6 | 71 |
| 10 | 90 |

37. Example Formulations

In one aspect, an oral dosage form can be provided as MLD09 Uncoated. For example, the oral dosage form can be provided as a tablet according to the following component list

| Core Tablet | w/w % | mg/tablet |
|---|---|---|
| Mg Lactate Dihydrate, powder | 88.20 | 1192.38 |
| Klucel ® EF* | 9.80 | 132.9 |
| Mg Stearate | 2.00 | 27.04 |
| Tablet Total | 100.00 | 1351.91 |

In a further aspect, an oral dosage form can be provided as MLD09 Subcoated. For example, the oral dosage form can be provided as a tablet according to the following component list.

| Core Tablet | w/w % | mg/tablet |
| --- | --- | --- |
| Mg Lactate Dihydrate, powder | 88.20 | 1192.38 |
| Klucel ® EF* | 9.80 | 132.9 |
| Mg Stearate | 2.00 | 27.04 |
| Tablet Total | 100.00 | 1351.91 |

| 2% Sub-coat | w/w % | mg/tablet |
| --- | --- | --- |
| Opadry ® II Clear (85F19250) | 12.00 | 27 |
| DI Water | 88.00 | Non-residual |
| Tablet Total | 100.00 | 1378.91 |

In a further aspect, an oral dosage form can be provided as MLD09 Enteric coated. For example, the oral dosage form can be provided as a tablet according to the following component list.

| Core Tablet | w/w % | mg/tablet |
| --- | --- | --- |
| Mg Lactate Dihydrate, powder | 88.20 | 1192.38 |
| Klucel ® EF* | 9.80 | 132.9 |
| Mg Stearate | 2.00 | 27.04 |
| Tablet Total | 100.00 | 1351.91 |

| 2% Sub-coat | w/w % | mg/tablet |
| --- | --- | --- |
| Opadry ® II Clear (85F19250) | 12.00 | 27 |
| DI Water | 88.00 | Non-residual |
| Tablet Total | 100.00 | 1378.91 |

| 6% Enteric Coat | w/w % | Solids w/w % | mg/tablet |
| --- | --- | --- | --- |
| Eudragit ® L30D-55 | 56.94 | 83.33 | 67 |
| Triethyl Citrate | 2.56 | 12.50 | 10 |
| Imwitor 900K | 0.85 | 4.17 | 3 |
| DI Water | 39.64 | n/a | Non-residual |
| Tablet Total | 100.0 | 100.00 | 1458.91 |

38. Stability Study of Magnesium Lactate Modified Release Tablets

Figure 25:
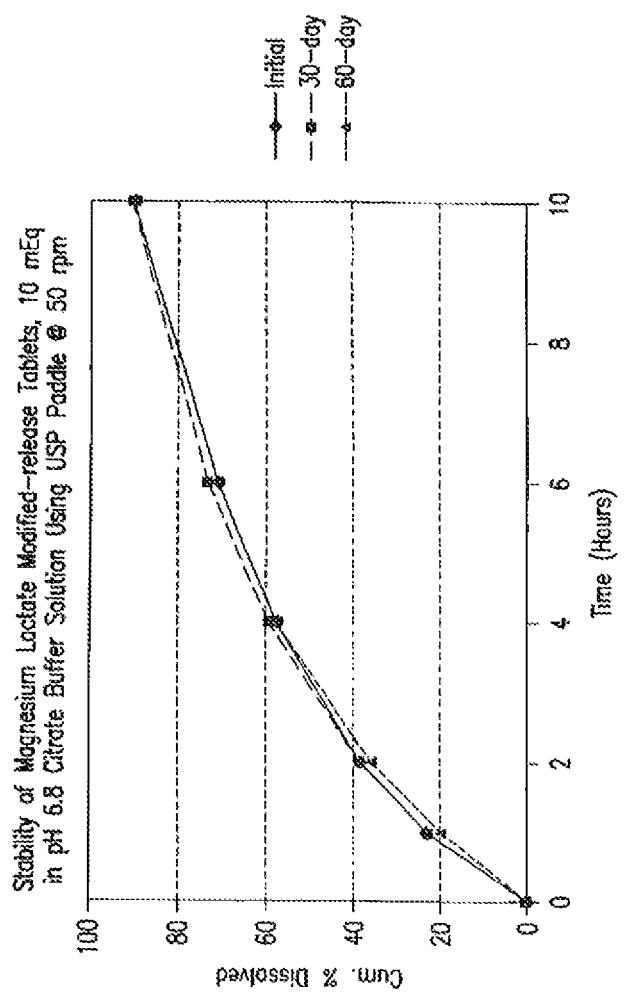
FIG. 25 shows stability of the tablets via dissolution profiles for Magnesium Lactate Modified Release Tablets, 10 mEq, in pH 6.8 citrate buffer solution at times 0, 30, and 60 days.

Dissolution experiments were performed for tablets produced by the disclosed methods. The experiments were conducted with magnesium lactate modified release tablets, 10 mEq, in pH 6.8 citrate buffer solution. Comparison was made among tablets 0 days, 30 days, and 60 days after production. The results are depicted graphically in FIG. 25. It is evident that the disclosed tablets exhibit stable dissolution characteristics from production to at least sixty days.

39. Two Dose Oral Magnesium Load Comparative Trial

A controlled bioavailability trial assessed urinary magnesium excretion after administration of a disclosed sustained release magnesium lactate oral dosage form, MLD09, a new sustained release magnesium L-lactate dihydrate caplet, compared to baseline in five healthy subjects. Urinary excretion was measured after oral magnesium load of magnesium lactate given as two doses spaced six hours apart. Urine was collected for 24 hours, beginning with the initial dose. The test articles were:
  None (i.e., baseline)
  MLD09 Enteric Coated, two 20 mEq doses (total 40 mEq)

The pharmacokinetic profile of magnesium preparations can depend on four factors: the extent of gut absorption into blood, the rate of gut absorption into blood, the transfer rate from blood into muscle, and the transfer rate from blood into urine. Suitable performance includes a high rate and extent of gastrointestinal absorption, a high rate of transfer into muscle, and a low rate of renal wasting of $Mg^{2+}$.

Table 30 shows 24-hour urine magnesium excretion at baseline and after administration of MLD09 for all five subjects. Two of the subjects had normal baseline urinary magnesium excretion, two subjects had low baseline urinary magnesium excretion, and one subject had an incomplete collection of urine during the MLD09 dosing period.

TABLE 30

| | 24 Hour Urine Magnesium (mg) | |
| --- | --- | --- |
| Subject | Baseline | MLD09 |
| Normal Magnesium at Baseline | | |
| 2 | 103.8 | 167.2 |
| 3 | 109.0 | 175.6 |
| Mean | 106.4 | 171.4 |
| Magnesium Deficient at Baseline | | |
| 4 | 35.1 | 52.0 |
| 5 | 60.5 | 76.4 |
| Mean | 47.8 | 64.2 |
| Incomplete Collection during MLD09 Sample Collection | | |
| 1 | 112.0 | 111.0 |
| All Subjects | | |
| Mean | 84.1 | 116.4 |

Figure 26:
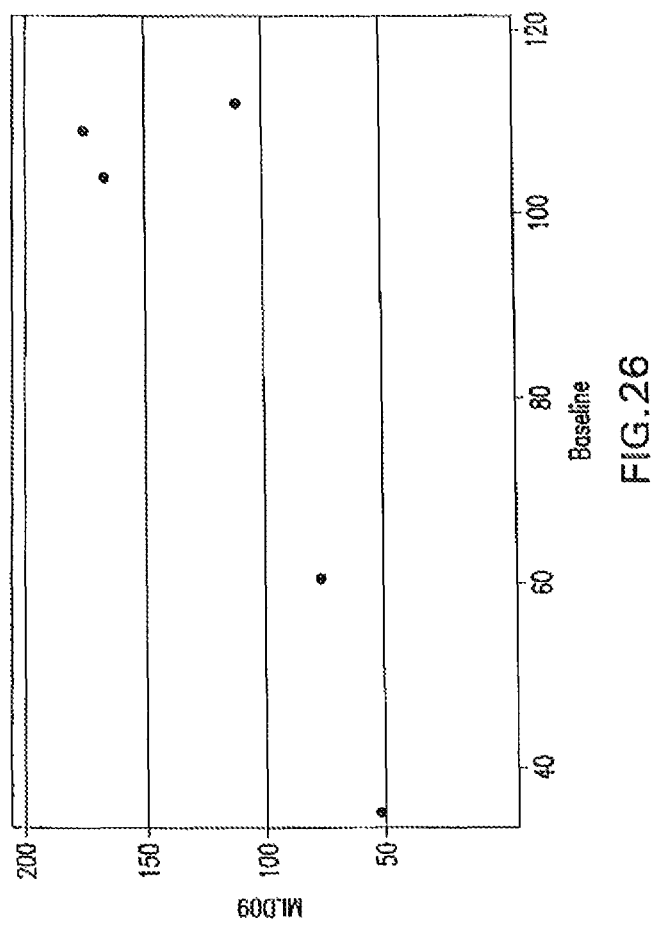
FIG. 26 shows the correlation between urinary $Mg^{2+}$ excretion at baseline and after administration of the coated MLD09 formulation.

FIG. 26 shows the correlation between urinary $Mg^{2+}$ excretion at baseline and after administration of the enteric-coated MLD09 formulation. Subjects with lower intracellular $Mg^{2+}$ stores at baseline have higher uptake of $Mg^{2+}$ via TRPM6/7 transports in the gut and higher $Mg^{2+}$ reabsorption via TRPM6/7 transports in the distal convoluted tubule of the kidney resulting in less renal wasting of $Mg^{2+}$, and greater transfer of blood $Mg^{2+}$ into the intracellular compartment.

None of the subjects reported gastrointestinal or other adverse effects while participating in this trial. The combination of all the above results supports the conclusion that the unique pharmacokinetic profile of MLD09 provides more efficient oral repletion of intracellular magnesium stores than conventional pharmaceutical products, both in terms of oral magnesium dose administered and also number of pills swallowed. The MLD09 formulation is bioavailable in man, as indicated by a 61% increase above baseline of urinary magnesium excretion in subjects with normal urinary magnesium excretion and a 38% increase above baseline in subjects with low urinary magnesium excretion at baseline. Without wishing to be bound by theory, it is believed that subjects with low urinary magnesium excretion at baseline likely had lower urinary magnesium excretion after MLD09 because a substantial fraction of the orally administered dose was transferred to the intracellular magnesium pool in these subjects via TRPM6/7 transports in the distal small intestine and higher $Mg^{2+}$ reabsorption via TRPM6/7 transports in the distal convoluted tubule of the kidney. Accordingly, this can result in less renal wasting of $Mg^{2+}$ and greater transfer of blood $Mg^{2+}$ into the intracellular compartment.

It will be apparent to those skilled in the art that various modifications and variations can be made in the present disclosure without departing from the scope or spirit of the present disclosure. Other aspects of the disclosure will be apparent to those skilled in the art from consideration of the specification and practice of what is disclosed herein. It is intended that the specification and examples be considered as exemplary only, with a true scope and spirit of the present disclosure being indicated by the following claims.

The invention claimed is:

1. A method of treating low magnesium levels in a mammal, the method comprising:
    administering to the mammal a therapeutically effective amount of magnesium salt in an oral dosage form, the oral dosage form comprising magnesium lactate from about 80% to about 95% by weight of the dosage form and one or more excipients present from about 5% to about 20% by weight of the dosage form, the oral dosage form having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours.

2. The method of claim 1 wherein the one or more excipients is hydroxypropyl cellulose.

3. The method of claim 1 wherein the one or more excipients is hydroxypropyl cellulose and magnesium stearate.

4. The method of claim 1 wherein the therapeutically effective amount is sufficient to restore depleted serum magnesium levels to a therapeutically acceptable level.

5. The method of claim 1 wherein the therapeutically effective amount is sufficient to restore depleted intracellular magnesium levels to a concentration of at least about 33.9 mEq/IU.

6. The method of claim 5 wherein the intracellular magnesium levels are restored to a concentration of at least 33.9 mEq/IU within about 51 hours after administration.

7. A method of making a controlled release dosage form for oral administration of a therapeutically effective amount of magnesium salt to a mammal, the method comprising:
    using fluid bed granulation, granulating the magnesium salt;
    blending the granulated magnesium salt and one or more excipients; and
    applying pressure to the blend of granulated magnesium salt and the one or more excipients sufficient to form the dosage form, wherein the magnesium salt comprises about 80% to about 95% by weight of the dosage form, the one or more excipients comprise from about 5% to about 20% by weight of the dosage form, and the dosage form having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours.

8. The method of claim 7 wherein the magnesium salt is selected from the group comprising:
    magnesium carbonate, magnesium chloride, magnesium citrate, magnesium fumerate, magnesium gluconate, magnesium glycinate, magnesium L-lactate, magnesium oxide, magnesium DL-aspartate, magnesium L-aspartate, magnesium hydroxide, magnesium salicylate, magnesium sulfate, magnesium aminoate, magnesium phosphate, magnesium acetate, magnesium pidolate, magnesium malate, and magnesium picolinate.

9. The method of claim 7 wherein the magnesium salt is magnesium lactate.

10. The method of claim 7 wherein the one or more excipients is hydroxypropyl cellulose.

11. The method of claim 7 wherein the one or more excipients is hydroxypropyl cellulose and magnesium stearate.

12. The method of claim 7 wherein the pressure is sufficient to form the dosage form having a hardness from about 15 kp to about 30 kp.

13. The method of claim 7 further comprising:
    applying one or more coatings to the dosage form after applying pressure.

14. A method of treating low magnesium levels in a mammal, the method comprising:
    administering to the mammal a therapeutically effective amount of magnesium salt in an oral dosage form, the dosage form including a magnesium salt having an uncoated core dissolution profile under the Tablet Dissolution Test characterized by no more than about 40% by weight magnesium salt released at 1 hour, at least about 50% by weight magnesium salt released at 6 hours, and at least about 85% by weight magnesium salt released at 10 hours.

15. The method of claim 14 wherein the magnesium salt is selected from the group comprising:
    magnesium carbonate, magnesium chloride, magnesium citrate, magnesium fumerate, magnesium gluconate, magnesium glycinate, magnesium L-lactate, magnesium oxide, magnesium DL-aspartate, magnesium L-aspartate, magnesium hydroxide, magnesium salicylate, magnesium sulfate, magnesium aminoate, magnesium phosphate, magnesium acetate, magnesium pidolate, magnesium malate, and magnesium picolinate.

16. The method of claim 14 wherein the magnesium salt is magnesium lactate.

* * * * *